(12) United States Patent
Sayre et al.

(10) Patent No.: US 12,180,481 B2
(45) Date of Patent: Dec. 31, 2024

(54) TARGETED EXTRACELLULAR VESICLES FOR DELIVERY OF THERAPEUTICS

(71) Applicant: Mercury Bio, Inc., Santa Fe, NM (US)

(72) Inventors: Richard Sayre, Los Alamos, NM (US); Tatiana Vinogradova-Shah, Rochester, NY (US); Alexander Pertzev, Santa Fe, NM (US)

(73) Assignee: Mercury Bio, Inc., Santa Fe, NM (US)

( * ) Notice: Subject to any disclaimer, the term of this patent is extended or adjusted under 35 U.S.C. 154(b) by 0 days.

(21) Appl. No.: 18/275,591

(22) PCT Filed: Feb. 2, 2022

(86) PCT No.: PCT/US2022/014958
§ 371 (c)(1),
(2) Date: Aug. 2, 2023

(87) PCT Pub. No.: WO2022/169885
PCT Pub. Date: Aug. 11, 2022

(65) Prior Publication Data
US 2024/0150763 A1 May 9, 2024

Related U.S. Application Data

(60) Provisional application No. 63/184,011, filed on May 4, 2021, provisional application No. 63/144,827, filed on Feb. 2, 2021.

(51) Int. Cl.
| | |
|---|---|
| *C12N 1/19* | (2006.01) |
| *A61K 9/50* | (2006.01) |
| *A61P 31/14* | (2006.01) |
| *C07K 14/515* | (2006.01) |
| *C07K 14/705* | (2006.01) |
| *C12N 1/18* | (2006.01) |
| *C12N 15/113* | (2010.01) |
| *C12Q 1/68* | (2018.01) |
| *C12R 1/865* | (2006.01) |

(52) U.S. Cl.
CPC ........ *C12N 15/1131* (2013.01); *A61K 9/5068* (2013.01); *A61P 31/14* (2018.01); *C07K 14/515* (2013.01); *C07K 14/705* (2013.01); *C12N 1/185* (2021.05); *C12N 2310/122* (2013.01); *C12R 2001/865* (2021.05)

(58) Field of Classification Search
None
See application file for complete search history.

(56) References Cited

U.S. PATENT DOCUMENTS

| | | | |
|---|---|---|---|
| 11,234,934 B1 * | 2/2022 | Leigh | A23L 33/135 |
| 2016/0331686 A1 * | 11/2016 | Polach | C12N 15/111 |
| 2021/0260201 A1 * | 8/2021 | Chukly | A61K 47/6901 |
| 2021/0348167 A1 * | 11/2021 | Vieira Araujo Soares Da Silva | C12N 15/1131 |

FOREIGN PATENT DOCUMENTS

| | | |
|---|---|---|
| RU | 2733361 C1 | 10/2020 |
| WO | 2019027847 A1 | 2/2019 |
| WO | WO 2021212066 | * 10/2021 |

OTHER PUBLICATIONS

Dawson et al, Protein markers for Candida albicans EVs include claudin-like Sur7 family proteins, Journal of Extracellular Vesicles, 2020, pp. 1-20.*

Cantuti et al, Neuropilin-1 facilitates SARS-CoV-2 cell entry and infectivity, Science 370, 2020, 856-860.*

GenBank Accession No. KC191350, Hypophthalmichthys nobilis microsatellite Arsd152 sequence. Sep. 3, 2014 [online]. [Retrieved on Jun. 8, 2022]. Retrieved from the internet: <URL: https://www.ncbi.nlm.nih.gov/nuccore/KC191350> Full document, especially sequence nts 1337-1380.

Cai et al. Message in a bubble: shuttling small RNAs and proteins between cells and interacting organisms using extracellular vesicles. Annual review of plant biology. Jun. 17, 2021, vol. 72, p. 497-524. (Author Manuscript) Full document.

* cited by examiner

*Primary Examiner* — Maria Marvich
(74) *Attorney, Agent, or Firm* — Berg Hill Greenleaf Ruscitti LLP

(57) ABSTRACT

The present invention is directed to *Saccharomyces*-generated extracellular vesicles (EVs) comprising a foreign RNA molecule or protein and at least one foreign membrane surface exposed ligand that specifically binds to a target receptor displayed on a target cell. The present invention also relates to methods of making and using these *Saccharomyces*-generated EVs for targeted gene silencing. The present invention also relates to fusion proteins comprising a *Saccharomyces* extracellular vesicle anchor protein and a second peptide designed to bind to cell-specific receptors.

16 Claims, 11 Drawing Sheets
Specification includes a Sequence Listing.

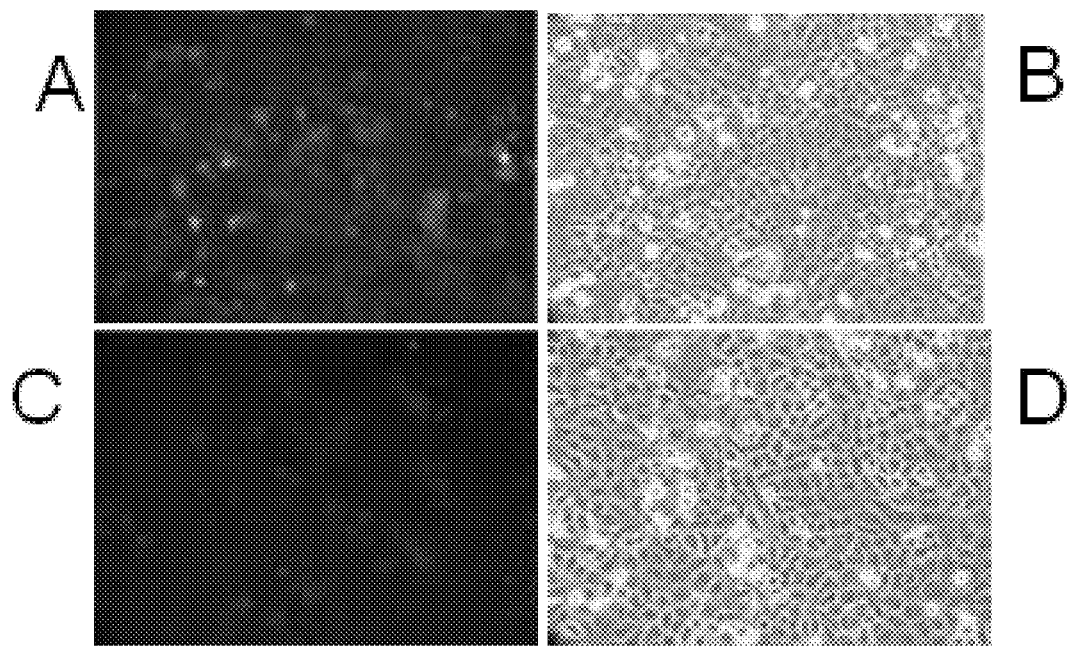
FIG. 5A-D
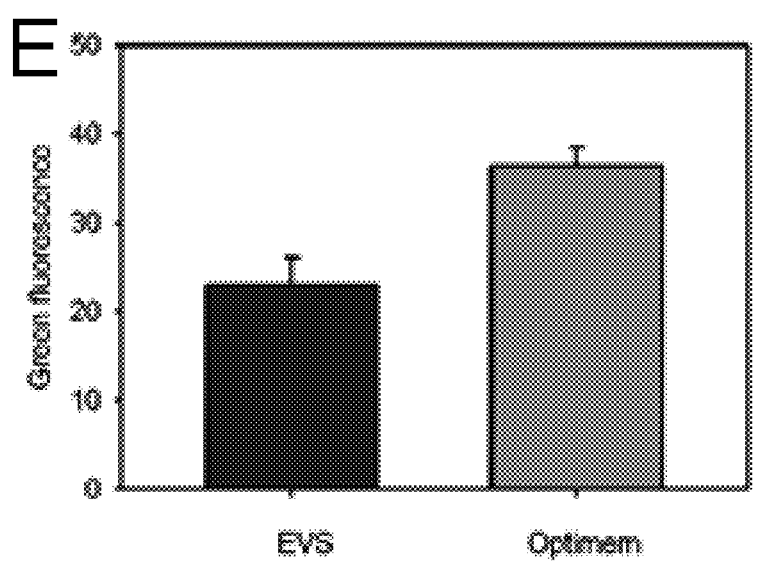
FIG. 5E

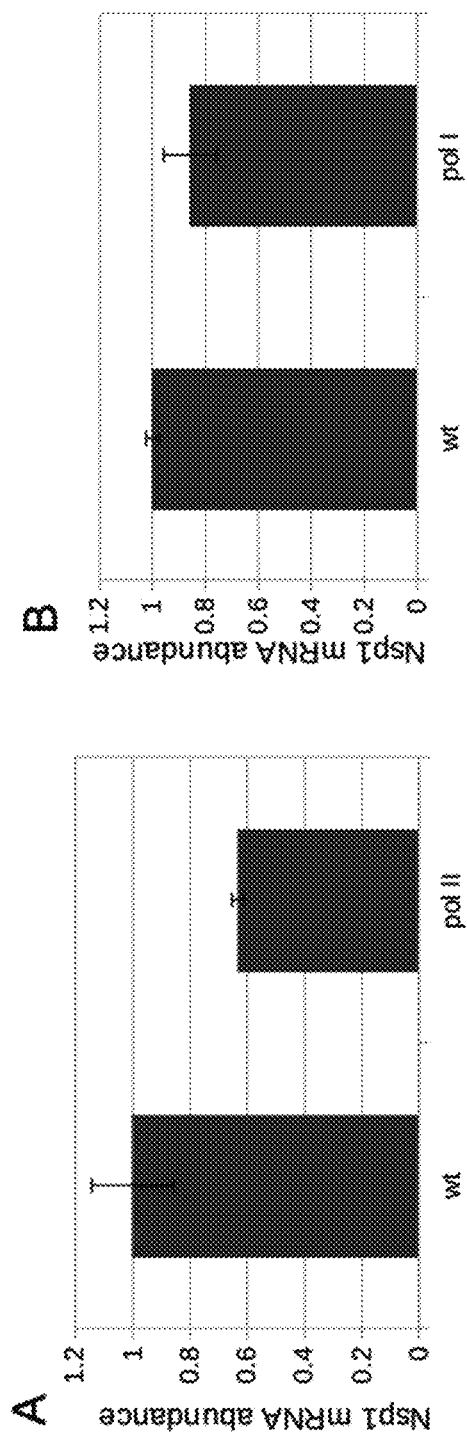
FIG. 6A-B

FIG 8A-B

TARGETED EXTRACELLULAR VESICLES FOR DELIVERY OF THERAPEUTICS

CROSS-REFERENCE TO RELATED APPLICATIONS

This application is a national stage application under 35 U.S.C. 371 of PCT Applicatoin No. PCT/US22/14958 having an international filing date of Feb. 2, 2022, which designated the United State, which PCT application claimed the benefit of U.S. Application Ser. No. 63/144,827, filed Feb. 2, 2021, both of which are incorporated by reference in their entirety.

SEQUENCE LISTING

The instant application contains a Sequence Listing which has been submitted electronically in ASCII format and is hereby incorporated by reference in its entirety. Said ASCII copy, created on Aug. 2, 2023, is named "90355.00042-Sequence-Listing-AF" and is 76 Kbytes in size.

TECHNICAL FIELD

The present invention is directed to *Saccharomyces*-generated extracellular vesicles (EVs) comprising a foreign RNA molecule or protein and at least one foreign membrane surface ligand that specifically binds to a target molecule displayed on a target cell. The present invention also relates to methods of making and using these *Saccharomyces*-generated EVs. The present invention also relates to fusion proteins comprising a *Saccharomyces* extracellular vesicle anchor protein and a second peptide.

BACKGROUND

Ever since the discovery that RNA that can be used to silence genes via RNAi, there has been a need for efficient and specific delivery of the RNA to target cells. As naked nucleic acids are difficult to deliver in vivo due to rapid clearance, nucleases, lack of organ-specific distribution and low efficacy of cellular uptake, there have been attempts to generate specialized gene delivery vehicles for nucleic acid delivery. Viral vectors and liposomes have been relatively successful in delivering nucleic acids, with a large number of these delivery vehicles in clinical trial. Despite these minor successes, there remain significant limitations that restrict the broad use of nucleic acid delivery to specific target cells, some of which include immune recognition and possible neutralization for most viral vectors, mutagenic integration of viruses such as lentiviruses and inflammation toxicity and rapid clearance of liposomes. Liposomes and viral vectors can sometimes trigger the innate immune system, which leads to acute inflammatory responses, which may, in turn, require the use of immunosuppression strategies to overcome uptake and re-administration issues potentially exposing patients to unwarranted risks of opportunistic infections. Antibodies generated against the delivery vehicles may also decrease transgene expression on subsequent administration.

Hence, it is imperative to develop technologies that are able to avoid immune recognition and inflammation, while retaining good delivery efficiencies to expand the use of RNAi therapy as a more routine treatment. One of the solutions may lie in the use of extracellular vesicles, e.g., exosomes, for nucleic acid delivery. Extracellular vesicles (EVs) such as exosomes are small membrane-bound vesicles generally of endocytic origin that are released into the extracellular environment. There are several pathways that can result in formation of EVs. The potential of exosome-mediated gene delivery has been shown with delivery of murine mRNAs and miRNAs to human mast cells in vitro.

There are questions as to whether "allogeneic exosomes" would trigger an adaptive immune response in the subject receiving the EVs and how quickly and efficient "syngeneic exosomes" could be generated. Thus, there still exists in the art a need to efficiently and quickly produce EVs that are capable of carrying genetic cargo and which the body's immune system will either tolerate or ignore. To date, there has been no successful generation of EVs from yeast that are normally consumed and have been engineered to specifically and directly bind to a target cell to deliver a nucleic acid payload.

SUMMARY OF THE INVENTION

The present invention is directed to extracellular vesicles (EVs) comprising a foreign RNA molecule or protein derived from an Generally Recognized As Safe (GRAS) organism as defined by the U.S. Food and Drug Administration. In this preferred embodiment, the present invention is directed to EVs comprising a foreign RNA molecule or protein derived from *Saccharomyces*, such as *Saccharomyces cerevisiae* (sometimes referred to herein as Sc) or *Saccharomyces boulardii* (sometimes referred to herein as Sb).

The present invention is directed to EVs comprising a foreign RNA molecule or protein derived from an organism that is probiotic with a subject to be treated. In this preferred embodiment, the present invention is directed to EVs comprising a foreign RNA molecule or protein derived from probiotic *Saccharomyces*, and in particular probiotic *Saccharomyces boulardii*.

In present invention includes systems, methods and compositions for a *Saccharomyces*-generated EVs (sometimes referred to as exosome) platform for the delivery of therapeutic RNA, particularly small interfering RNA (siRNA) for the treatment of a disease or condition in a subject in need thereof, including viral infection, cancer, or inherited metabolic disorder.

In present invention includes systems, methods and compositions for a *Saccharomyces*-generated EVs (sometimes referred to as exosome) platform for the delivery of therapeutic RNA, particularly small interfering RNA (siRNA) for targeted gene silencing. In a preferred embodiment, the targeted gene silencing may be directed to a pathogen gene, or an endogenous gene expressed by a target cell or host, and preferably a subject.

In present invention includes systems, methods and compositions for a *Saccharomyces*-generated EVs (sometimes referred to as exosome) platform for the delivery of therapeutic RNA, particularly small interfering RNA (siRNA) for the treatment of SARS-CoV-2 virus in a subject in need thereof.

The present invention includes *Saccharomyces*-generated EVs comprising a foreign RNA molecule or protein and at least one foreign membrane surface ligand that specifically binds to a target molecule displayed on a target cell.

The present invention also relates to methods of making and using these *Saccharomyces*-generated EVs. The present invention also relates to fusion proteins comprising a *Saccharomyces* extracellular vesicle anchor protein and a second peptide.

Figure 1:
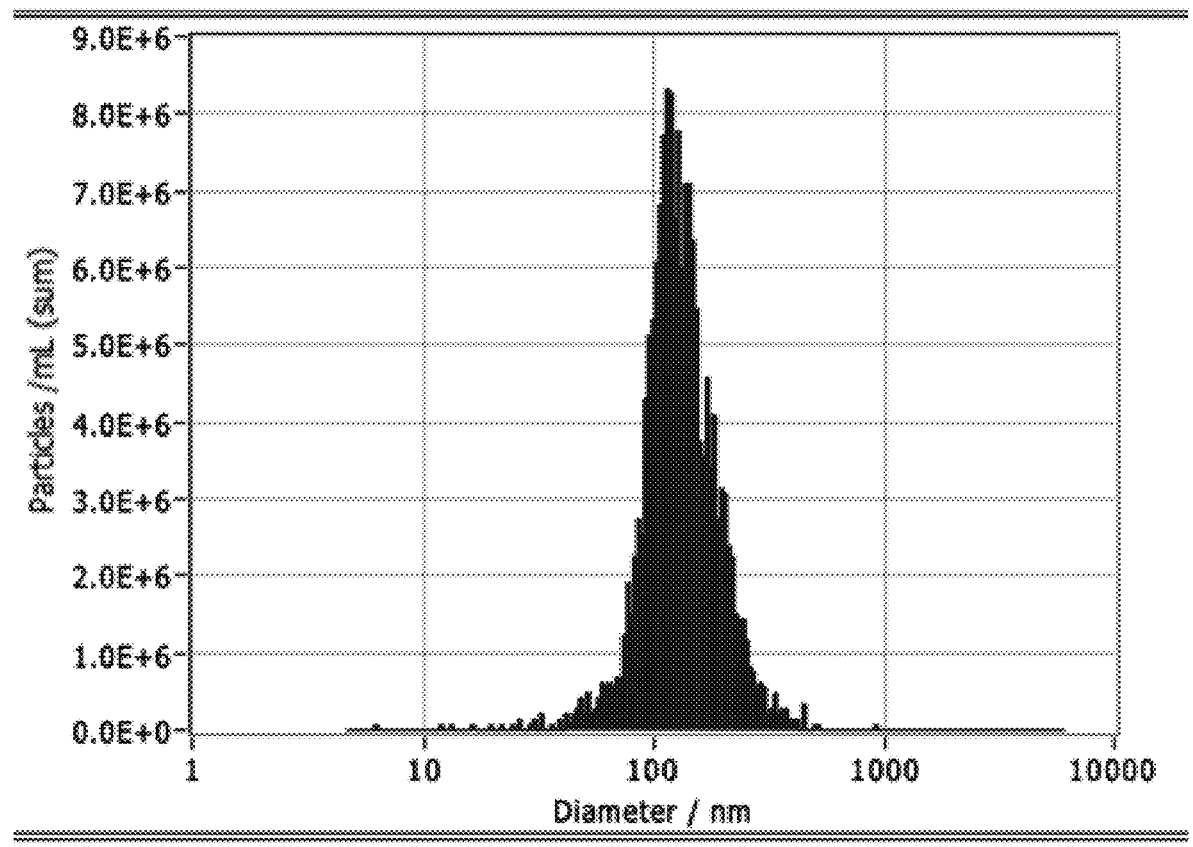
FIG. 1 show NTA analysis of Exosomes (EVs) derived from Sb culture.

Generally speaking, the siRNA delivered to the target cell or the RNA delivered to the target cell that is processed into siRNA will contain one strand, i.e., the guide strand, that is perfectly (100%) complementary to a small stretch, about 15-23 bases, to a sequence within the target mRNA. Thus, the siRNA delivered to the target cell or the RNA delivered to the target cell that is processed into siRNA is not necessarily limited to a specific nucleotide sequence, except that the siRNA that is delivered or derived within the cell after delivery may be designed to have one strand that is 100% complementary to between about 15-23 bases of a target mRNA.

The sequences of various siRNAs directed to SARS-CoV-2 are now well-known. For example, Medeiros, I., et al., *Scientific Reports,* 11: 8849 (2021) (e-published 23 Apr. 2021) (doi.org/10.1038/s41598-021-88310-8), which is incorporated by reference, discloses siRNA sequences of SARS-CoV-2. In particular, the database located at doi.org/10.17605/OSF.IO/WD9MR, which is incorporated by reference, discloses siRNAs of 18, 19, 20 or 21 nucleotides in length that are directed to SARS-CoV-2. The siRNAs disclosed in these references or databases can be delivered to the target cells using the SGEVs of the present invention.

In one embodiment, the RNA that is delivered to target cells is not chemically modified. In another embodiment, the RNA that is delivered to the target cells is crosslinked RNA, such as but not limited to crosslinked siRNA. Crosslinked siRNA derivatives are as described in U.S. Pat. No. 10,087 441, which is incorporated herein by reference in its entirety. Crosslinking can be employed to alter the pharmacokinetics of the composition, for example, to increase the half-life in the body. Thus, the invention includes delivery of siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative delivered to the target cells can contain a single crosslink, e.g., a psoralen crosslink. In some embodiments, the siRNA derivative has at its 3' terminus a biotin molecule, e.g., a photocleavable biotin, a peptide, a peptidomimetic, a nanoparticle, organic compounds, e.g., a dye such as a fluorescent dye, or a dendrimer. Modifying siRNA derivatives in this way may improve EV uptake or enhance targeting activities of the resulting siRNA derivative as compared to the corresponding siRNA and may be useful for tracing the siRNA derivative in the cell or improving the stability of the siRNA derivative compared to the corresponding siRNA. As such, one skilled in the art can screen crosslinked siRNA derivatives that are modified with various methods to determine whether the crosslinked siRNA derivatives possesses improved properties while maintaining the ability to mediate RNAi as are generally known in the art.

In another embodiment, the RNA delivered to the target cell is ssRNA. The ssRNA delivered to the target cells may act, for example, as a guide strand that would normally be part of an siRNA molecule. In this specific embodiment, the ssRNA that is delivered to the target cells does not need any additional cellular processing, e.g., dicer and/or argonaut, before it can be used to promote gene silencing within the target cell. In another embodiment, the ssRNA that is delivered to the target cell can act as an miRNA.

In yet another embodiment, RNA can be delivered to a target cell and, if necessary, the cell can process the delivered RNA into miRNA. As is well-known in the art, miRNA is a type of RNA that can also suppress gene expression, either by inhibiting translation of mRNA or by promoting degradation of mRNA. Generally speaking, miRNA is ssRNA that can be between about 20-25 nucleotides in length and is often complementary to the untranslated region (UTR) of an mRNA transcript. The RNA that is delivered to the target cell, e.g., dsRNA, may be processed within the target cell to produce the miRNA, or the RNA delivered to the target cell can be miRNA. If the RNA delivered to the cells is to be processed into miRNA, the delivered RNA may be between about 60-100 nucleotides in length and, in one embodiment, is internally complementary to itself such that it can fold back on itself to form short hairpin RNA duplexes. The RNA duplex regions of the short hairpin RNA that include the miRNA need not be 100% perfectly complementary along the double stranded stretch of the RNA duplex. Thus, the short hairpin RNA containing the miRNA may include "bulges" in which short regions within the duplex structure do not base pair with one another.

Similar to siRNA sequences, the nucleotide sequence of miRNAs delivered to the target cell or the RNA delivered to the target cell that is processed into miRNA is not necessarily limited to a specific nucleotide sequence, except that the miRNA that is delivered or derived within the cell after delivery may be designed to have one strand that is perfectly or predominantly complementary to between about 15-23 bases of a target mRNA. As used herein, a predominantly complementary strand of RNA may have no more than about 4 bases over a 15-23 nucleotide length that are not complementary to the target mRNA.

In specific embodiments, the RNA delivered to the target cells is an miRNA directed against SARS-CoV-2. The sequences of various miRNAs in SARS-CoV-2 are now well-known. For example, Yu, T. et al., *J. Elec. Sci. Tech.* (e-published 6 Dec. 2020) (doi.org/10.1016/j.jnlest.2020.100060), which is incorporated by reference, discloses miRNA sequences of SARS-CoV-2. EI-Nabi, S., et al., *Med Hypotheses,* 143:110203 (2020) (doi: 10.1016/j.mehy.2020.110203), which is incorporated by reference, also discloses miRNAs directed against ORF9, the 3' UTR and the 5'UTR of SARS-CoV-2. Mirzaei, R., et al., *J. Int'l. Immunopharm.,* (e-published 13 Nov. 2020) (doi.org/10.1016/j.intimp.2020.107204), which is incorporated by reference, also discloses miRNAs that can be used for gene silencing of various genes of SARS-CoV-2, and therefore suppress viral replication in the target cell.

In additional embodiments, the RNA that is delivered to the target cells is an miRNA that can suppress innate immunity response in target cells. For example, the RNA delivered to the target cells is human, miR-231, miR-223 or miR-451. Established miRNA databases provide specific sequences of miRNAs in humans and other mammals that are involved in regulation of gene expression. For example, the MiRBase (mirbase.org/) (Kozomara, A. and Griffiths-Jones, S., *Nucleic Acids Res.,* 42:D68-D73 (2014), which are incorporated by reference) discloses miRNAs that may be delivered to the target cells using the SGEVs of the present invention.

In yet another embodiment, the RNA that is delivered to the target cells can be short hairpin RNA (shRNA). As used herein, shRNA is a duplex RNA in which a single RNA strand is internally complementary to itself such that it can fold back on itself to form an RNA duplex. The shRNA may then be further processed in the cell to, for example, miRNA or siRNA.

In some embodiments of the present invention, the delivered RNA is RNA that is directed against at least one of the ORF1ab, ORF3a, ORF7a, ORF8, S protein, N protein, the RdRp protein or M protein ORF, or the 5'-nsp1 region or 5'UTR region of the Severe Acute Respiratory Syndrome-Related Coronavirus 2 (SARS-CoV-2) virus. The polynucleotide sequences of each of these ORFs or region of the SARS-CoV-2 virus are well-known. See National Center for Biotechnology and Information (NCBI) Accession Number NC_045512.2 (available on the world wide web at (ncbi.nlm.nih.gov/nuccore/NC_045512.2) and Wu, F., et al., Nature, 579 (7798):265-269 (2020) both of which are incorporated by reference.

In some embodiments of the present invention, the RNA delivered to a target cell, may include a shRNA delivered to a target cell by SGEVs. In this preferred embodiment, the SGEV may express a heterologous nucleotide sequence, operably linked to a promoter, according to the nucleotide sequence SEQ ID NO. 1. In another embodiment, of the present invention, the RNA delivered to a target cell, may include a shRNA delivered to a target cell by a SGEV. In this preferred embodiment, the SGEV may express a heterologous nucleotide sequence, operably linked to a promoter, having at least 98% sequence identity to the nucleotide sequence of SEQ ID NO. 1. In a preferred embodiment, the target cell may be infected with, or at risk of infection by SARS-CoV-2.

In some embodiments of the present invention, the RNA delivered to a target cell, may include a shRNA delivered to a target cell by SGEVs. In this preferred embodiment, the SGEV may express a heterologous nucleotide sequence, operably linked to a promoter, according to the nucleotide sequence SEQ ID NO. 18. In another embodiment, of the present invention, the RNA delivered to a target cell, may include a shRNA delivered to a target cell by a SGEV. In this preferred embodiment, the SGEV may express a heterologous nucleotide sequence, operably linked to a promoter, having at least 98% sequence identity to the nucleotide sequence of SEQ ID NO. 18. In a preferred embodiment, the target cell may be infected with, or at risk of infection by SARS-CoV-2.

In some embodiments of the present invention, the RNA delivered to a target cell, may include a shRNA delivered to a target cell by SGEVs transformed by, and expressing by a heterologous expression vector. In this preferred embodiment, the invention may include an expression vector configured to be integrated into the genome of a yeast cell, and preferably a Sb yeast cell, and express an RNA oligonucleotide. The expression vector of the invention may include a heterologous nucleotide sequence, operably linked to a promoter, having a nucleotide sequence according to SEQ ID NO. 1. In another embodiment, The expression vector of the invention may include a heterologous nucleotide sequence, operably linked to a promoter, having a nucleotide sequence with at least 98% sequence identity to the nucleotide sequence of SEQ ID NO. 1. In a preferred embodiment, the target cell may be infected with, or at risk of infection by SARS-CoV-2.

In some embodiments of the present invention, the RNA delivered to a target cell, may include a shRNA delivered to a target cell by SGEVs transformed by, and expressing by a heterologous expression vector. In this preferred embodiment, the invention may include an expression vector configured to be integrated into the genome of a yeast cell, and preferably a Sb yeast cell, and express an RNA oligonucleotide. The expression vector of the invention may include a heterologous nucleotide sequence, operably linked to a promoter, having a nucleotide sequence according to SEQ ID NO. 18. In another embodiment, The expression vector of the invention may include a heterologous nucleotide sequence, operably linked to a promoter, having a nucleotide sequence with at least 98% sequence identity to the nucleotide sequence of SEQ ID NO. 18. In a preferred embodiment, a target cell is a cell of a subject, and preferably a human subject. The target cell of the invention may be established in vitro or in vivo, and may be part of an organ or tissue. In a preferred embodiment, the target cell may be infected with, or at risk of infection by SARS-CoV-2.

As noted above, there are well-established "rules" for determining one or more polynucleotide sequences that can be directed against a specific target gene for silencing. As used herein, the phrase "directed against" or "directed to" when used in conjunction with RNA means that the RNA comprises at least one strand that is designed to promote gene silencing for a target gene. In one embodiment, the delivered RNA of the present invention comprises a nucleotide sequence of at least 20 contiguous nucleotides directed against at least one of the ORF1ab, ORF3a, ORF7a, ORF8, S protein, N protein, the RdRp protein or M protein ORF, or the 5'-nsp1 region or 5'UTR region of the SARS-CoV-2 virus. In one embodiment, the invention may include a shRNA directed to the nsp1 gene or region of the SARS-CoV-2 virus. In a preferred embodiment, the invention may include a shRNA according to the nucleotide sequence SEQ ID NO 1 or 18, directed to the nsp1 gene or region of the SARS-CoV-2 virus.

In some embodiments of the present invention, the expression vector of the invention may include one or more nucleotide sequences configured to facilitate integration and expression of a heterologous nucleotide sequence, encoding at least one RNA. In this embodiment, exemplary nucleotide sequence nucleotide sequences configured to facilitate integration and expression of a heterologous expression cassette, encoding at least one RNA may include SEQ ID NO.'s 3-11.

In some embodiments of the present invention, the invention may include a kit for the treatment of a disease or condition in a subject in need thereof. In this preferred embodiment, the kit of the invention may include a quantity of SGEVs containing one or more RNAs directed to inhibit the expression of one or more pathogen genes, or one or more endogenous genes in a subject. The quantity of SGEVs may be provided in a container, or other suitable receptacle or a quantity of SGEVs pre-loaded into a device for administration to a subject, preferably in a standard or customizable dosage. Optionally, the kit of the invention may include instructions for use.

In another preferred embodiment, the kit of the invention may include one or more yeast cells or cultures expressing a heterologous nucleotide sequence, operably linked to a promoter, encoding an RNA oligonucleotide (generally referred to herein as an RNA), and preferably an RNA directed to inhibit the expression of one or more pathogen genes, or one or more endogenous genes in a subject. The quantity of more yeast cells or cultures may be provided in a container, or other suitable receptacle and may be used to seed a culture for growth in a fermenter. Optionally, the kit of the invention may include instructions for use and fermentation.

In some embodiments of the present invention, the invention may include a kit for the treatment of a SARS-CoV-2 virus in a subject in need thereof. In this preferred embodiment, the kit of the invention may include a quantity of SGEVs containing one or more RNAs directed to inhibit the expression of one or more SARS-CoV-2 genes. In a preferred embodiment, the SGEVs of the kit may contain an RNA according to SEQ ID NO. 18, or a sequence having at least 98% sequence identify with SEQ ID NO. 18. The quantity of SGEVs may be provided in a container, or other suitable receptacle or a quantity of SGEVs pre-loaded into a device for administration to a subject, preferably in a standard or customizable dosage. Optionally, the kit of the invention may include instructions for use.

In another preferred embodiment, the kit of the invention may include one or more yeast cells or cultures expressing a heterologous nucleotide sequence, operably linked to a promoter, encoding an RNA, and preferably an RNA directed to inhibit the expression of one or more SARS-CoV-2 genes. The yeast cells or cultures may express a heterologous nucleotide sequence, operably linked to a promoter, encoding a nucleotide sequence according to SEQ ID NO. 1, or a sequence having at least 98% sequence identify with SEQ ID NO. 1. The quantity of more yeast cells or cultures may be provided in a container, or other suitable receptacle and may be used to seed a culture for growth in a fermenter. Optionally, the kit of the invention may include instructions for use and fermentation.

In certain embodiments, the invention may include a pharmaceutical composition including a quantity of SGEVs containing one or more RNAs directed to inhibit the expression of one or more pathogen or endogenous host genes, and a pharmaceutically acceptable carrier. In certain embodiments, the invention may include a pharmaceutical composition including a quantity of SGEVs containing one or more RNAs directed to inhibit the expression of one or more SARS-CoV-2 genes, and a pharmaceutically acceptable carrier. In another specific preferred embodiment, the invention may include a pharmaceutical composition including a quantity of SGEVs containing one or more RNAs according to SEQ ID NO. 18, and a pharmaceutically acceptable carrier In a preferred embodiment, the SGEVs of the kit may contain an RNA according to SEQ ID NO. 18, or a sequence having at least 908% sequence identify with SEQ ID NO. 18. The term "pharmaceutically acceptable" as used herein, refer to molecular entities and compositions that do not produce adverse, allergic, or other untoward reactions when administered to an animal or a human. The term, "pharmaceutically acceptable carrier" as used herein, includes any and all solvents, or a dispersion medium including, but not limited to, water, ethanol, a polyol (for example, glycerol, propylene glycol, and liquid polyethylene glycol, stachyose, and the like), suitable mixtures thereof, and vegetable oils, coatings, isotonic and absorption delaying agents, liposomes, commercially available cleansers, and the like. Supplementary bioactive ingredients also can be incorporated into such carriers.

The term "endogenous" gene or protein means that said gene or protein is expressed from a gene naturally found in the genome of a eukaryotic cell. The term "heterologous" gene or protein means that said gene or protein is not expressed from a gene naturally found in the genome of a eukaryotic cell. As used herein, the term "gene" or "polynucleotide" refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylated), nucleic acid analogs or non-naturally occurring nucleic acids and can be interrupted by non-nucleic acid residues. For example, a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

As used herein, the phrase "expression," "gene expression" or "protein expression," such as the level of includes any information pertaining to the amount of gene transcript or protein present in a sample, in a cell, in a patient, secreted in a sample, and secreted from a cell as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc. The term "expression levels" refers to a quantity reflected in or derivable from the gene or protein expression data, whether the data is directed to gene transcript accumulation or protein accumulation or protein synthesis rates, etc. Polypeptides encoded by a target molecule genes that may be targeted for expression inhibition, for example through an RNAi mediated process herein may reflect a single polypeptide or complex or polypeptides. Accordingly, in another embodiment, the invention provides a polypeptide that is a fragment, precursor, successor or modified version of a protein target molecule described herein. In another embodiment, the invention includes a protein target molecule that comprises a foregoing fragment, precursor, successor or modified polypeptide. As used herein, a "fragment" of a polypeptide refers to a single amino acid or a plurality of amino acid residues comprising an amino acid sequence that has at least 5 contiguous amino acid residues, at least 10 contiguous amino acid residues, at least 20 contiguous amino acid residues or at least 30 contiguous amino acid residues of a sequence of the polypeptide. As used herein, a "fragment" of poly- or oligo-nucleotide refers to a single nucleic acid or to a polymer of nucleic acid residues comprising a nucleic acid sequence that has at least 15 contiguous nucleic acid residues, at least 30 contiguous nucleic acid residues, at least 60 contiguous nucleic acid residues, or at least 90% of a sequence of the polynucleotide. In some embodiment, the fragment is an antigenic fragment, and the size of the fragment will depend upon factors such as whether the epitope recognized by an antibody is a linear epitope or a conformational epitope. Thus, some antigenic fragments will consist of longer segments while others will consist of shorter segments, (e.g., 5, 6, 7, 8, 9, 10, 11 or 12 or more amino acids long, including each integer up to the full length of the polypeptide). Those skilled in the art are well versed in methods for selecting antigenic fragments of proteins.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "introducing," "administered" or "administering", as used herein, refers to any method of providing a composition of SGEVs to a patient such that the composition has its intended effect on the patient. In one embodiment, SGEVs may be introduced to a patient in vivo, while in other alternative embodiments, SGEVs may be introduced to subject cells in vitro which may then be administered to a patient in vivo.

The term "patient," or "subject" as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "expression cassette" refers to a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or anti sense direction. The expression cassette comprising the nucleotide sequence of interest may be chimeric, meaning that at least one of its components is heterologous with respect to at least one of its other components. The peptides of the invention of the present invention may be chimeric.

The expression cassette may also be one which is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus.

As used herein, a promoter region or promoter element refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

To accomplish delivery of RNA to target cells, the methods and compositions of the present invention comprise *Saccharomyces*-generated extracellular vesicles (SGEVs). The term extracellular vesicles are membranous vesicles released from cells. The extracellular vesicles of the methods and compositions of the invention are composed of lipid bilayers that can envelope and carry cargo in its interior. The lipid bilayer of the EVs may also include proteins embedded therein. In some embodiments, the SGEVs of the compositions and methods of the present invention can be exosomes or ectosomes. As is well-known, exosomes are generally formed upon the endocytosis of multivesicular endosomes (MVEs) to form intraluminal vesicles (ILVs) which are subsequently released into the extracellular environment as exosomes, whereas ectosomes are assembled and released from the plasma membrane. Often, the primary structural feature distinguishing ectosomes and ectosomes is diameter. In some embodiments, the diameter of the SGEVs are between about 30 nm to about 180 nm, between about 50 nm to about 200 nm, between about 75 nm to about 250 nm, between about 100 nm to about 300 nm, between about 125 nm to about 350 nm, between about 150 nm to about 400 nm, between about 175 nm to about 450 nm, between about 200 nm to about 500 nm, between about 250 nm to about 550 nm, between about 300 nm to about 600 nm, between about 350 nm to about between about 650 nm, between about 400 nm to about 700 nm, between about 450 nm to about 750 nm, between about 500 to about 800 nm, between about 550 nm to about 850 nm, between about 600 nm to about 900 nm, between about 650 nm to about 950 nm, between about 700 nm to about 1000 nm, between about 750 nm to about 1050 nm, between about 800 nm to about 1100 nm, between about 850 nm to about 1150 nm or between about 900 nm to about 1200 nm. Thus, exosomes may comprise components on their membrane surface, including but not limited to proteins, glycoproteins, proteoglycans, carbohydrates and lipids, which may be used to direct cargo into to exosome.

For example, the SGEVs of the present invention may comprise one or more protein embedded in the lipid bilayer, such as but not limited to (a) ammonia transport outward protein 2 (SEQ ID NO. 24) (UniProt Database Accession No. P32907, which is hereby incorporated by reference), (b) plasma membrane protein up-regulated during nitrogen stress protein 1 (SEQ ID NO. 25) (UniProt Database Accession No. Q06991, which is hereby incorporated by reference), (c) glucan 1,3-beta-glucosidase 1/11 (SEQ ID NO. 26) (UniProt Database Accession No. P23776, which is hereby incorporated by reference), (d) glucan 1,3-beta-glucosidase (SEQ ID NO. 27) (UniProt Database Accession No. P15703, which is hereby incorporated by reference), (e) 1,3-beta-glucanosyltransferase (SEQ ID NO. 28) (UniProt Database Accession No. P22146, which is hereby incorporated by reference), (f) 1,3-beta-glucanosyltransferase (SEQ ID NO. 29) (UniProt Database Accession No. Q08913, which is hereby incorporated by reference), (g) iron transport multicopper oxidase (SEQ ID NO. 30) (UniProt Database Accession No. P38993, which is hereby incorporated by reference), (h) probable glycosidase protein (SEQ ID NO. 31) (UniProt Database Accession No. P53301, which is hereby incorporated by reference), (i) non-classical export protein 1 (SEQ ID NO. 31) (UniProt Database Accession No. Q02820, which is hereby incorporated by reference) and (j) Sur7 protein (SEQ ID NO. 33) (UniProt Database Accession No. P54003, which is hereby incorporated by reference).

In some embodiments, any one or more of the proteins of (a)-(j) above can serve as an anchor protein within the lipid bilayer membrane of the SGEV. As used herein, an anchor protein is a protein embedded in the membrane of the SGEV such that at least a portion of the protein is exposed to the extravesicular environment. In some embodiments, the anchor protein a protein normally found in SGEVs. In some embodiments, the anchor protein will have another protein domain bound or linked thereto. Thus, the anchor protein can form a complex that can present a protein or protein domain on the membrane surface. In one embodiment, the protein or protein domain linked or bound to the anchor protein is a foreign protein. As used herein, a foreign protein is a protein or portion thereof that the specific species of *Saccharomyces* used to generate the SGEVs does not normally express. For example, the foreign protein may be a full length mammalian proteins or only a portion thereof.

Examples of proteins or portions thereof that may be used as the foreign protein in the foreign protein-anchor protein complex (FPAPC) include human angiotensin I or a portion thereof that binds to angiotensin converting enzyme II (ACE2) (SEQ ID NO. 34), angiotensin II or a portion thereof that binds to ACE2, Transmembrane protease, serine 2 (TMPRSS2) (SEQ ID NO. 37) or a portion thereof that binds to ACE2, vascular endothelial growth factor A (VEGF-A) (SEQ ID NO. 36) or a portion thereof that binds to neuropilin-1 (NRP1) (SEQ ID NO. 35), or any CendR peptide that binds to NRP1. The term CendR peptide is well understood in the art and, in this instance, means a peptide that binds to NRP1 with a (-terminal amino acid sequence of R/KXXR/K. Examples of CendR peptides include but are not limited to the peptide sequence RPARPAR and those disclosed in Teesalu T, et al., *Proc. Nat'l. Acad. Sci. USA,* 106(38): 16157-62 (2009) (doi:10.1073/pnas.0908201106), which is incorporated by reference. Other examples of foreign proteins include synthetic proteins or polypeptides. As used herein the terms polypeptide and protein are used interchangeably.

The foreign protein(s) in the FPAPC will bind to a target surface molecule (receptor) displayed on a target cell. As used herein, the term "target surface molecule" is the molecule, e.g., a protein, which is the binding partner to the foreign protein in the FPAPC. In one embodiment, the target surface molecule is a mammalian cell surface protein. Examples of mammalian cell surface proteins include but are not limited to a receptor, an enzyme, an antigen expressed on an immune cell, an antigen expressed on an immune effector cell, a peptide, and an antigen. For example, the target surface molecule may be ACE2 or NRP1. The identity of the target surface molecule will dictate the identity of the foreign protein used in the FPAPC. For example, if the target surface molecule is ACE2, then the foreign protein of the FPAPC may be angiotensin II or a portion or mimetic thereof that binds to ACE2. Similarly, if the target surface molecule is NRP1, then the foreign protein of the FPAPC may be VEGF-A, or a portion or mimetic thereof that binds to NRP1.

Other target surface molecules that may be used to determine the identity of the foreign protein in the FPAPC include but are not limited to TMPRSS2 or Adam17. The term target cell, as used herein, is a cell that expresses the target surface molecule on its cell surface. Thus, a target cell is not necessarily a cell type, but rather a target cell as used herein is determined by the cell surface protein it displays. The target cell may be engineered to express the target surface protein or the target cell may naturally express the target surface protein.

The foreign peptide in the FPAPC may be a peptide mimetic that binds to a membrane protein displayed on a cell surface. A peptide mimetic is used herein as it is in the art. Namely, peptide mimetics are peptides that mimic the binding portion of ligands of hormones, enzymes, receptors, cytokines or other molecules such that the mimetic can bind to a hormone, enzyme, receptor, cytokine etc. The mimetic may be a smaller portion of the full length protein that is responsible for the ligand binding to its binding partner, or the mimetic may be a synthetic molecule whose three dimensional structure can fit into, and possibly bind to, the binding pocket of the naturally occurring ligand's binding partner.

Examples of peptide mimetics that can be used as the foreign protein in the FPAPC include but are not limited to mimetics of angiotensin I, mimetics of angiotensin II, mimetics of VEGF-A and mimetics of the ACE2 binding domain of TMPRSS2. In specific embodiments, the mimetic that is the foreign protein in the FPAPC is at least one of the peptides selected from the amino acid sequences listed in Table II of Huang, L., et al., *J. Biol. Chem.,* 278(18):15532-15540 (2003), which is incorporated by reference. The peptide fragments or mimetics need not have any activity in inhibiting the target surface molecule, provided that the foreign peptide binds with at least some specificity. In specific examples, the mimetic is an angiotensin mimicking peptide with amino acid sequence of GDYSHCSPL-RYYPWWKCTYPDPEGGG (SEQ ID NO. 14) or GDDDDCGWIGFANFHLCLHGDPEGGG (SEQ ID NO. 15).

Methods of generating amino acid sequences that, when produced, can serve as peptide mimetics are well-known in the art. In one embodiment, computer modeling can be employed to design and identify peptides, and even small molecules, that can fit into a binding pocket of the target surface molecule. For example, Farhadi, T. and Hashemian, S., *Drug Des. Devel. Ther.,* 12:1239-1254 (2018), which is incorporated by reference, provides a review of current computer modeling methods that can be employed to generate putative peptide mimetics that can be used as the foreign protein in the FPAPC. Other methods of designing peptide mimetics include determining the region of binding between a ligand and its binding partner and shortening the full length ligand and/or mutating, e.g., alanine scanning, to determine the identities of amino acid identity that contribute to binding.

In one embodiment, the FPAPC is a fusion protein. The term fusion protein as used herein is used as it is in the art. Namely, the fusion proteins used in the methods and compositions of the present invention involve two separate proteins or protein domains that are linked by a covalent bond. In one embodiment, the covalent bond linking the two domains is an amine bond. In more specific embodiments, the anchor protein and the foreign protein is a fusion protein comprising a single-chain polypeptide. In even more specific embodiments, the single-chain polypeptide comprising the anchor protein and the foreign protein further comprises a linker peptide sequence. Any linker sequence can be used to covalently link the anchor protein and the foreign protein.

As used herein, the term "peptide linker(s)," "linker(s)," or "linker moiety" refers to a peptide or polypeptide sequence, e.g., a synthetic peptide or polypeptide sequence, which connects two domains in a linear amino acid sequence of a polypeptide chain. In one embodiment, the polypeptides of invention are encoded by nucleic acid molecules that encode peptide linkers which either directly or indirectly connect the anchor protein and foreign protein which make up the construct. These linkers may be interposed between the anchor protein and foreign protein. If the linker connects two protein moieties contiguously in the linear polypeptide sequence, it is referred to as a "direct" linkage. In contrast, the linkers may link the first protein moiety, i.e., anchor protein or foreign protein, to a binding moiety which is, in turn, linked to the second protein moiety, i.e., anchor protein or foreign protein, thereby forming an indirect linkage. Linkers are typically located at the N or C terminus of the protein moieties.

In one embodiment, the linker linking the anchor protein and the foreign protein is a peptide comprised of glycine (Gly)n, wherein n is an integer that is the same or higher than 1, 2, 3, 4, 5, 6, 7, 8, 9, 10. In another embodiment, the linker linking the anchor protein and the foreign protein is a gly-ser linker. As used herein, the term "gly-ser peptide linker" (GS) refers to a peptide comprising or consisting of glycine (G or Gly) and serine (S or Ser) residues. Exemplary gly-ser peptide linkers comprise the amino acid sequence (Gly4 Ser)n or (Gly3 Ser)n. Another exemplary gly-ser peptide linker comprises the amino acid sequence S(Gly4 Ser)n wherein n is an integer that is the same or higher than 1, 2, 3, 4, 5, 6, 7, 8, 9, 10. In another embodiment, the linker linking the anchor protein and the foreign protein is a peptide comprising the sequence of GSAGSAAGSGEF (SEQ ID NO. 16).

The extracellular vesicles are generated from *Saccharomyces*. *Saccharomyces* is a single-celled organism, but the term "extracellular vesicle," as it relates to the SGEVs, refers to vesicles that are secreted from *Saccharomyces* into the local environment, such as, but not limited to cell culture medium and organisms that may have ingested or consumed or been administered the *Saccharomyces* secreting the vesicles containing the foreign RNA. In one embodiment, the SGEVs are secreted from *Saccharomyces cerevisiae* or *Saccharomyces boullardii*.

The *Saccharomyces* are engineered to produce EVs that contain FPAPC such that the foreign protein in the FPAPC is on the exterior side of the vesicle. The foreign protein is to be complexed with an anchor protein. The anchor proteins, as disclosed herein, will derive from the species of *Saccharomyces* used. Thus, the term "*Saccharomyces*-derived" as used herein means that at least one of the anchor proteins within the EVs used in the compositions and methods of the present invention are normally expressed in *Saccharomyces*. In one embodiment, at least one of the anchor proteins of the SGEVs used in the methods and compositions of the present invention are normally expressed in *Saccharomyces cerevisiae* or *Saccharomyces boullardii*. One of skill in the art can determine the source of the anchor protein, generally speaking, by its amino acid sequence. For example, if a specific anchor protein has an amino acid sequence of a *Saccharomyces boullardii* anchor protein, then the SGEV would be "derived" *Saccharomyces boullardii*. In some instances, the amino acid sequence of the anchor proteins are from the same species. In other instances, the amino acid sequence of the anchor proteins are from the different species, but the anchor proteins should all be from within the *Saccharomyces* genera. To be clear, if the EVs used in the methods and compositions of the present invention contain proteins that are not from any *Saccharomyces* species, the EV could still be considered an SGEV if those non-*Saccharomyces* proteins are not used as anchor proteins to form a complex with a foreign protein in the FPAPC.

The SGEVs used in the methods and compositions of the present invention may or may not also comprise a detectable signal. The signal can be complexed with a protein within the SGEVs, or the signal can be within the interior of the SGEV. In one embodiment, the detectable signal is a green fluorescent protein (GFP).

The SGEVs are to be employed in methods of silencing target genes. In select embodiments, the invention relates to methods of gene silencing comprising administering the SGEVs of the present invention, comprising foreign RNA, to a cell or population of cells that express a target gene. The SGEVs can deliver their foreign RNA cargo, comprising a nucleotide sequence that targets a target gene for silencing, to the target cells, thereby silencing the target gene.

As used herein, a target gene is a gene whose expression is to be selectively inhibited or "silenced." This silencing is achieved by promoting the degradation of the mRNA of the target gene that is induced by the binding between the delivered RNA, e.g., a shRNA, miRNA, siRNA, and the mRNA of the target gene. One portion or segment of these molecules is an anti-sense strand that is substantially complementary to a portion, e.g., about 16 to about 40 or more nucleotides of the mRNA of the target gene. Any gene previously identified by genetics or by sequencing may represent a target. Target genes may include, viral structural genes, such as but not limited to, capsid proteins, envelope proteins and membrane fusion proteins, viral non-structural genes such as but not limited to, virus replicon genes and virus immunomodulatory genes, viral regulatory and/or accessory genes. Other target genes include nuclear-encoded developmental genes and regulatory genes as well as metabolic or structural genes or genes encoding enzymes. In one embodiment of the present invention, the gene to which the delivered RNA is targeting for silencing is a viral gene that is necessary for virus replication.

As used herein, the gene silencing need not be a complete silencing. In one embodiment, the silencing is a "complete" silencing in that the gene expression is completely suppressed such that there is no detectable expression of the target gene. In other embodiments, the silencing is not a complete silencing and, instead, the silencing is partial. A partial gene silencing means a reduction in expression of the target gene such that expression may still be detectable. A reduction of gene expression can be assessed by determining gene expression levels before and after treatment or administration of the SGEVs. Gene expression levels can be measured using well-known methods, including but not limited to, measuring protein expression levels of the target gene and measuring mRNA levels of the target gene. Measuring protein expression levels can be accomplished directly, e.g., Western Blot, ELISA, etc. or indirectly, e.g., protein activity, metabolite levels, etc. In one embodiment, gene expression levels are measured with "RNA-seq," which is a well-known methodology for RNA profiling. See Wang, Z., et al., *Nat Rev Genet.*, 10(1): 57-63 (2009), which is incorporated by reference. The levels of gene expression of a target gene in a cell or group of cells can be measured prior to administration of the SGEVs by culturing the cells and measuring gene expression levels from the cells in culture. Then the SGEVs can be administered to the cells in culture and target gene expression levels can be reassessed to determine changes in gene expression levels.

The term "administering" as used herein means that the SGEVs are brought into contact or the same environment as the target cells. For example, if the SGEVs are administered to a subject having or suspected of having a viral infection, the SGEVs may be administered to the subject by a routine route of administration, such as but not limited to, oral, intravenous, topical, intraperitoneal, intramuscular, subcutaneous, intranasal or intradermal route. If the SGEVs are administered to cells in culture, for example to assess differential gene expression levels, the SGEVs can be added to the culture medium.

In more specific embodiments, the target gene against which the delivered RNA is directed is selected from the group consisting of the ORF1ab, ORF3a, ORF7a, ORF8, S protein, N protein, the RdRp protein or M protein ORF, or the 5'-nsp1 region or S'UTR region of SARS-CoV-2. In more specific embodiments, the delivered RNA comprises a nucleotide sequence of between about 20 to about 100 contiguous nucleotides of the ORF1ab, ORF3a, ORF7a, ORF8, S protein, N protein, the RdRp protein or M protein ORF, or the 5'-nsp1 region or S'UTR region of SARS-CoV-2.

The present invention also relates to polynucleotides encoding the fusion proteins of the present invention. As is known in the art, for any DNA sequence determined by an automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the peptides may be identical to the coding sequence shown in the sequence listing, or that of any of the deposited clones, or may be a different coding sequence which, as a result of the redundancy or degeneracy of the genetic code, encodes the same fusion proteins as shown in the sequence listing.

The term "polynucleotide encoding a peptide" encompasses a polynucleotide which includes only coding sequences for the polypeptide, e.g., fusion protein, as well as a polynucleotide which includes additional coding and/or non-coding sequences. Thus, for example, the polynucleotides of the present invention may encode for a peptide, e.g., a fusion protein, or for a peptide having a prosequence or for a protein having both a prosequence and presequence.

The polynucleotides of the present invention may also have the coding sequence fused in frame to, for example, a marker sequence which allows for identification of the polypeptide of the present invention. The marker sequence may be a GFP protein, a hexa-histidine tag to provide for purification of the fusion protein is used.

The invention also relates to vectors, including but not limited to, expression vectors comprising the polynucleotides encoding the fusion proteins of the present invention. Types of vectors for expression for proteins and fusion proteins are well known in the art. In one embodiment, the vector is an expression vector for protein expression in *Saccharomyces*. Yeast expression vectors are commercially available from manufacturers.

The present invention also relates to methods of making and using these *Saccharomyces*-generated EVs. In one embodiment, the methods of making the SGEVs of the present invention comprise introducing into the *Saccharomyces* the expression vector encoding a fusion protein of the present invention to generate a host *Saccharomyces* cell. The host cell is then cultured under conditions to permit protein production from the vector encoding the fusion protein. In one embodiment, the host cells of the present invention *Saccharomyces cerevisiae* or *Saccharomyces boullardii*.

Culture conditions for culturing yeast host cells are well-known in the art. The continued culture of the host cell will permit production and secretion of the SGEVs into the cell culture environment, where they can be isolated from culture.

Methods of isolating extracellular vesicles, such as exosomes, from cell culture media are well-known in the art and are reviewed in Li, P. et al., *Theranostics*, 7(3):789-804 (2017), which is incorporated by reference herein. Generally speaking, methods of isolating the SGEVs from culture include but are not limited to ultracentrifugation methods, size-based exclusion methods, immunoaffinity capture-based methods, precipitation methods, microfluidics-based methods or some combination thereof.

The foreign RNA may or may not be present in the SGEVs immediately isolated from culture. For example, the foreign RNA can be introduced into the SGEVs by a number of different techniques. In select embodiments, the SGEVs are loaded with the foreign RNA by electroporation or the use of a transfection reagent. Extrapolation of the voltages used for electroporation of cells to take into account the size of the exosomes would suggest that excessively high voltages would be required for electroporation of exosomes. Surprisingly however, it is possible to use electroporation to load exosomes with RNA using voltages in the range of between about 20 V/cm to 1000 V/cm, for example 20 V/cm to 100 V/cm, with capacitance between about 25 µF and about 250 µF, for example between 25 µF and 125 µF.

In an alternative aspect of the present invention, it is possible to load the SGEVs with the foreign RNA using transfection agents. Despite the small size of the exosomes, conventional transfection agents can be used for transfection of exosomes with genetic material. In some embodiments, transfection reagents for use in accordance with the present invention include cationic liposomes.

In still other embodiments, the *Saccharomyces* host cell harboring an expression vector encoding the fusion protein of the present invention will include at least a second expression vector. The second expression vector would comprise a coding sequence for the foreign RNA to be loaded into the SGEVs as cargo. In these embodiments, the host cell would comprise at least two vectors, one of which comprises a polynucleotide encoding at least the foreign protein portion of the FPAPC and a second vector comprising expressing the foreign RNA that will become the cargo within the SGEV. U.S. Pat. No. 10,174,338, which is incorporated by reference, discloses various expression vectors that can be used to carry and express the foreign RNA in yeast cells.

The present invention also relates to fusion proteins comprising a *Saccharomyces* extracellular vesicle anchor protein and a second peptide. The second peptide may be any one of the foreign proteins listed herein as part of the FPAPC. In some embodiments, the fusion protein comprises a linker peptide. In more specific embodiments, the linker in the fusion proteins are any of the linker peptides disclosed herein.

For example, the fusion proteins of the present invention may comprise one or more protein embedded in the lipid bilayer, such as but not limited to such as but not limited to(a) ammonia transport outward protein 2 (SEQ ID NO. 24) (UniProt Database Accession No. P32907, which is hereby incorporated by reference), (b) plasma membrane protein up-regulated during nitrogen stress protein 1 (SEQ ID NO. 25) (UniProt Database Accession No. Q06991, which is hereby incorpo-rated by reference), (c) glucan 1,3-beta-glucosidase 1/11 (SEQ ID NO. 26) (UniProt Database Accession No. P23776, which is hereby incorporated by reference), (d) glucan 1,3-beta-glucosidase (SEQ ID NO. 27) (UniProt Database Accession No. P15703, which is hereby incorporated by reference), (e) 1,3-beta-glucanosyl-transferase (SEQ ID NO. 28) (UniProt Database Accession No. P22146, which is hereby incorporated by reference), (f) 1,3-beta-glucanosyltransferase (SEQ ID NO. 29) (UniProt Data-base Accession No. Q08913, which is hereby incorporated by reference), (g) iron transport multicopper oxidase (SEQ ID NO. 30) (UniProt Database Accession No. P38993, which is hereby incorporated by reference), (h) probable glycosidase protein (SEQ ID NO. 31) (UniProt Database Accession No. P53301, which is hereby incorporated by reference), (i) non-classical export protein 1 (SEQ ID NO. 31) (UniProt Database Accession No. Q02820, which is hereby incorporated by reference) and (j) Sur7 pro-tein (SEQ ID NO. 33) (UniProt Database Accession No. P54003, which is hereby incorporated by reference).

In more specific embodiments, the second protein or protein domain linked or bound to the first protein is a foreign protein, as the term is used herein. For example, the foreign protein may be a full length mammalian protein or only a portion thereof. Examples of proteins or portions thereof that may be used as the second protein or protein domain of the fusion proteins include but are not limited to human angiotensin I, angiotensin II, vascular endothelial growth factor A (VEGF-A), mimetics of the ACE2 binding domain of TMPRSS2. Other examples of the second protein or proteins of the fusion proteins of the present invention include synthetic proteins or polypeptides.

Other examples of the second protein or proteins of the fusion proteins of the present invention include a mammalian cell surface protein ligand. Examples of mammalian cell surface proteins include but are not limited to a receptor, an enzyme, an antigen expressed on an immune cell, an antigen expressed on an immune effector cell, a peptide, and an antigen. For example, the mammalian cell surface protein may be angiotensin converting enzyme II (ACE2), neuro-pilin-1 (NRP1), TMPRSS2 or Adam17. The identity of the mammalian cell surface protein will dictate the identity of the second protein or protein domain used in the fusions proteins of the present invention. For example, the second protein or protein domain of the fusion proteins of the present invention may be angiotensin II or a fragment or mimetic thereof. Similarly, the second protein or protein domain of the fusion proteins of the present invention may be VEGF-A, or a fragment or mimetic thereof.

The present invention also relates to methods of administering the SGEVs to a subject. In one specific embodiment, the present invention relates to methods of treating subject having or suspected of having a virus infection by administering the SGEVs to the subject. The treatment methods comprise administering the SGEVs of the invention to a subject infected with or suspected of being infected with the virus, where the foreign RNA within the administered SGEVs comprises at least one nucleotide sequence that targets at least one of the viral genes for gene silencing. In one specific embodiment, the subject has or is suspected of having a SARS-CoV-2 virus infection.

As used herein, the methods include administering the SGEVs to the subject prior to a medical diagnosis of having a virus infection. The methods therefore include administering the SGEVs to the subject if the subject displays at least one symptom of a virus infection such as, but not limited to, fever, headache, body ache, dizziness, loss of sense of smell, loss of sense of taste, fatigue, chills, nausea, vomiting, diarrhea, loss of appetite, disorientation, rash, cough, sore throat, congestion, difficulty breathing and low blood oxygen levels, to name a few. Accordingly, the methods include administering the SGEVs of the present invention to a subject exhibiting one or more of these symptoms.

The present invention also provides methods of prophylaxis of a virus infection. These methods include administering the subject the SGEVs of the present invention before any symptoms of virus infection appear. Thus, the invention includes methods of preventing or reducing the likelihood of acquiring a virus infection by administering the SGEVs of the present invention to a subject prior to detecting any symptoms of the virus infection or being diagnosed with the virus infection.

When administration is for the purpose of treatment, the SGEVs are provided at, or after the onset of, a symptom or condition in need of treatment. The therapeutic administration of the SGEVs serves to attenuate any symptom or prevent additional symptoms from arising. When administration is for the purposes of preventing a condition from arising ("prophylactic administration"), the SGEVs are provided in advance of any visible or detectable symptom. The prophylactic administration of the SGEVs serves to attenuate subsequently arising symptoms or prevent or reduce the likelihood of symptoms from arising altogether. The route of administration of the SGEVs includes, but is not limited to, topical, transdermal, intranasal, rectal, oral, subcutaneous, intravenous, intraarterial, intramuscular, intraosseous, intraperitoneal, epidural and intrathecal as disclosed herein. In one example SGEV's may be derived or isolated from a GRAS and/or probiotic yeast cell, such as *Saccharomyces cerevisiae,* and preferably *Saccharomyces boullardii*. For example, *Saccharomyces boullardii* probiotics, releasing wild type exosomes, have been shown to diminish disease severity by reducing the expression of inflammatory cytokines and stimulating the expression of anti-inflammatory cytokines in multiple organs including the lungs and cardiovascular system. *Saccharomyces boullardii* cells also have low immunogenicity and positively modulate host immune response in the presence of additional antigens. Sb is well established for genetic manipulation which allows the present inventors to engineer the Sb strain for expression and loading of specific siRNAs in exosomes. Cultivation of Sb is fast, low-cost, and easy to scale up using established procedures. Finally, the lipids present in EVs are natural and thus not likely to be cytotoxic when used therapeutically unlike artificial lipids frequently used to package mRNA for vaccines In specific embodiments, the oral administration of the SGEVs include administering engineered yeast, producing the SGEVs, as a probiotic. As used herein, a probiotic is a microorganism, such as a bacteria or yeast, generally recognized as safe for human or animal consumption. The probiotics of the present invention may or may not have additional health benefits to the consumer. In specific embodiments of the present invention, the probiotics is a *Saccharomyces cerevisiae* or a *Saccharomyces boullardii*. For example, *Saccharomyces boullardii* probiotics, releasing wild type exosomes, have been shown to diminish disease severity by reducing the expression of inflammatory cytokines and stimulating the expression of anti-inflammatory cytokines in multiple organs including the lungs and cardiovascular system. *Saccharomyces boullardii* cells also have low immunogenicity and positively modulate host immune response in the presence of additional antigens. Sb is well established for genetic manipulation which allows the present inventors to engineer the Sb strain for expression and loading of specific siRNAs in exosomes. Finally, Cultivation of Sb is fast, low-cost, and easy to scale up using established procedures The probiotic used in the methods of administering will be engineered to produce the SGEVs of the present invention.

As used herein, the term "RNAi molecules" "interfering RNA molecules" or "interfering RNA" or RNA molecules configured to mediate RNA interference generally refers to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNAi molecules include dsRNAs such as siRNAs, miRNAs and shRNAs, sgRNA, CRISPR RNA (crRNs). In one embodiment, the RNA silencing agent is capable of inducing RNA interference. In another embodiment, the RNA silencing agent is capable of mediating translational repression. As used herein, an RNA molecule or even RNAi molecule may further encompass lincRNA molecules as well as lncRNA molecules.

In some embodiments of the invention, the nucleic acid agent is a double stranded RNA (dsRNA). As used herein the term "dsRNA" relates to two strands of anti-parallel polyribonucleic acids held together by base pairing. The two strands can be of identical length or of different lengths, provided there is enough sequence homology between the two strands that a double stranded structure is formed with at least 60%, 70% 80%, 90%, 95% or 100% complementary over the entire length. According to an embodiment of the invention, there are no overhangs for the dsRNA molecule. According to another embodiment of the invention, the dsRNA molecule comprises overhangs. According to other embodiments, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. It will be noted that the dsRNA can be defined in terms of the nucleic acid sequence of the DNA encoding the target gene transcript, and it is understood that a dsRNA sequence corresponding to the coding sequence of a gene comprises an RNA complement of the gene's coding sequence, or other sequence of the gene which is transcribed into RNA.

The inhibitory RNA sequence can be greater than 90% identical or even 100% identical, to the portion of the target gene transcript. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60 degrees C. hybridization for 12-hours; followed by washing). The length of the double-stranded nucleotide sequences complementary to the target gene transcript may be at least about 18, 19, 21, 25, 50, 100, 200, 300, 400, 491, 500, 550, 600, 650, 700, 750, 800, 900, 1000 or more bases. In some embodiments of the invention, the length of the double-stranded nucleotide sequence is approximately from about 18 to about 530, or longer, nucleotides in length.

The present teachings relate to various lengths of dsRNA, whereby the shorter version i.e., x is shorter or equals 50 bp (e.g., 17-50), is referred to as siRNA or miRNA. Longer dsRNA molecules of 51-600 are referred to herein as dsRNA, which can be further processed for siRNA molecules. According to some embodiments, the nucleic acid sequence of the dsRNA is greater than 15 base pairs in length. According to yet other embodiments, the nucleic acid sequence of the dsRNA is 19-25 base pairs in length, 30-100 base pairs in length, 100-250 base pairs in length or 100-500 base pairs in length. According to still other embodiments, the dsRNA is 500-800 base pairs in length, 700-800 base pairs in length, 300-600 base pairs in length, 350-500 base pairs in length or 400-450 base pairs in length. In some embodiments, the dsRNA is 400 base pairs in length. In some embodiments, the dsRNA is 750 base pairs in length.

The term "siRNA" refers to small inhibitory RNA duplexes (generally between 17-30 base pairs, but also longer e.g., 31-50 bp) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC. It has been found that position of the 3'-overhang influences potency of a siRNA and asymmetric duplexes having a 3'-overhang on the antisense strand are generally more potent than those with the 3'-overhang on the sense strand. This can be attributed to asymmetrical strand loading into RISC, as the opposite efficacy patterns are observed when targeting the antisense transcript.

In certain embodiments, dsRNA can come from 2 sources; one derived from gene transcripts generated from opposing gene promoters on opposite strands of the DNA and 2) from fold back hairpin structures produced from a single gene promoter but having internal complimentary. For example, strands of a double-stranded interfering RNA (e.g., a siRNA) may be connected to form a hairpin or stem-loop structure (e.g., a shRNA). Thus, as mentioned, the RNA silencing agent may also be a short hairpin RNA (shRNA). The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. It will be recognized by one of skill in the art that the resulting single chain oligonucleotide forms a stem-loop or hairpin structure comprising a double-stranded region capable of interacting with the RNAi machinery.

As used herein, the phrase "microRNA (also referred to herein interchangeably as "miRNA") or a precursor thereof" refers to a microRNA (miRNA) molecule acting as a post-transcriptional regulator. Typically, the miRNA molecules are RNA molecules of about 20 to 22 nucleotides in length which can be loaded into a RISC complex and which direct the cleavage of another RNA molecule, wherein the other RNA molecule comprises a nucleotide sequence, essentially complementary to the nucleotide sequence of the miRNA molecule. Typically, a miRNA molecule is processed from a "pre-miRNA," or as used herein, a precursor of a pre-miRNA molecule by proteins, such as DCL proteins, and loaded onto a RISC complex where it can guide the cleavage of the target RNA molecules. Pre-microRNA molecules are typically processed from pri-microRNA molecules (primary transcripts). The single stranded RNA segments flanking the pre-microRNA are important for processing of the pri-miRNA into the pre-miRNA. The cleavage site appears to be determined by the distance from the stem-ssRNA junction (Han et al. 2006, Cell 125, 887-901, 887-901).

As used herein, a "pre-miRNA" molecule is an RNA molecule of about 100 to about 200 nucleotides, preferably about 100 to about 130 nucleotides, which can adopt a secondary structure comprising an imperfect double stranded RNA stem and a single stranded RNA loop (also referred to as "hairpin"), and further comprising the nucleotide sequence of the miRNA (and its complement sequence) in the double stranded RNA stem. According to a specific embodiment, the miRNA and its complement are located about 10 to about 20 nucleotides from the free ends of the miRNA double stranded RNA stem. The length and sequence of the single stranded loop region are not critical and may vary considerably, e.g., between 30 and 50 nucleotides in length. The complementarity between the miRNA and its complement need not be perfect, and about 1 to 3 bulges of unpaired nucleotides can be tolerated. The secondary structure adopted by an RNA molecule can be predicted by computer algorithms conventional in the art such as mFOLD. The particular strand of the double stranded RNA stem from the pre-miRNA which is released by DCL activity and loaded onto the RISC complex is determined by the degree of complementarity at the 5' end, whereby the strand, which at its 5' end, is the least involved in hydrogen bonding between the nucleotides of the different strands of the cleaved dsRNA stem, is loaded onto the RISC complex and will determine the sequence specificity of the target RNA molecule degradation. However, if empirically the miRNA molecule from a particular synthetic pre-miRNA molecule is not functional (because the "wrong" strand is loaded on the RISC complex), it will be immediately evident that this problem can be solved by exchanging the position of the miRNA molecule and its complement on the respective strands of the dsRNA stem of the pre-miRNA molecule. As is known in the art, binding between A and U involving two hydrogen bonds, or G and U involving two hydrogen bonds is less strong that between G and C involving three hydrogen bonds.

Naturally occurring miRNA molecules may be comprised within their naturally occurring pre-miRNA molecules, but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds. Some pre-miRNA scaffolds may be preferred over others for their efficiency to be correctly processed into the designed microRNAs, particularly when expressed as a chimeric gene wherein other DNA regions, such as untranslated leader sequences or transcription termination and polyadenylation regions are incorporated in the primary transcript in addition to the pre-microRNA.

According to the present teachings, the dsRNA molecules may be naturally occurring or synthetic. The dsRNA can be a mixture of long and short dsRNA molecules such as, dsRNA, siRNA, siRNA+dsRNA, siRNA+miRNA, or a combination of same.

In a preferred embodiment, one or more nucleic acid agents are designed for specifically targeting a target gene of interest. It will be appreciated that the nucleic acid agent can be used to downregulate one or more target genes (e.g., as described in detail above). If a number of target genes are targeted, a heterogenic composition which comprises a plurality of nucleic acid agents for targeting a number of target genes is used. Alternatively, the plurality of nucleic acid agents is separately formulated. According to a specific embodiment, a number of distinct nucleic acid agent molecules for a single target are used, which may be used separately or simultaneously (i.e., co-formulation) applied.

For example, in order to silence the expression of an mRNA of interest, synthesis of the dsRNA suitable for use with some embodiments of the invention can be selected as follows. First, the mRNA sequence is scanned including the 3' UTR and the 5' UTR. Second, the mRNA sequence is compared to an appropriate genomic database using any sequence alignment software, such as the BLAST software available from the NCBI server (wwwdotncbidotnlmdotnih-dotgov/BLAST/). Putative regions in the mRNA sequence which exhibit significant homology to other coding sequences are filtered out. Qualifying target sequences are selected as templates for dsRNA synthesis. Preferred sequences are those that have as little homology to other genes in the genome to reduce an "off-target" effect. It will be appreciated that the RNA silencing agent of some embodiments of the invention need not be limited to those molecules containing only RNA, but further encompasses chemically-modified nucleotides and non-nucleotides.

The terms "comprises", "comprising", are intended to have the broad meaning ascribed to them in U.S. Patent Law and can mean "includes", "including" and the like.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims.

EXAMPLES

Example 1: Rationale for SGEVs as Anti-Viral Therapeutic Platform

Mammals, and in particular humans are constantly exposed to viruses that can lead to substantial disease burden, morbidity, and potentially mortality. The mutations of known viruses, such as the Delta and Omicron variants of the SARS-CoV-2 coronavirus, and arising of new viruses from zoonotic sources present a constant threat of epidemics and pandemics and a never-ending challenge to medicine. Unlike bacterial diseases, which generally can be treated with antibiotics, so far there is no common approach for fighting viral diseases. As SARS-CoV-2 coronavirus pandemic has demonstrated, the development of efficient treatment for new viruses could take months or years of medical struggle while the virus takes its toll on human lives and the world economy. As noted above, RNA interference is a mechanism of regulation of gene expression by blocking and disruption mRNA molecules mediated by small (19-27 bp) siRNA specifically complimentary to targeted mRNA sequence. Antiviral action of exogenous siRNA was demonstrated for broad range of both RNA and DNA viruses (for review see Levanova et al, 2018 (incorporated herein by reference)). As such, siRNA technology has potential to become a universal approach for anti-viral therapy.

The bottleneck of siRNA technology is the challenge of delivery of siRNA to targeted cells. Generally, siRNA molecules are not very stable itself and could be easily digested by extracellular nucleases. Also, despite of small size of siRNA molecules, electrostatic repulsion prevents their passive diffusion through cell membranes which brings in the necessity to encapsulate siRNA for protection of its integrity and improving membrane penetration. Two main types of vesicles currently used for siRNA encapsulation are chemically synthesized nanoparticles (proteins based or liposomes) or naturally occurring extracellular vesicles aka exosomes derived from mammalian cells. Both methods are expensive, there are concerns regarding administration of frequent and large doses of artificial lipids, and scaling up mammalian exosomes production is problematic. The cost of drug production could be potential roadblock for creating therapeutics for treatment of viral infection since such drugs need to be produced in high quantity to meet the needs of the market.

In one embodiment, the present invention addresses these technical hurdles by engineering a yeast, and preferably a Sb strain producing exosomes carrying anti-viral siRNA. Such yeast strain(s) can be grown in fermenters allowing easy and inexpensive commercial production of exosomes for pharmaceutical use, that could further be used as broad platform for siRNA delivery for silencing replication of viruses as well host genes expression in the range of pathological conditions such as inflammation, cancer or auto-immune diseases.

While considerable efforts to develop a drug delivery system employing EVs is currently being pursued, most of the work is on vesicles derived from human cells, especially EVs from macrophages or mesenchymal stem cells. Cultivation of mammalian cells for EVs requires the use of expensive growth media and serums and sometimes special, sophisticated techniques such as 3D-cell culturing. On the other hand, growing yeast is low-cost, simple, and fast: the average time for division of mammalian cells is more than 24 hours, while yeast double their population approximately every 90 minutes. Furthermore, human cells have the potential to introduce human pathogens which cannot grow in yeast.

Extracellular vesicles must be safe for injection into humans, which means their administration should not induce any adverse reactions such as inflammation or a strong immune response. In certain embodiment, the use of Sb as a source of EVs source organism as there is evidence of it being safe for humans in the prior art. Sb has also been used as a probiotic for decades, and it is currently approved by the FDA as a Generally Recognized As Safe (GRAS) microorganism. Oral administration of Sb has demonstrated clinical effectiveness in treatment of many gastrointestinal diseases both inflammatory, such as IBD or Crohn's disease, or infectious, such as *Clostridium difficile* or *E. coli* infections (review Kelesidis T, Pothoulakis C, 2012). Moreover, the positive effect of Sb is not limited by local responses on intestinal surfaces but has a systemic beneficial effect on the organism level. Sb administration prevents tissue damage and decreases inflammation in hosts by down-regulating the production of pro-inflammatory while up-regulating anti-inflammatory cytokines (Fidan et al, 2009; Duman et al, 2013; Durmaz et al, 2020).

Specifically, the protective effect of Sb pretreatment was demonstrated in an experimental model of lung injury in rats (Karen et al, 2010) and for a cardiovascular system in a diabetic mice model (Brandalo et al, 2018). Additionally, Sb also has unique immunomodulatory properties. While Sb itself has low immunogenicity and doesn't induce significant production of antibodies recognizing Sb antigens (Hudson et al, 2016; Joossens, 2005), the presence of Sb stimulates an immune response to pathogens. For example, in experiments an oral administration of Sb significantly increased specific antibody production in mice infected by *Clostridium difficile* (Bagherpour et al, 2016), and increased antibody production in response to a vaccination against leptospirosis (Silveira et al, 2014). Sb cells routinely shed EVs into the environment, so subjects exposed to Sb are simultaneously exposed to Sb-derived EVs as well. As such, administration of Sb-derived EVs can be safe and have as low immunogenicity as the administration of Sb itself. Moreover, EV-based treatments and therapeutics are not susceptible to antibiotic resistance due to their unique mode of action. This allows wide-spread deployment of the invention without the negative potential of developing strains of antibiotic resistant pathogens.

Unlike EVs derived from mammalian cells, engineering of yeast EVs has yet to be systematically explored and a few important gaps need to be filled to use yeast EVs as vesicles for therapeutic delivery. To close these gaps, present inventors established a siRNA expression system in Sb cells for the synthesis of therapeutic siRNA and packing them into EVs.

Example 2: Characterization of Sb-Derived EVs

EVs were isolated via ultracentrifugation from 1 L of Sb culture grown in flask for 24 h and resuspended in 1 ml of phosphate-buffered saline (PBS). The size distribution and number of EVs were determined using nanoparticle tracking analysis (NTA) on a ZetaView instrument. Typical yields of EVs obtained from single extraction were approximately $3 \times 10^{11}$ with median size of particles 125 nm, StDev 70 nm (FIG. 1) and zeta potential about −15 mV.

Example 3: Establishment of siRNA Expressing System in Sb

Figure 2A:
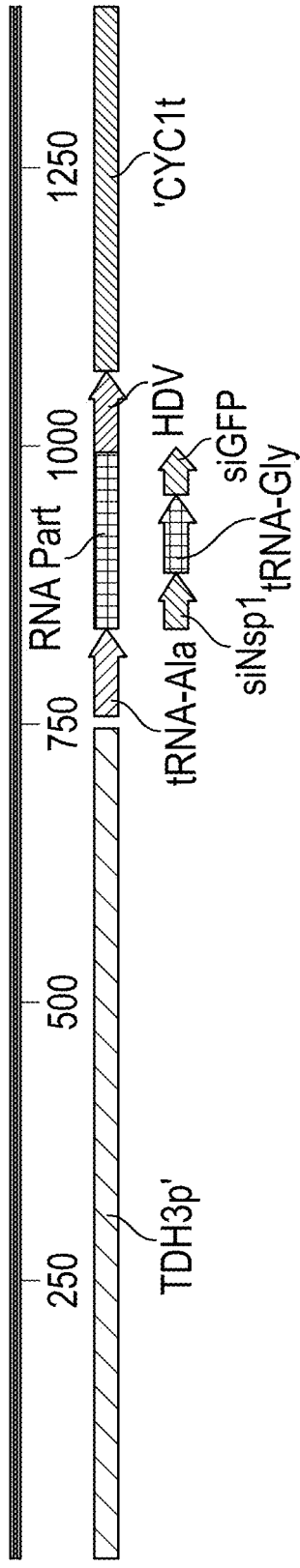
FIGS. 2A-B. show Pol-II (A) and Pol-I (B) cassettes for expression of shRNA targeting Nsp1 gene of SARS-CoV-2 (siNsp) and eGFP (siGFP).
Figure 2B:
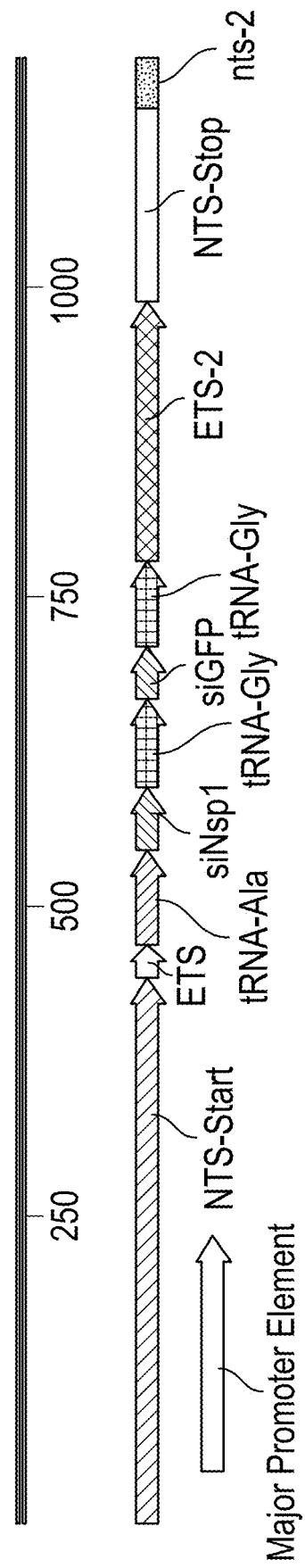

Sb doesn't have its own RNAi machinery including proteins of the RISC complex such as dicer or argounate. Though some miRNA-like structures were found in Sb by RNA sequencing, the general mechanism of small RNA processing in Sb is unclear. To express siRNA of pre-defined size in Sb cells the present inventors designed integration cassettes where shRNA were expressed either under RNA polymerase II type TDH3 promoter (FIG. 2A), or under control of RNA polymerase I rRNA promoter (FIG. 2B). Both expression cassettes contained two siRNAs flanked with tRNAs or tRNA and ribozyme HDV. Post-transcriptional processing of tRNA by yeast RNases P and Z or auto-cleavage of HDV ribozyme leads to removal of flanking sequences and separation of single small RNAs (Zhang et al, 2019). This approach also allowed the present inventors to engineer Sb expressing pool of siRNAs for simultaneous targeting more than one locus in viral genomes. Expression cassettes used in this work contained two short hairpin RNA (shRNA), one targeting Nsp1 gene from SARS-CoV-2 genome (SEQ ID NO. 1, and 18), and second targeting eGFP gene (SEQ ID NO. 1, and 18). ShRNA expression cassettes were genome integrated in YPRCt3 locus on XVI chromosome. It was previously shown that integration at this locus doesn't affect the cell growth and gene expression in *S. boulardii* (Durmusoglu et al, 2020)

Figure 3:
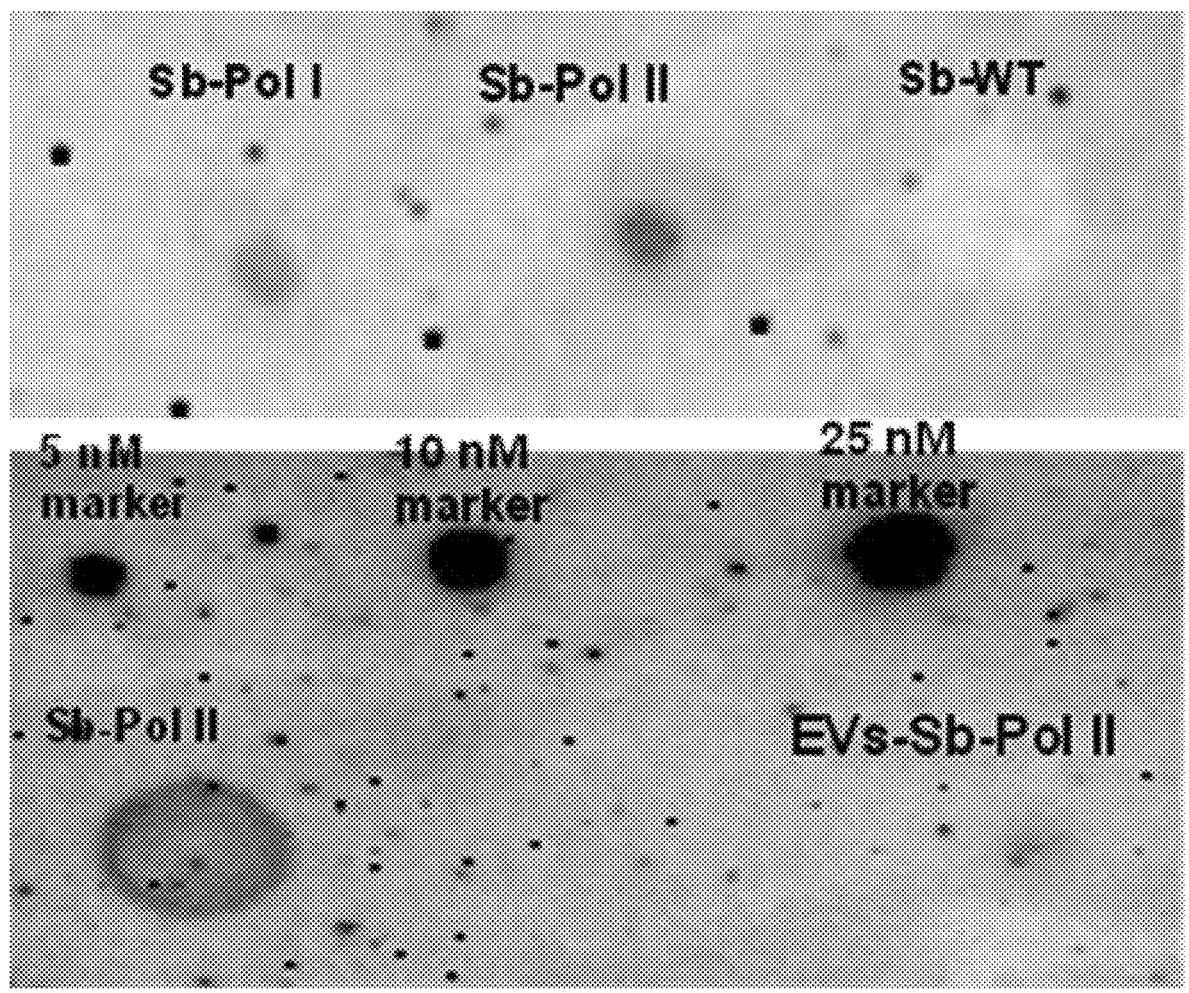
FIG. 3. shows expression of sh around 50% to 52%. Other characteristics of the siRNA sequence that is delivered to the target cells may or may not include those characteristics noted in Naito, Y. and Ui-Tei, K., *Front. Genet., Vol* 3, Article 102 (2012).

To demonstrate that engineered Sb cells indeed express shRNA, the present inventors extracted total RNA from wild-type and engineered Sb cells, and performed northern dot blot analysis using an RNA probe sequence-specific to the yeast expressed shRNA-Nsp1 (FIG. 3). ShRNA-Nsp1 was detected in both SB strains using RNA pol I and RNA pol II expression cassettes as well as in EVs fraction extracted from engineered Sb, but not in wild type Sb cells.

Example 3: Verification of Cellular Uptake of Sb-Derived EVs

Figure 4:
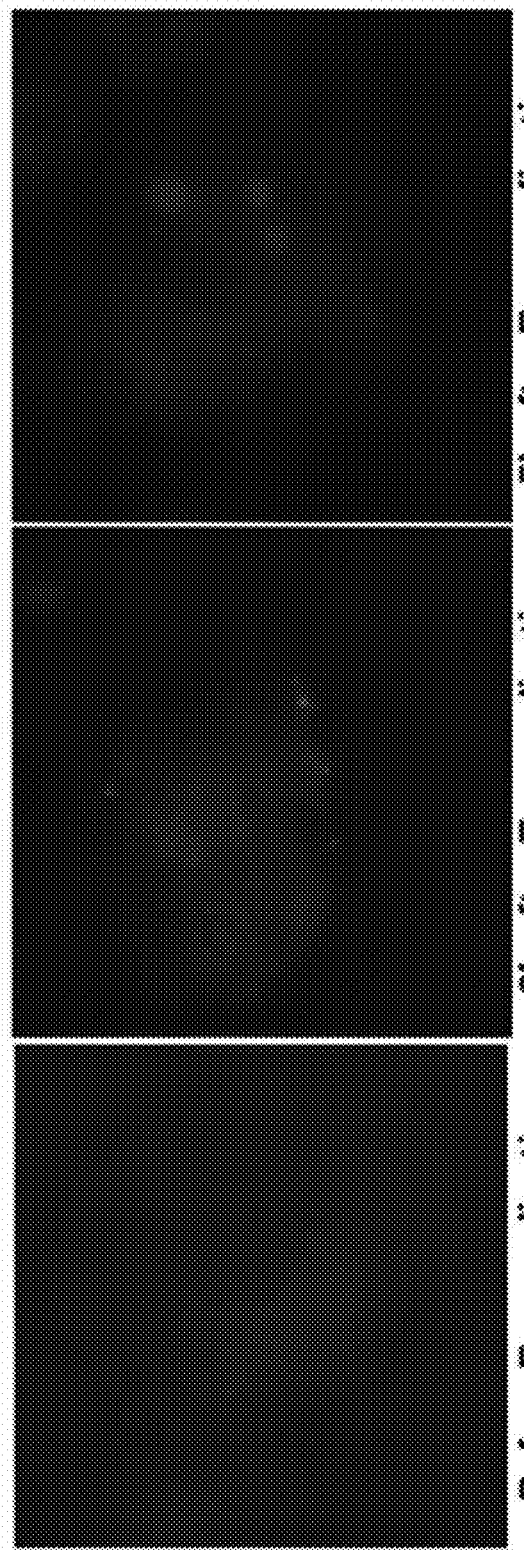

Cellular uptake of different yeast-derived EVs has been previously demonstrated (for review Rizzo, Rodrigues and Janbon, 2020). To verify that Sb-derived EVs also could be utilized by human cells, the present inventors extracted EVs from engineered Sb strain expressing Sur7 protein localized in EVs and fused with GFP reporter gene, and applied these EVs to H1299 cells. The presence of GFP labeled protein allowed us to visualize the localization of EVs. Following the application of the EVs, we observed the presence of GFP signals in H1299 cells and the spread of fluorescence in cytoplasm and endosomes-like structures, which demonstrates that EVs are indeed being absorbed and degraded by human cancer lung cells (FIG. 4).

Example 4: Silencing of Targeted Genes in Human Cells by siRNA Delivered by Sb-Derived EVs Through Functional Delivery of siRNA Externally Loaded to Sb-Derived EVs to Human Cells To evaluate the possibility for delivery of functional siRNA for gene silencing, Sur7 externally loaded EVs derived from wild-type Sb strain with siRNA targeting GFP using the lipofectamine 3000 agent, and then removed leftover lipofectamine by rinsing EVs mixture using centrifugation with 100 kDa cutoff filter. EVs loaded with siRNA-GFP were applied to H1299 cells expressing GFP reporter protein. The level of GFP fluorescence was measured for an evaluation of GFP expression.

To make sure that any possible silencing effect was not an artifact of lipofectamine-formed liposomes carrying siRNA, as a negative control we performed mock lipofectamine loading of siRNA to OptiMem media (Gibco, 11058021) without EVs and rinsed the mixture on a 100 kDA filter before application to the cells. The present inventors observed an average 35% decrease in GFP signal in human H1299 cells 72 hours after application of EVs loaded with siRNA compared to cells treated with mock transfection solution in two independent experiments (FIG. 5). These results demonstrate that Sb-derived EVs can deliver functional siRNA and induce silencing of targeted genes in human cells.

Example 5: Silencing of Targeted Viral Gene by EVs Derived from Engineered Sb Strains Expressing Specific shRNA The present inventors next sought to determine if EVs isolated from engineered Sb cells expressing siRNA are able to induce the silencing of a siRNA-targeted gene in human cells. For this purpose, we applied EVs isolated from both Sb-pol-I-siNsp1-siGFP and Sb-pol-II-siNsp1-siGFP as well as from wild type Sb to H1299-nsp1 human cells. 48 h after the application we extracted RNA from H1299 cells and used qRT-PCR to compare the level of nsp1 expression in cells treated with EVs from siRNA-expressing strains and cells treated with EVs derived from wt Sb. As shown in FIG. 6, treating H1299-nsp1 cells with EVs from Sb with siRNA-Nsp1 expression driven by RNA pol II caused 37% decrease in the level of nsp1 expression compared to cells treated with wild-type EVs (FIG. 6a), while the treatment with EVs isolated from Sb strain having RNA pol I driven siRNA expression induced only 15% of silencing of nsp1 gene (FIG. 6b)

Figure 7:
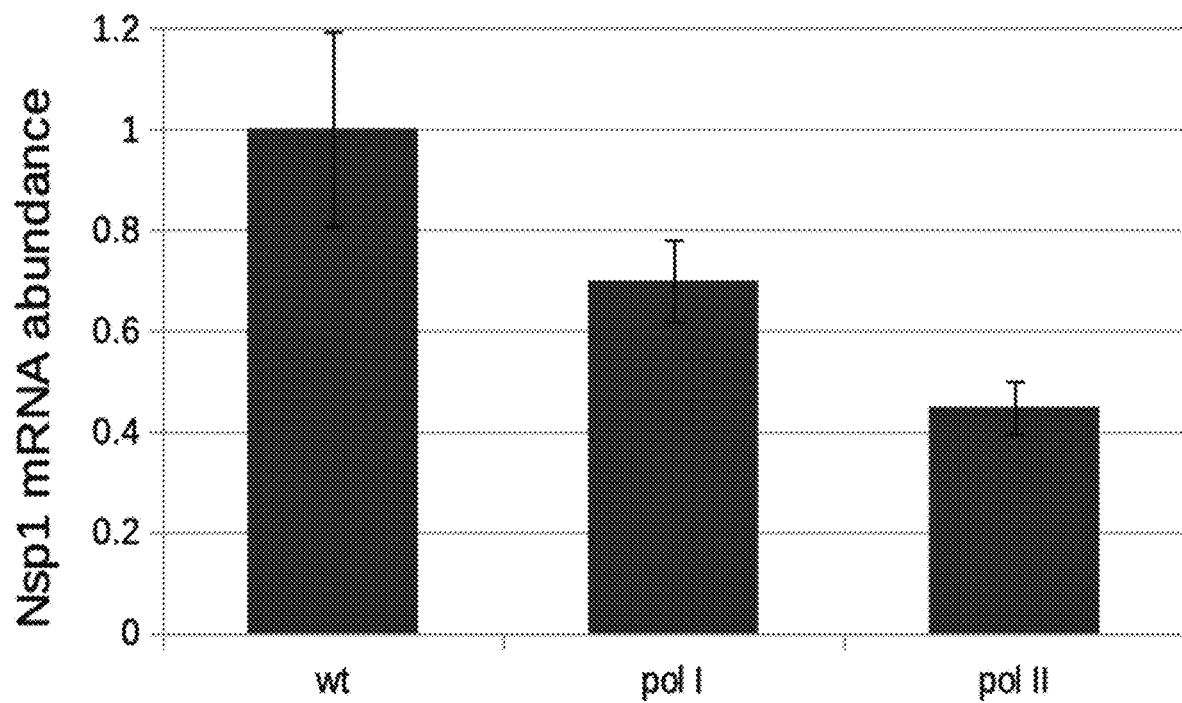

Example 6: EVs-Mediated Silencing of Targeted Viral Gene by Co-Cultivation shRNA-Expressing Sb with Human Cells Growing yeast constantly release EVs into their environment. Therefore, co-cultivation of targeted cells with engineered Sb strains producing EVs loaded by siRNA might be another way of siRNA delivery. In order to evaluate this possibility, we assembled a growth chamber with two sections divided by 0.4 um cutoff membrane. H1299 cells expressing the nsp1-GFP gene fusion construct were placed on the bottom section of the chamber, and wild type Sb or Sb strains expressing siRNA-nsp1 and siRNA-gfp were grown in the top section. This configuration allows the exchange of liquid and passage of EVs but not yeast themselves between two sections of the chamber. After 4 days of co-cultivation, the present inventors extracted RNA from H1299 cells and performed qPCR with primers to nsp1 gene to measure the nsp1 expression level. As shown in FIG. 7, the H1299 cells grown in the presence of both Sb strains expressing shRNA targeting nsp1 gene under control of pol I or pol II promoters the level of nsp1 expression was significantly lower (30% reduction for pol I-driven, and 52% reduction for pol II-driven siRNA expression) compared to the cells co-cultivated with wt Sb, though this effect was more prominent in cells co-cultivated with Sb-pol-II-siNsp1-siGFP strain.

Figure 8:
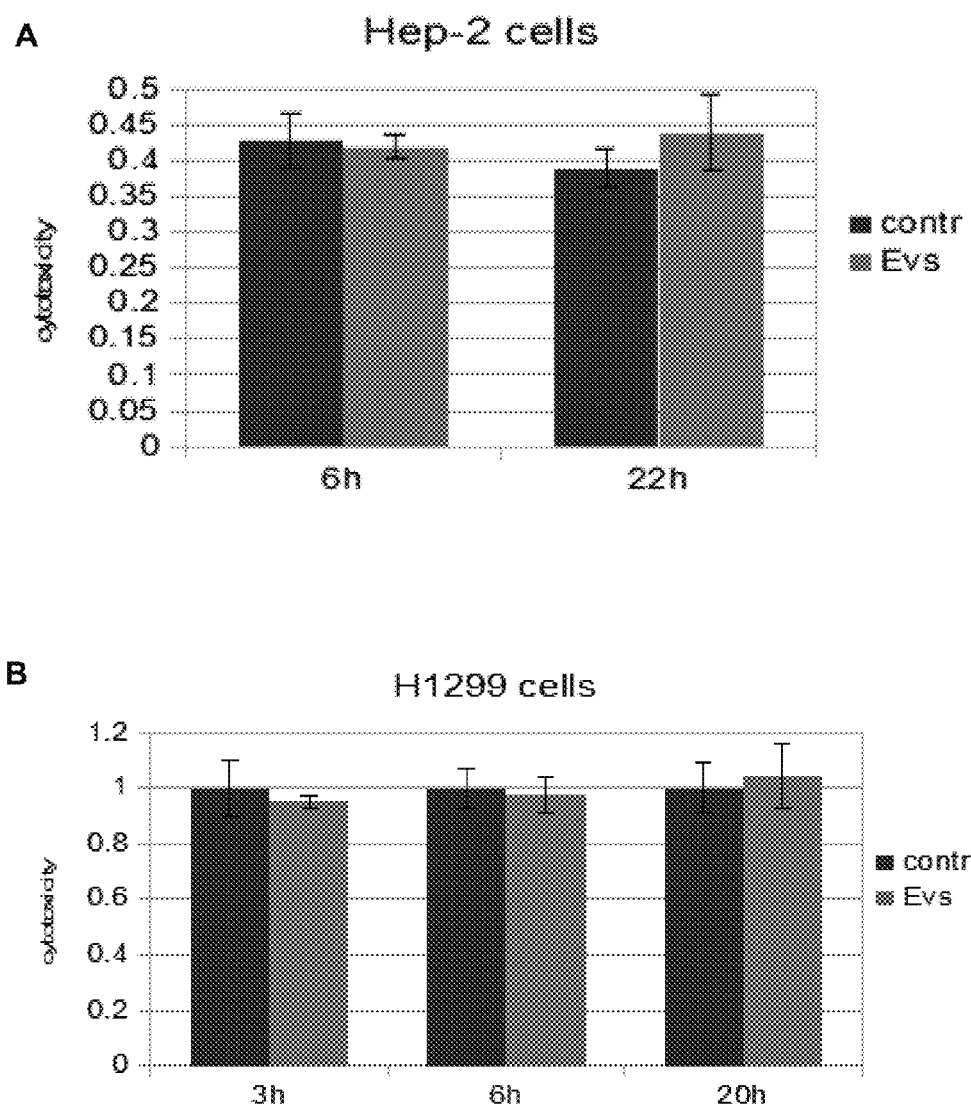
Figure 9:
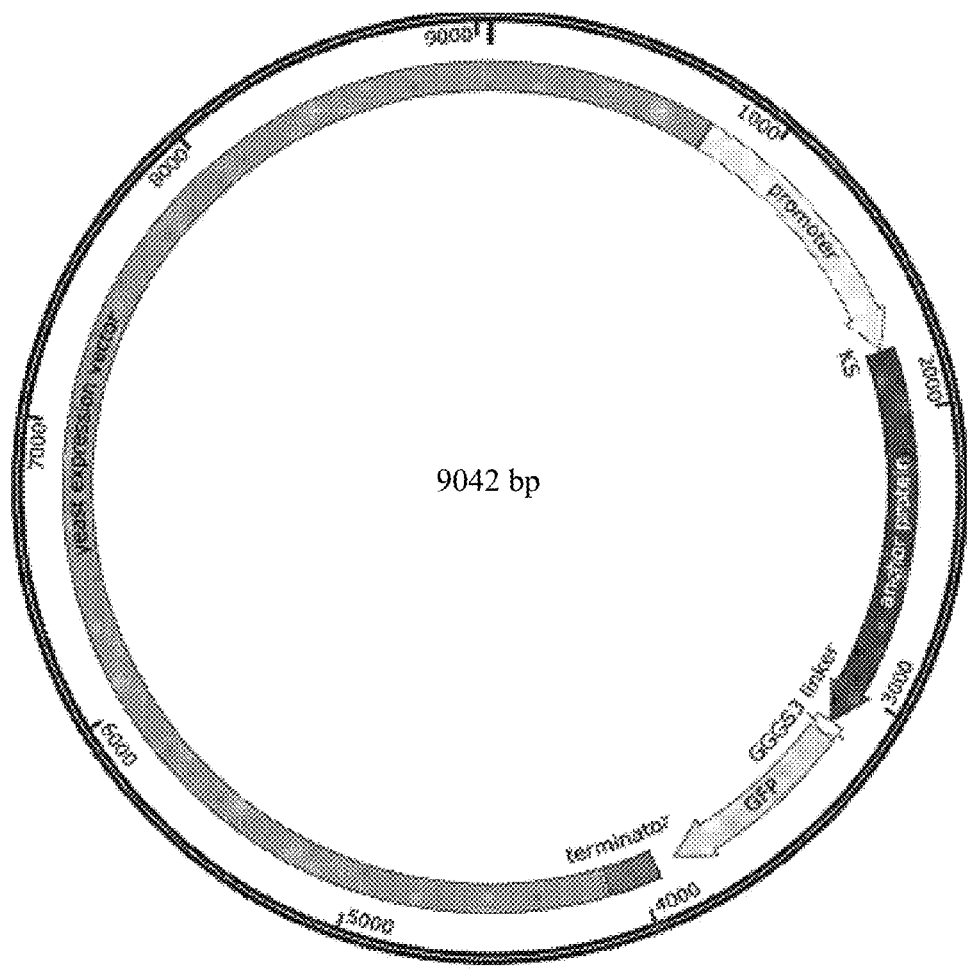
Figure 10:
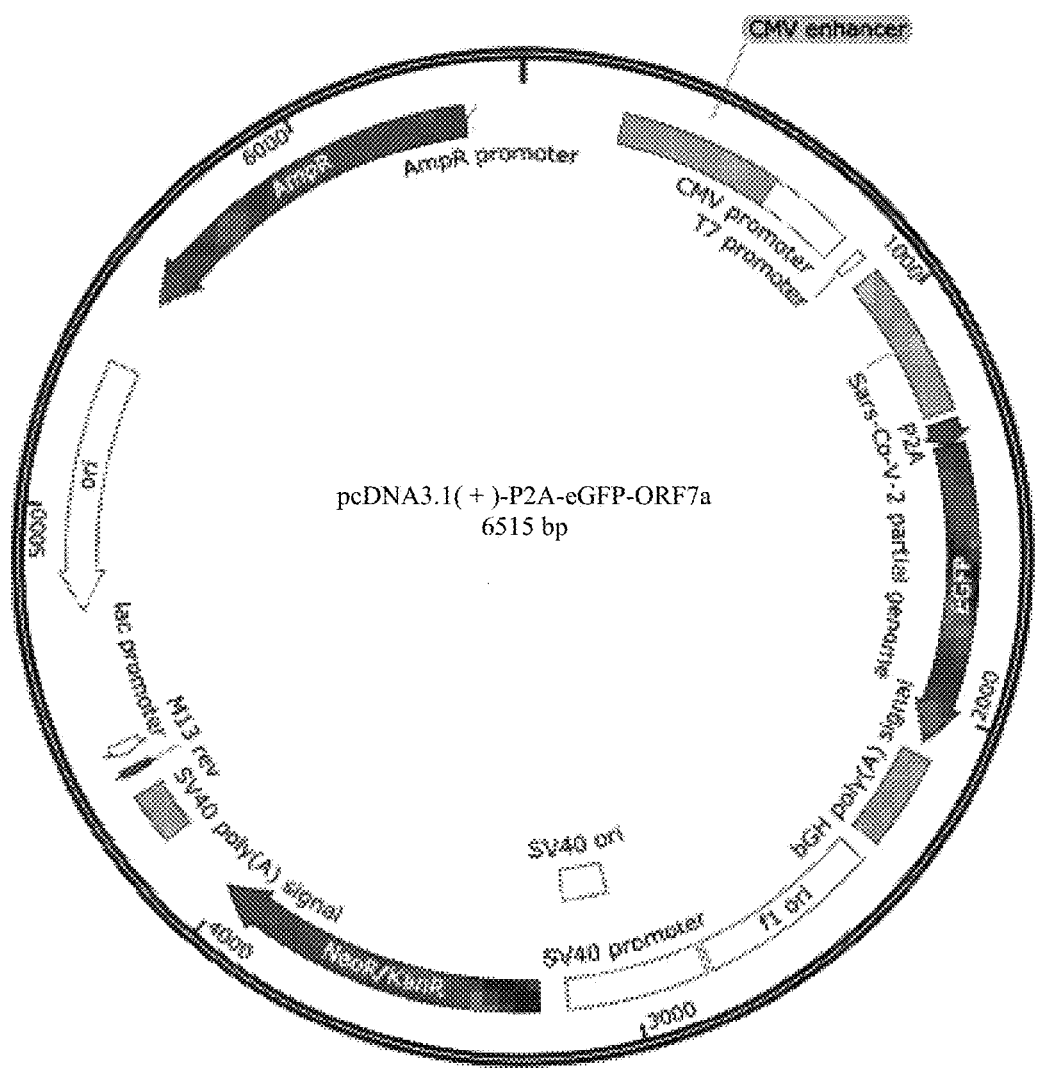
Figure 11:
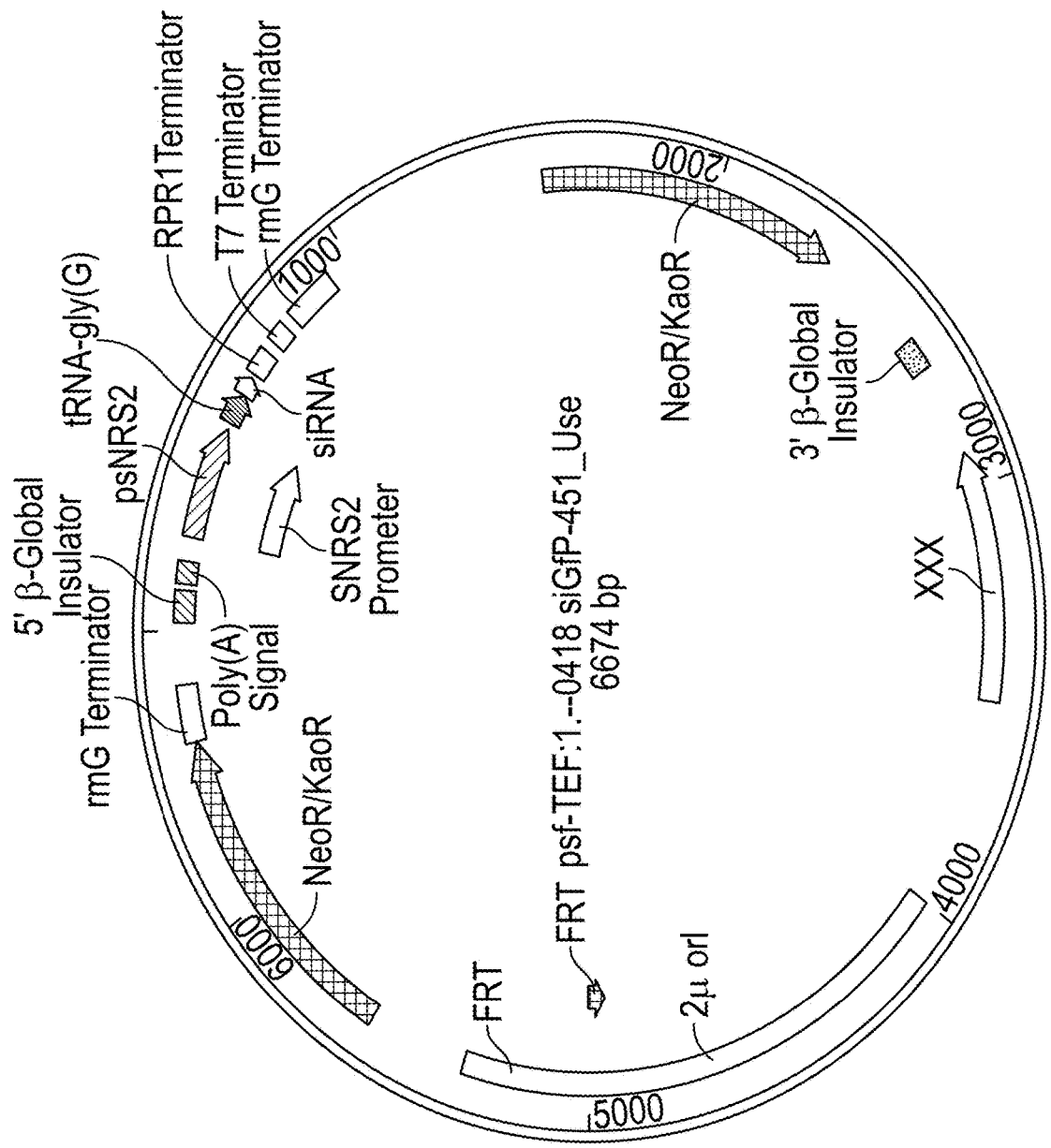

Example 7: The Level of Nsp1 Gene Expression in H1299 Co-Cultivated with wt Sb or Sb Expressing siRNA-nsp1 Under Control of Pol I or Pol II Promoters, Further Demonstrating Sb-Derived EVs Don't Have Cytotoxic Effect on Human Cells No previous research was done to evaluate the safety of Sb-derived EVs in human cell lines. As such, the present inventors conducted in vitro experiments to evaluate potential cytotoxicity of Sb-derived EVs for human lung cell line H1299 and human liver cancer cell line Hep-2 (often used as in vitro hepatotoxicity model). The present inventors performed lactate dehydrogenase activity assay of H1299 and Hep G2 cells following application of Sb-derived EVs in concentration $10^9$ EVs/ml. LDH is cytosolic enzyme which is released in the medium from dead cells due to damage of cell membranes, therefore higher amount of LDH in the medium indicate the cytotoxic effect. No significant toxicity was detected in both cell lines at a period 6-20 h after EVs application (FIG. 8).

Example 8: Materials and Methods

Sb strains design and construction: To create Sb strains expressing shRNA targeting nsp1 and eGFP genes, wild type Sb strain was transformed by dsDNA segments including siRNA expressing cassette and geneticin-resistance gene flanked on 5' and 3' ends by integration sequences homological to sequences from YIPRCt3 locus on the Sb XVI chromosome. Transformation was performed by electroporation method following protocol described by Benatui I et al (Benatuil et al, 2010)

Description of integration constructs: All constructs were synthesized by Genscript.

Polymerase I—based expression cassette: To utilize the RNA polymerase I gene promoter responsible for synthesis of rRNA which is major component of cells RNA pool, we designed expression cassette based on rRNA operon of Sb. Since upstream of rDNA has multiple promoter elements positioned on different distance from the start of transcription, in our design we included 5' Non-transcribed Spacer (NTS) from rRNA operon with 191 by of the Major promoter element following by minimal promoter element and first 25 bp of External translated spacer (Gallagher at al, 2019). The shRNA expression cassette contained tRNA-Ala, shRNA-nsp1, tRNA-Gly, shRNA-GFP and tRNA-Gly. 3' end of the expression cassette contained the terminator part of rRNA operon consisted from 210 bp of External Translated Spacer and 183 by of non-translated spacer (described in Gallagher et al, 2019)

RNA Polymerase II—based expression cassette: Consisted of the TDH3 promoter followed by tRNA-Ala, shRNA-nsp1, tRNA-Gly, shRNA-GFP, Hepatitis Delta Virus ribozyme and CYC1 terminator Sb labeling by fluorescent reporter gene: We cloned Sur7-GFP fused genes construct into psf-TEF1-G418 yeast selection vector (Sigma-Aldrich, OGS542) under control of TEF1 promoter and CYC1 terminator. The Sur7 protein (a membrane protein present in membrane compartments occupied by Can1) was found to be present in EVs produced by Saccharomyces cerevisiae strains (Dawson et al, 2020). For the visualization under the microscope, Sur7 was fused with monomeric mUkG1-GFP protein from soft coral was codon-optimized for expression in Saccharomyces (Kaishima et al, 2016). The Sur7-mUKG fusion gene was synthesized by Genscript and cloned into psf-TEF1 vector using inFusion kit (Takara).

Engineering of H1299 cells expressing partial sequence of SARS-CoV-2 genome and eGFP reporter gene for gene silencing experiments: 5' UTR and first 396 bp of nsp1 gene from genome of Sars-CoV-2 virus were sub-cloned into mammalian expression vector pcDNA3.1 (genscript.com/gsfiles/vector-map/mammalian/pcDNA3.1-reduce.pdf?2084916751) in frame with the self-cleaving 2A peptide and eGFP. Gene synthesis was performed by Genscript. H1299 cells (ATCC CRL-5803™) were transformed with plasmid pcDNA3.1-nsp1-eGFP using the lipofectamine 3000 reagent (Thermofisher L3000001) and grown on RPMI-1640 complete media (10% FBS, 1% penicillin-streptomycine) with addition of Geneticin® for selection of transformants. The procedure yielded the H1299-nsp1-GFP cell line expressing both 5'UTR-nsp1 gene and eGFP. This line was used in our experiments as a reporter for siRNA efficiency in targeted gene silencing.

Evaluation of siRNA efficiency: The siRNA-GFP targeting eGFP gene sequence was previously described by Reshke et al (Reshke et al, 2020). For the design of siRNAs targeting nsp1 gene, we used Genscript target finder tool (genscript.com/tools/sirna-target-finder). All nsp1 siRNA sequences are listed in Table 2. For analysis of the efficiency of nsp1 siRNAs, we transfected. H1299-nsp1 cells with each nsp1 siRNA construct using Lipofectamine 3000 reagent according to manufacturer protocol (thermofisher.com/us/en/home/brands/product-brand/lipofectamine/lipo-fectamine-3000.html). All nsp1 siRNA constructs were used at a 50 nM final concentration. 24 h after transfection the level of nsp1 gene expression was quantidfied by qPCR.

QRT-PCR. Relative nsp1 or GFP gene expression was measured by quantitative real-time PCR (qRT-PCR). Total RNA was isolated using RNA plus Nucleospin kit (Takara-Bio). Real-time PCR amplification was performed using a Mx3000P QPCR system (Agilent technologies). A Luna® Universal One-Step RT-qPCR Kit (NEB) was used to perform one step RT-PCR. Oligonucleotides concentration and cycling conditions were according to manufacturer recommendations. Gene specific primers are listed in Table 2. Approximately 25 ng of total RNA was used in each reaction. Relative expression levels of the specific transcripts were calculated using the Geneticin resistance gene mRNA as the internal reference for normalization.

Cell culture. H1299 cells (ATCC CRL-5803™) and Hep G2 cells (Sigma, 85011430) were maintained in RPMI-1640 medium supplemented with 10% fetal bovine serum (FBS; Gibco, Carlsbad, CA; #26140) and 100 U/ml penicillin/streptomycin (Invitrogen, Carlsbad, CA; #15140) and grown at 37° C. and 5% $CO_2$ Cells visualization and GFP fluorescence measurements: GFP fluorescence images of H1299-nsp1 cells were taken on an inverted fluorescent microscope (VWR 89404-464) using a GFP filter set and ×20 objective. Images were processed using ImageJ (1.47v) software. For live cell imaging of EVs uptake, 100 ul of Sur7-GFP labeled EVs were added to H1299 cells plated on glass-bottomed dishes and images were taken on Zeiss confocal microscope using a 63× oil immersion objective.

EVs extraction. Overnight cultures of *Saccharomyces boulardii* were diluted in 100 times with YPD medium. Cultures were then incubated for 16-24 h at 30° C. with shaking (200 rpm). For EV isolation, cells and debris were removed first by centrifugation at 3500×g for 35 min and then 15,000×g for 35 min. Supernatants were collected and ultracentrifuged at 100,000×g for 70 min at 4° C. (rotor SW32Ti, Optima EX-100-Ultracentrifuge, Beckman) to isolate EVs. Pellets were collected and washed once with 1 phosphate-buffered saline (PBS). The resulting EVs pellets were resuspended in 1 ml of PBS filtered through a 0.22 μm filter and stored at −80° C.

Application of EVs to H1299-nsp1 cells for gene silencing: EVs isolated from siRNA-Nsp1 expressing or from wild-type Sb strains were added to a sub-confluent monolayer of H1299 cells in 3 subsequent applications at 12 hour intervals. $10^{11}$ EVs/mL were used for each application. 48 h after first application of the EVs RNA was extracted from EV-treated cells and the level of Nsp1 expression was measured by qRT-PCR as described above.

Co-cultivation of H1299-nsp1 cells with Sb strains: H1299-nsp1 cells were plated in 6-well plates in complete RPMI-1640 medium. Permeable cell culture inserts with membrane pore size of 0.4 μm (Falcon™ 353090, 08-771) were placed on the top of each well to allow liquid exchange. The inserts were permeable for medium and EVs but not for yeast cells. 100 ul overnight culture of wild-type Sb or siRNA-nsp1 expressing Sb strains were added to the top section of the inserts. Half of the medium was carefully removed and replaced with fresh medium every 2 days during the experiment. The level of nsp1 expression was measured in H1299 cells co-cultivated with wild-type siRNA expressing strains 4 days after co-cultivation.

Cytotoxicity assay: $10^9$ EVs/ml were added to H1299 or Hep G2 cells and the release of lactate dehydrogenase (LDH) was measured in cell medium 3, 6 and 20 h after EVs application using the CyQUANT LDH Cytotoxicity Assay kit (invitrogen, C20300) following the manufacturer protocol.

miRNA dot blots. The purified miRNA samples were diluted in nuclease-free water to final concentration 0.2, 1.0 and 1.5 and 10-15 μl aliquots were then spotted to a positively charged nylon transfer membraned (Whatman Nytran SuPerCharge, GE Helthcare Life Sciences, Germany), resulting in total amount of 2.0, 3.0, 10.0, and 15.0 μg miRNA per dot, respectively. Chemically synthesized RNA oligonucleotides siGFP (5'- - - 3'), and siNSP1-2 (5'- - - 3') were obtained from Integrated DNA Technologies, Inc. (USA, San Diego). RNA probes were labeled to high specific activity using a DIG Oligonucleotide 3'-End labeling kit, 2 Generation (Roshe Diagnostics GmbH, Germany). After UV cross-linking to UVP HL-2000 using a HybriLinker Hybridization Oven UV Crosslinker (USA, Upland), the membranes were prehybridized at 42° C. for 30 min in ULTRAhyb™-Oligo Hybridization Buffer (Thermo Fisher Scientific Baltics UAB, Lithuania). After prehybridization, the purified labeled probe was added to the prehybridization buffer, and the membrane was hybridized at 42° C. for 14-18 h. After hybridization, the membranes were washed with twice 2×SSC-0.2% SDS (20 min at 42° C.), 2×SSC-0.2% SDS (20 min at 55° C., twice), 1×SSC-0.1% SDS (20 min at 55° C., twice). The membranes were then blocked and washed with the DIG Wash and. Block Buffer Set (Roshe Diagnostics GmbH, Germany). After washing the membranes chemiluminescence detection was performed using Anti-Digoxigenin-AP Fab fragments (Roshe Diagnostics GmbH, Germany), CDP-Star, ready-to-use (Roshe Diagnostics GmbH, Germany) and the Chemi-Doc XRS+ Imaging System (Bio-Rad). The signal intensities of the dots were quantified by densitometry using the Volume Tools of the image Lab software, version 6.0.1 build 34 (Bio-Rad).

Applicant incorporates by reference Examples 1-9 of priority reference U.S. Provisional Application Ser. No. 63/184,011, filed May 4, 2021.

TABLES

TABLE 1

Exemplary strains and cells lines.

|  | Genotype | Origin |
|---|---|---|
| Strains |  |  |
| *Saccharomyces boulardii* (Sb) | WT | ATCC type strain MYA-796 |
| Sb-pol-I-siNsp1-siGFP | pol-I-siNsp1-siGFP | This invention |
| Sb-pol-II-siNsp1-siGFP | pol-II-siNsp1-siGFP | This invention |
| Sb-Su7 | Sur7-GFP in psf-TEF1 vector | This invention |
| Cell lines |  |  |
| H1299 | Derived from Non-small cell lung cancer | ATCC CRL-5803 ™ |
| H1299-Nsp1 | H1299 Expressing 5'UTR and partial Nsp1 gene of SARS-CoV-2 virus in fusion with eGFP under CMV promoter | This invention |
| Hep G2 | Derived from human liver | Sigma, 85011430 |

TABLE 2

Exemplary Oligonucleotides sequences.

| Oligo | Sequence | Comments |
|---|---|---|
| shRNA-GFP | AUGAACUUCAGGGUCAGC UUGCGUUGACCCUGAAGU UCAUUC (SEQ ID NO. 17) | SiRNA targeting GFP |
| shRNA-Nsp1 | GGCAUUCAGUACGGUCG UAUAUUGGAGAUACGAC CGUACUGAAUGCCUU (SEQ ID NO. 18) | SiRNA targeting nsp1 SARS-CoV-2 gene |

TABLE 2-continued

Exemplary Oligonucleotides sequences.

| Oligo | Sequence | Comments |
|---|---|---|
| Nsp1 North | AGGCATTCAGTACGGTC GTA (SEQ ID NO. 19) | Probe for detection in Northern blot analysis |
| qNsp1-5' | CGTACGTGGCTTTGGA GACT (SEQ ID NO. 20) | Primer used for qPCR |
| qNsp1-3' | ACCATGAGGTGCAGTTC GAG (SEQ ID NO. 21) | Primer used for qPCR |
| qGen-5' | TGCTCGACGTTGTCACTG AA (SEQ ID NO. 22) | Primer used for qPCR |
| qGen-3' | GATGTTTCGCTTGGTGG TCG (SEQ ID NO. 23) | Primer used for qPCR |

REFERENCES

1. Establishing Probiotic *Saccharomyces boulardii* as a Model Organism for Synthesis and Delivery of Biomolecules Deniz Durmusoglu, Ibrahim Al'Abri, Scott P. Collins, Chase Beisel, Nathan Crook bioRxiv 2020.01.22.915389
2. Benatuil L, Perez J M, Belk J, Hsieh C M. An improved yeast transformation method for the generation of very large human antibody libraries. Protein Eng Des Sel. 2010 April; 23(4): 155-9.
3. Gallagher J E G. Proteins and RNA sequences required for the transition of the t-Utp complex into the SSU processome. FEMS Yeast Res. 2019 Jan 1; 19(1): foy120. doi: 10.1093/femsyr/foy120.
4. Dawson C S, Garcia-Ceron D, Rajapaksha H, Faou P, Bleackley M R, Anderson M A. Protein markers for *Candida albicans* EVs include claudin-like Sur7 family proteins. *J Extracell Vesicles.* 2020; 9(1):1750810. Published 2020 Apr. 16.
5. Kaishima, M., Ishii, J., Matsuno, T. et al. Expression of varied GFPs in *Saccharomyces cerevisiae:* codon optimization yields stronger than expected expression and fluorescence intensity. *Sci Rep* 6, 35932 (2016).
6. Reshke R, Taylor J A, Savard A, Guo H, Rhym L H, Kowalski P S, Trung M T, Campbell C, Little W, Anderson D G, Gibbings D. Reduction of the therapeutic dose of silencing RNA by packaging it in extracellular vesicles via a pre-microRNA backbone. Nat Biomed Eng. 2020 January; 4(1):52-68.
7. Levanova A, Poranen M M. RNA Interference as a Prospective Tool for the Control of Human Viral Infections. *Front Microbiol.* 2018; 9:2151. Published 2018 Sep. 11.
8. Zhang K, Miorin L, Makio T, Dehghan I, Gao S, Xie Y, Zhong H, Esparza M, Kehrer T, Kumar A, Hobman T C, Ptak C, Gao B, Minna J D, Chen Z, Garcia-Sastre A, Ren Y, Wozniak R W, Fontoura BMA. Nsp1 protein of SARS-CoV-2 disrupts the mRNA export machinery to inhibit host gene expression. Sci Adv. 2021 Feb. 5.
9. Durmaz S, Kurtoğlu T, Barbarus E, Çetin N K, Yilmaz M, Rahman ÖF, Abacigil F. Probiotic *Saccharomyces boulardii* Alleviates Lung Injury by Reduction of Oxidative Stress and Cytokine Response Induced by Supraceliac Aortic Ischemia-Reperfusion Injury in Rats. Braz J Cardiovasc Surg. 2020 Dec. 23.
10. Fidan I, Kalkanci A, Yesilyurt E, Yalcin B, Erdal B, Kustimur S, et al. Effects of *Saccharomyces boulardii* on cytokine secretion from intraepithelial lymphocytes infected by *Escherichia coli* and *Candida albicans*. Mycoses. 2009; 52(1):29-34.
11. Kelesidis T, Pothoulakis C. Efficacy and safety of the probiotic *Saccharomyces boulardii* for the prevention and therapy of gastrointestinal disorders. *Therap Adv Gastroenterol.* 2012; 5(2):111-125.
12. Bagherpour G, Ghasemi H, Zand B, Zarei N, Roohvand F, Ardakani E M, Azizi M, Khalaj V. Oral Administration of Recombinant *Saccharomyces boulardii* Expressing Ovalbumin-CPE Fusion Protein Induces Antibody Response in Mice. Front Microbiol. 2018 Apr. 13; 9:723.
13. Bellavia D, Raimondo S, Calabrese G, et al. Interleukin 3-receptor targeted exosomes inhibit in vitro and in vivo Chronic Myelogenous Leukemia cell growth. *Theranostics.* 2017; 7(5):1333-1345. Published 2017 Mar. 16.
14. Hudson L E, McDermott C D, Stewart T P, Hudson W H, Rios D, Fasken M B, Corbett A H, Lamb T J. Characterization of the Probiotic Yeast *Saccharomyces boulardii* in the Healthy Mucosal Immune System. PLoS One. 2016 Apr. 11; 11(4).
15. Inada M, Guthrie C. Identification of Lhp1p-associated RNAs by microarray analysis in *Saccharomyces cerevisiae* reveals association with coding and noncoding RNAs. Proc Natl Acad Sci USA. 2004 Jan. 13; 101(2):434-9.
16. Infection and Immunity April 2001, 69 (4) 2762-2765.
17. Joossens, PhD, P Suenaert, MD, PhD, M Noman, MD, S Vermeire, MD, PhD, P Rutgeerts, MD, PhD, *Saccharomyces boulardii* in Crohn's Disease: Effect on Anti-*Saccharomyces cerevisiae* Antibodies and Intestinal Permeability, *Inflammatory Bowel Diseases,* Volume 11, Issue 9, 1 Sep. 2005, Pages 863-864.
18. Karen M, Yuksel O, Akyürek N, Ofluoğlu E, Cağlar K, Sahin TT, Paşaoğlu H, Memiş L, Akyürek N, Bostanci H. Probiotic agent *Saccharomyces boulardii* reduces the incidence of lung injury in acute necrotizing pancreatitis induced rats. J Surg Res. 2010 May 1;160(1): 139-44.
19. Peres da Silva, R., Puccia, R., Rodrigues, M. et al. Extracellular vesicle-mediated export of fungal RNA. *Sci Rep* 5, 7763 (2015).
20. Silveira, M., Rosa, R., Mendonça, M. et al. *Saccharomyces boulardii* ingestion increases the humoral response of a DNA vaccine against leptospirosis in mice. *BMC Proc* 8, P160 (2014).
21. Rizzo J, Rodrigues ML, Janbon G. Extracellular Vesicles in Fungi: Past, Present, and Future Perspectives. *Front Cell Infect Microbiol.* 2020; 10:346.

What is claimed is:

1. A pharmaceutical composition for the treatment of SARS-COV-2, comprising a quantity of extracellular vesicles (EVs) containing a heterologous ribonucleic acid (RNA) molecules directed to inhibit the expression of a SARS-CoV-2 gene, and a pharmaceutically acceptable carrier, wherein the EVs are generated from *Saccharomyces boulardii*.

2. The pharmaceutical composition of claim 1, wherein the heterologous RNA is selected from: a dsRNA, a miRNA, a or a siRNA.

3. The pharmaceutical composition of claim 1, wherein the heterologous RNA comprises an RNA according to SEQ ID NO. 18, or a fragment thereof, or an RNA having at least 98% homology with SEQ ID NO. 18, or a fragment thereof.

4. The pharmaceutical composition of claim 1, further comprising at least one heterologous membrane surface ligand that binds to a target surface molecule displayed on a target cell, wherein the at least one heterologous membrane surface ligand is linked to an anchor protein embedded in the lipid bilayer of the EV.

5. The pharmaceutical composition of claim 4, wherein the anchor protein is selected from the group consisting of: ammonia transport outward protein 2, plasma membrane protein up-regulated during nitrogen stress protein 1, glucan 1,3-beta-glucosidase 1/11, glucan 1,3-beta-glucosidase, 1,3-beta-glucanosyltransferase, 1,3-beta-glucanosyltransferase, iron transport multicopper oxidase, probable glycosidase protein, and non-classical export protein 1, Sur7 protein.

6. The pharmaceutical composition of claim 4, wherein the target surface molecule is selected from: an enzyme, an antigen expressed on an immune cell, an antigen expressed on an immune effector cell, a peptide, an antigen, human angiotensin converting enzyme 2 (ACE2), neuropilin 1 (NRP1), and transmembrane protease serine 2 (TMPRSS2).

7. The pharmaceutical composition of claim 4, wherein the at least one heterologous membrane surface ligand is selected from: angiotensin II, and vascular endothelial growth factor A (VEGF-A).

8. A pharmaceutical composition comprising: a quantity of extracellular vesicle (EVs) containing a heterologous RNA directed to inhibit the expression of a pathogen gene, or an endogenous gene of a target cell, and a pharmaceutically acceptable carrier, wherein the EVs are generated from *Saccharomyces boulardii*.

9. The pharmaceutical composition of claim 8, wherein pathogen is SARS-CoV-2 virus.

10. The pharmaceutical composition of claim 9, wherein the heterologous RNA comprises an RNA according to SEQ ID NO. 18, or a fragment thereof, or an RNA having at least 98% homology with SEQ ID NO. 18, or a fragment thereof.

11. The pharmaceutical composition of any of claims 8, wherein the heterologous RNA is selected from: a dsRNA, a miRNA, a siRNA, and a siRNA.

12. A extracellular vesicle (EV) comprising a heterologous RNA molecule and optionally at least one heterologous membrane surface ligand that binds to a target surface molecule displayed on a target cell, wherein the at least one heterologous membrane surface ligand is linked to an anchor protein embedded in the lipid bilayer of the EV, and wherein the EV is generated from *Saccharomyces boulardii*.

13. The extracellular vesicle of claim 12, wherein the heterologous RNA is selected from: a dsRNA, a miRNA, a siRNA, and a siRNA.

14. The extracellular vesicle of claim 12, wherein the anchor protein is selected from the group consisting of: ammonia transport outward protein 2, plasma membrane protein up-regulated during nitrogen stress protein 1, glucan 1,3-beta-glucosidase 1/11, glucan 1,3-beta-glucosidase, 1,3-beta-glucanosyltransferase, 1,3-beta-glucanosyltransferase, iron transport multicopper oxidase, probable glycosidase protein, and non-classical export protein 1, Sur7 protein.

15. The extracellular vesicle of claim 12, wherein the target surface molecule is selected from: an enzyme, an antigen expressed on an immune cell, an antigen expressed on an immune effector cell, a peptide, an antigen, human angiotensin converting enzyme 2 (ACE2), neuropilin 1 (NRP1), transmembrane protease and serine 2 (TMPRSS2).

16. The extracellular vesicle of claim 12, wherein the at least one heterologous membrane surface ligand is selected from: angiotensin II, vascular endothelial growth factor A (VEGF-A).

* * * * *

SEQUENCE LISTING

<160> NUMBER OF SEQ ID NOS: 37

<210> SEQ ID NO 1
<211> LENGTH: 49
<212> TYPE: DNA
<213> ORGANISM: Artificial
<220> FEATURE:
<223> OTHER INFORMATION: shRNA-nsp1

<400> SEQUENCE: 1
ggcattcagt acggtcgtat attggagata cgaccgtact gaatgcctt                49

<210> SEQ ID NO 2
<211> LENGTH: 42
<212> TYPE: DNA
<213> ORGANISM: Artificial
<220> FEATURE:
<223> OTHER INFORMATION: shRNA-GFP

<400> SEQUENCE: 2
atgaacttca gggtcagctt gcgttgaccc tgaagttcat tc                       42

<210> SEQ ID NO 3
<211> LENGTH: 1199
<212> TYPE: DNA
<213> ORGANISM: Artificial
<220> FEATURE:
<223> OTHER INFORMATION: Polymerase I-promoter driven expression
      cassette

<400> SEQUENCE: 3
gcggccgccc gcttccgctt ccgcagtaaa aatagtgag gaactgggtt agaattctat     60
gatccgggta aaacatgta ttgtatatat ctattataat atacgatgag gatgatagtg    120
tgtaagagtg taccatttac taatgtatgt aagttactat ttactatttg gtctttttat   180
ttttcatttt ttttttttc gttgcaaaga tgggttgaaa gagaagggct ttcacaaagc    240
ttcccggggc acctgtcact ttggaaaaaa aatatacgct aagatttttg gagaatagct   300
taaattgaag ttttttctcgg cgagaaatac gtagttaagg cagagcgaca gagagggcaa   360
aagaaaataa agtaagatt ttagtttgta atgggagggg gggtttagtc atggagtaca    420
agtgtgagga aaagtagttg ggaggtactt catgcgaaag cagttgaaga caagttcaaa    480
acgggcgtgt ggcgtagttg gtagcgcgtt cccttagcat gggaaaggtc atgagttcga    540
ctcttatctc gtccaggcat tcagtacggt cgtatattgg agatacgacc gtactgaatg    600
ccttgcgcaa gtggtttagt ggtaaaatcc aacgttgcca tcgttgggcc cccggttcga    660
ttccgggctt gcgcaatgaa cttcagggtc agcttgcgtt gaccctgaag ttcattcgcg    720
caagtggttt agtggtaaaa tccaacgttg ccatcgttgg gccccggtt cgattccggg     780 cttgcgcatt ttatttcttt ctaagtgggt actggcagga gccggggcct agtttagaga    840
gaagtagact gaacaagtct ctataaattt tatttgtctt aagaattcta tgatccgggt    900
aaaaacatgt attgtatata tctattataa tatacgatga ggatgatagt gtgtaagagt    960
gtaccattta ctaatgtatg taagttacta tttactattt ggtcttttta ttttcattt   1020 tttttttttt cgttgcaaag atgggttgaa agagaagggc tttcacaaag cttcccgagc   1080
gtgaaaggat ttgcccggac agtttgcttc atggagcagt ttttccgca ccatcagagc    1140 ggcaaacatg agtgcttgta taagtttaga gaattgagaa aagctcattt cttaattaa    1199

<210> SEQ ID NO 4

<211> LENGTH: 746
<212> TYPE: DNA
<213> ORGANISM: Saccharomyces

<400> SEQUENCE: 4

```
ggccaaggca aaaagattcc ttgattacgt aagggagtta gaatcatttt gaataaaaaa      60
cacgctttt  cagttcgagt ttatcattat caatactgcc atttcaaaga atacgtaaat     120
aattaatagt agtgattttc ctaactttat ttagtcaaaa aattagcctt ttaattctgc     180
tgtaacccgt acatgcccaa ataggggggc gggttacaca gaatatataa catcgtaggt     240
gtctgggtga acagtttatt cctggcatcc actaaatata atggagcccg cttttttaagc    300
tggcatccag aaaaaaaaag aatcccagca ccaaatatt  gttttcttca ccaaccatca     360
gttcataggt ccattctctt agcgcaacta cagagaacag gggcacaaac aggcaaaaaa     420
cgggcacaac ctcaatggag tgatgcaacc tgcctggagt aaatgatgac acaaggcaat     480
tgacccacgc atgtatctat ctcattttct tacaccttct attaccttct gctctctctg     540
atttggaaaa agctgaaaaa aaaggttgaa accagttccc tgaaattatt cccctacttg     600
actaataagt atataaagac ggtaggtatt gattgtaatt ctgtaaatct atttcttaaa     660
cttcttaaat tctactttta tagttagtct ttttttttagt tttaaaacac caagaactta    720
gtttcgaata aacacacata aacaaa                                          746
```

<210> SEQ ID NO 5
<211> LENGTH: 325
<212> TYPE: DNA
<213> ORGANISM: Saccharomyces

<400> SEQUENCE: 5

```
acaggccccct tttcctttgt cgatatcatg taattagtta tgtcacgctt acattcacgc      60
cctcccccca catccgctct aaccgaaaag gaaggagtta gacaacctga agtctaggtc     120
cctatttatt tttttatagt tatgttagta ttaagaacgt tatttatatt tcaaattttt     180
cttttttttc tgtacaaacg cgtgtacgca tgtaacatta tactgaaaac cttgcttgag     240
aaggttttgg gacaagctta cgtctcacgg atcgtatatg ccgtagcgac aatctaagaa     300
ctatgcgagg acacgctagc agctg                                            325
```

<210> SEQ ID NO 6
<211> LENGTH: 1392
<212> TYPE: DNA
<213> ORGANISM: Artificial
<220> FEATURE:
<223> OTHER INFORMATION: Polymerase II-promoter driven expression
      cassette

<400> SEQUENCE: 6

```
ggccaaggca aaaagattcc ttgattacgt aagggagtta gaatcatttt gaataaaaaa      60
cacgctttt  cagttcgagt ttatcattat caatactgcc atttcaaaga atacgtaaat     120
aattaatagt agtgattttc ctaactttat ttagtcaaaa aattagcctt ttaattctgc     180
tgtaacccgt acatgcccaa ataggggggc gggttacaca gaatatataa catcgtaggt     240
gtctgggtga acagtttatt cctggcatcc actaaatata atggagcccg cttttttaagc    300
tggcatccag aaaaaaaaag aatcccagca ccaaatatt  gttttcttca ccaaccatca     360
gttcataggt ccattctctt agcgcaacta cagagaacag gggcacaaac aggcaaaaaa     420
cgggcacaac ctcaatggag tgatgcaacc tgcctggagt aaatgatgac acaaggcaat     480
```

```
tgacccacgc atgtatctat ctcattttct tacaccttct attaccttct gctctctctg    540
atttggaaaa agctgaaaaa aaaggttgaa accagttccc tgaaattatt ccccctacttg    600 actaataagt atataaagac ggtaggtatt gattgtaatt ctgtaaatct atttcttaaa    660
cttcttaaat tctactttta tagttagtct tttttttagt tttaaaacac caagaactta    720
gtttcgaata acacacata aacaaaaaac aaagagctca aacgggcgt gtggcgtagt      780 tggtagcgcg ttcccttagc atgggaaagg tcatgagttc gactcttatc tcgtccaggc    840
attcagtacg gtcgtatatt ggagatacga ccgtactgaa tgccttgcgc aagtggttta    900
gtggtaaaat ccaacgttgc catcgttggg cccccggttc gattccgggc ttgcgcaatg    960
aacttcaggg tcagcttgcg ttgaccctga agttcattcg gccggcatgg tcccagcctc   1020
ctcgctggcg ccggctgggc aacatgcttc ggcatggcga atgggacaca ggccccttt    1080 cctttgtcga tatcatgtaa ttagttatgt cacgcttaca ttcacgccct cccccacat    1140 ccgctctaac cgaaaaggaa ggagttagac aacctgaagt ctaggtccct atttatttt    1200 ttatagttat gttagtatta agaacgttat ttatatttca aattttctt tttttctgt     1260 acaaacgcgt gtacgcatgt aacattatac tgaaaacctt gcttgagaag gttttgggac   1320
aagcttacgt ctcacggatc gtatatgccg tagcgacaat ctaagaacta tgcgaggaca   1380
cgctagcagc tg                                                       1392
```

<210> SEQ ID NO 7
<211> LENGTH: 493
<212> TYPE: DNA
<213> ORGANISM: Artificial
<220> FEATURE:
<223> OTHER INFORMATION: 5' homological sequence for genome integration
      at chromosome XVI

<400> SEQUENCE: 7

```
tgtgcagcat attgtcctct agatgcaaac tctgcaggtc catttgcagt aaagtgagtt     60
gcctctcgaa gaatcattaa tttcgtataa ccgtcactat taaagtcaga aaataaattc    120
tgtcgtagac aatgttacca taatgttctt gtccattttg catacacttt aaatattcat    180
ttgatttctc agggttcatg atcataataa attgcgcatt cgcaaggcgg tagtattata    240
atggggtcca tcattctgta gcaagaagtt acagtacgct gttcaagcgt taaacaagat    300
aagtaatctc gaatgaaaca ttcatatttc gcatgagcca acatacagtt gctgagtaat    360
cttcattgcg cttatttatc ggcattgaga ttgtaaagga agtaaaacgc attttttgcag   420 atctgttctc ttatgtattt ttaatcgtcc ttgtatggaa gtatcaaagg ggacgttctt    480 caccctccttg gaa                                                     493
```

<210> SEQ ID NO 8
<211> LENGTH: 453
<212> TYPE: DNA
<213> ORGANISM: Artificial
<220> FEATURE:
<223> OTHER INFORMATION: 3' homological sequence for genome integration
      at chromosome XVI

<400> SEQUENCE: 8

```
gcgactagat tgtaaatcat tctttatttta atctctttct ttaactactg cttaaagtat    60
aatttggtcc gtagtttaat aactatacta agcgtaacaa tgcatactga cattataagc    120
ctgaacatta cgagtttaag ttgtatgtag gcgttctgta agaggttact gcgtaaatta    180
tcaacgaatg cattggtgta tttgcgaaag ctacttctt taacaagtat ttacataaga    240
```

```
ataatggtga tctgctcaac tgatttggtg ataactctaa cttttttagc aacaatttaa      300
aagataattc gaacatatat aacagtagga agaatttgtg tacgtcaaat taagataatt      360
tagcattacc aaagttatta acctaaacat aaaatatata tgagacacat gtggaaatcg      420
tatgaaacaa ctgttatgaa actgacaaga atg                                   453
```

<210> SEQ ID NO 9
<211> LENGTH: 3618
<212> TYPE: DNA
<213> ORGANISM: Artificial
<220> FEATURE:
<223> OTHER INFORMATION: Full sequence of polymerase I-based integration insert

<400> SEQUENCE: 9

```
tgtgcagcat attgtcctct agatgcaaac tctgcaggtc catttgcagt aaagtgagtt       60
gcctctcgaa gaatcattaa tttcgtataa ccgtcactat taaagtcaga aaataaaattc     120 tgtcgtagac aatgttacca taatgttctt gtccattttg catacacttt aaatattcat     180
ttgatttctc agggttcatg atcataataa attgcgcatt cgcaaggcgg tagtattata     240
atggggtcca tcattctgta gcaagaagtt acagtacgct gttcaagcgt taaacaagat     300
aagtaatctc gaatgaaaca ttcatatttc gcatgagcca acatacagtt gctgagtaat     360
cttcattgcg cttatttatc ggcattgaga ttgtaaagga agtaaaacgc attttttgcag    420 atctgttctc ttatgtattt ttaatcgtcc ttgtatggaa gtatcaaagg ggacgttctt     480
cacctccttg aataggtct agagatctgt ttagcttgcc tcgtcccgc cgggtcaccc       540 ggccagcgac atggaggccc agaatacccct ccttgacagt cttgacgtgc gcagctcagg    600
ggcatgatgt gactgtcgcc cgtacattta gcccatacat ccccatgtat aatcatttgc    660
atccatacat tttgatggcc gcacggcgcg aagcaaaaat tacggctcct cgctgcagac    720
ctgcgagcag ggaaacgctc ccctcacaga gcgttgaat tgtccccacg ccgcgccccct    780 gtagagaaat ataaaaggtt aggatttgcc actgaggttc ttctttcata tacttccttt     840
taaaatcttg ctaggataca gttctcacat cacatccgaa cataaacaac catgggtaag     900
gaaaagactc acgtttcgag gccgcgatta aattccaaca tggatgctga tttatatggg    960
tataaatggg ctcgcgataa tgtcgggcaa tcaggtgcga caatctatcg attgtatggg     1020
aagcccgatg cgccagagtt gtttctgaaa catggcaaag gtagcgttgc caatgatgtt    1080
acagatgaga tggtcagact aaactggctg acggaattta tgcctcttcc gaccatcaag    1140 catttatcc gtactcctga tgatgcatgg ttactcacca ctgcgatccc cggcaaaaca    1200
gcattccagg tattagaaga atatcctgat tcaggtgaaa atattgttga tgcgctggca   1260
gtgttcctgc gccggttgca ttcgattcct gtttgtaatt gtcctttaa cagcgatcgc    1320 gtatttcgtc tcgctcaggc gcaatcacga atgaataacg gtttggttga tgcgagtgat    1380
tttgatgacg agcgtaatgg ctggcctgtt gaacaagtct ggaaagaaat gcataagctt    1440
ttgccattct caccggattc agtcgtcact catggtgatt tctcacttga taaccttatt    1500
tttgacgagg ggaaattaat aggttgtatt gatgttggac gagtcggaat cgcagaccga    1560
taccaggatc ttgccatcct atggaactgc ctcggtgagt ttctccttc attacagaaa    1620 cggctttttc aaaaatatgg tattgataat cctgatatga ataaattgca gtttcatttg    1680
atgctcgatg agttttttcta atcagtactg acaataaaaa gattcttgtt ttcaagaact    1740
tgtcatttgt atagtttttt tatattgtag ttgttctatt ttaatcaaat gttagcgtga    1800
```

```
tttatatttt ttttcgcctc gacatcatct gcccagatgc gaagttaagt gcgcagaaag    1860
taatatcatg cgtcaatcgt atgtgaatgc tggtcgctat actgctgtcg attcgatact    1920
aacgccgcca tccagtgtcg aaaacgagct ctcgagaacc cttaatgcgg ccgcccgctt    1980
ccgcttccgc agtaaaaaat agtgaggaac tgggttagaa ttctatgatc cgggtaaaaa    2040
catgtattgt atatatctat tataatatac gatgaggatg atagtgtgta agagtgtacc    2100
atttactaat gtatgtaagt tactatttac tatttggtct ttttattttt cattttttt    2160 tttttcgttg caaagatggg ttgaaagaga agggcttttca caaagcttcc cggggcacct    2220
gtcactttgg aaaaaaaata tacgctaaga tttttggaga atagcttaaa ttgaagtttt    2280
tctcggcgag aaatacgtag ttaaggcaga gcgacagaga gggcaaaaga aaataaaagt    2340
aagattttag tttgtaatgg gagggggggt ttagtcatgg agtacaagtg tgaggaaaag    2400
tagttgggag gtacttcatg cgaaagcagt tgaagacaag ttcaaaacgg gcgtgtggcg    2460
tagttggtag cgcgttccct tagcatggga aaggtcatga gttcgactct tatctcgtcc    2520
aggcattcag tacggtcgta tattggagat acgaccgtac tgaatgcctt gcgcaagtgg    2580
tttagtggta aaatccaacg ttgccatcgt tgggcccccg gttcgattcc gggcttgcgc    2640
aatgaacttc agggtcagct tgcgttgacc ctgaagttca ttcgcgcaag tggtttagtg    2700
gtaaaatcca acgttgccat cgttgggccc cggttcgat tccgggcttg cgcatttat    2760 ttctttctaa gtgggtactg gcaggagccg gggcctagtt tagagagaag tagactgaac    2820
aagtctctat aaattttatt tgtcttaaga attctatgat ccgggtaaaa acatgtattg    2880
tatatatcta ttataatata cgatgaggat gatagtgtgt aagagtgtac catttactaa    2940
tgtatgtaag ttactattta ctatttggtc ttttattttt tcattttttt tttttcgtt    3000 gcaaagatgg gttgaaagag aagggctttc acaaagcttc cgagcgtga aggatttgc    3060 ccggacagtt tgcttcatgg agcagttttt tccgcaccat cagagcggca acatgagtg    3120 cttgtataag tttagagaat tgagaaaagc tcatttctta attaagcgac tagattgtaa    3180
atcattcttt atttaatctc tttctttaac tactgcttaa agtataattt ggtccgtagt    3240
ttaataacta tactaagcgt aacaatgcat actgacatta taagcctgaa cattacgagt    3300
ttaagttgta tgtaggcgtt ctgtaagagg ttactgcgta aattatcaac gaatgcattg    3360
gtgtatttgc gaaagctact tctttttaaca agtatttaca taagaataat ggtgatctgc    3420
tcaactgatt tggtgataac tctaactttt ttagcaacaa tttaaaagat aattcgaaca    3480
tatataacag taggaagaat ttgtgtacgt caaattaaga taatttagca ttaccaaagt    3540
tattaaccta acataaaat atatatgaga cacatgtgga aatcgtatga aacaactgtt    3600
atgaaactga caagaatg                                                  3618
```

<210> SEQ ID NO 10
<211> LENGTH: 3879
<212> TYPE: DNA
<213> ORGANISM: Artificial
<220> FEATURE:
<223> OTHER INFORMATION: Full sequence of polymerase II-based
      integration insert

<400> SEQUENCE: 10

```
tgtgcagcat attgtcctct agatgcaaac tctgcaggtc catttgcagt aaagtgagtt      60
gcctctcgaa gaatcattaa tttcgtataa ccgtcacact taaagtcaga aaataaattc     120
tgtcgtagac aatgttacca taatgttctt gtccattttg catacacttt aaatattcat     180
```

```
ttgatttctc agggttcatg atcataataa attgcgcatt cgcaaggcgg tagtattata    240
atggggtcca tcattctgta gcaagaagtt acagtacgct gttcaagcgt taaacaagat    300
aagtaatctc gaatgaaaca ttcatatttc gcatgagcca acatacagtt gctgagtaat    360
cttcattgcg cttatttatc ggcattgaga ttgtaaagga agtaaaacgc atttttgcag    420
atctgttctc ttatgtattt ttaatcgtcc ttgtatggaa gtatcaaagg ggacgttctt    480
cacctccttg gaataggtct agagatctgt ttagcttgcc tcgtcccgc cgggtcaccc     540 ggccagcgac atggaggccc agaataccct ccttgacagt cttgacgtgc gcagctcagg    600
ggcatgatgt gactgtcgcc cgtacattta gcccatacat ccccatgtat aatcatttgc    660
atccatacat tttgatggcc gcacggcgcg aagcaaaaat tacggctcct cgctgcagac    720
ctgcgagcag ggaaacgctc ccctcacaga cgcgttgaat tgtccccacg ccgcgcccct    780
gtagagaaat ataaaggtt aggatttgcc actgaggttc ttctttcata tacttccttt     840
taaaatcttg ctaggataca gttctcacat cacatccgaa cataaacaac catgggtaag    900
gaaaagactc acgtttcgag gccgcgatta aattccaaca tggatgctga tttatatggg    960
tataaatggg ctcgcgataa tgtcgggcaa tcaggtgcga caatctatcg attgtatggg    1020
aagcccgatg cgccagagtt gtttctgaaa catggcaaag gtagcgttgc caatgatgtt    1080
acagatgaga tggtcagact aaactggctg acggaattta tgcctcttcc gaccatcaag    1140
cattttatcc gtactcctga tgatgcatgg ttactcacca ctgcgatccc cggcaaaaca    1200
gcattccagg tattagaaga atatcctgat tcaggtgaaa atattgttga tgcgctggca    1260
gtgttcctgc gccggttgca ttcgattcct gtttgtaatt gtccttttaa cagcgatcgc    1320
gtatttcgtc tcgctcaggc gcaatcacga atgaataacg tttggttga tgcgagtgat     1380 tttgatgacg agcgtaatgg ctggcctgtt gaacaagtct ggaaagaaat gcataagctt    1440
ttgccattct caccggattc agtcgtcact catggtgatt tctcacttga taaccttatt    1500
tttgacgagg ggaaattaat aggttgtatt gatgttggac gagtcggaat cgcagaccga    1560
taccaggatc ttgccatcct atggaactgc ctcggtgagt tttctccttc attacagaaa    1620
cggctttttc aaaaatatgg tattgataat cctgatatga taaattgca gtttcatttg     1680 atgctcgatg agtttttcta atcagtactg acaataaaaa gattcttgtt ttcaagaact    1740
tgtcatttgt atagttttt tatattgtag ttgttctatt ttaatcaaat gttagcgtga     1800
tttatatttt ttttcgcctc gacatcatct gcccagatgc gaagttaagt gcgcagaaag    1860
taatatcatg cgtcaatcgt atgtgaatgc tggtcgctat actgctgtcg attcgatact    1920
aacgccgcca tccagtgtcg aaaacgagct ctcgagaacc cttaatcgag tgtagccaga    1980
tctcaatgct acatcatcga aaagtctag aggccaaggc aaaagattc cttgattacg       2040 taagggagtt agaatcattt tgaataaaaa acacgctttt tcagttcgag tttatcatta    2100
tcaatactgc catttcaaag aatacgtaaa taattaatag tagtgatttt cctaacttta    2160
tttagtcaaa aaattagcct tttaattctg ctgtaacccg tacatgccca aaataggggg    2220
cgggttacac agaatatata acatcgtagg tgtctgggtg aacagtttat tcctggcatc    2280
cactaaatat aatggagccc gctttttaag ctggcatcca gaaaaaaaa gaatcccagc     2340 accaaaatat tgttttcttc accaaccatc agttcatagg tccattctct tagcgcaact    2400
acagagaaca ggggcacaaa caggcaaaaa acgggcacaa cctcaatgga gtgatgcaac    2460
ctgcctggag taaatgatga cacaaggcaa ttgacccacg catgtatcta tctcattttc    2520
```

```
ttacaccttc tattaccttc tgctctctct gatttggaaa aagctgaaaa aaaaggttga    2580
aaccagttcc ctgaaattat tcccctactt gactaataag tatataaaga cggtaggtat    2640
tgattgtaat tctgtaaatc tatttcttaa acttcttaaa ttctacttt atagttagtc    2700 ttttttttag ttttaaaaca ccaagaactt agtttcgaat aaacacacat aaacaaaaaa    2760
caaagagctc aaaacgggcg tgtggcgtag ttggtagcgc gttcccttag catgggaaag    2820
gtcatgagtt cgactcttat ctcgtccagg cattcagtac ggtcgtatat ggagatacg    2880 accgtactga atgccttgcg caagtggttt agtggtaaaa tccaacgttg ccatcgttgg    2940
gcccccggtt cgattccggg cttgcgcaat gaacttcagg gtcagcttgc gttgaccctg    3000
aagttcattc ggccggcatg gtcccagcct cctcgctggc gccggctggg caacatgctt    3060
cggcatggcg aatgggacac aggcccttt tcctttgtcg atatcatgta attagttatg    3120
tcacgcttac attcacgccc tccccccaca tccgctctaa ccgaaaagga aggagttaga    3180
caacctgaag tctaggtccc tatttatttt tttatagtta tgttagtatt aagaacgtta    3240
tttatatttc aaattttct tttttttctg tacaaacgcg tgtacgcatg taacattata    3300
ctgaaaacct tgcttgagaa ggttttggga caagcttacg tctcacggat cgtatatgcc    3360
gtagcgacaa tctaagaact atgcgaggac acgctagcag ctggtggtat tggcccatct    3420
ctatcggcga ctagattgta aatcattctt tatttaatct ctttctttaa ctactgctta    3480
aagtataatt tggtccgtag tttaataact atactaagcg taacaatgca tactgacatt    3540
ataagcctga acattacgag tttaagttgt atgtaggcgt tctgtaagag gttactgcgt    3600
aaattatcaa cgaatgcatt ggtgtatttg cgaaagctac ttcttttaac aagtatttac    3660
ataagaataa tggtgatctg ctcaactgat ttggtgataa ctctaactt tttagcaaca    3720 atttaaaaga taattcgaac atatataaca gtaggaagaa tttgtgtacg tcaaattaag    3780
ataatttagc attaccaaag ttattaacct aaacataaaa tatatatgag acacatgtgg    3840
aaatcgtatg aaacaactgt tatgaaactg acaagaatg                          3879
```

<210> SEQ ID NO 11
<211> LENGTH: 661
<212> TYPE: DNA
<213> ORGANISM: Sars-CoV-2

<400> SEQUENCE: 11

```
attaaaggtt tataccttcc caggtaacaa accaaccaac tttcgatctc ttgtagatct     60
gttctctaaa cgaactttaa aatctgtgtg gctgtcactc ggctgcatgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagcac atctaggttt    240
cgtccgggtg tgaccgaaag gtaagatgga gagccttgtc cctggtttca acgagaaaac    300
acacgtccaa ctcagtttgc ctgttttaca ggttcgcgac gtgctcgtac gtggctttgg    360
agactccgtg gaggaggtct tatcagaggc acgtcaacat cttaaagatg gcacttgtgg    420
cttagtagaa gttgaaaaag gcgttttgcc tcaacttgaa cagccctatg tgttcatcaa    480
acgttcggat gctcgaactg cacctcatgg tcatgttatg gttgagctgg tagcagaact    540
cgaaggcatt cagtacggtc gtagtggtga gacacttggt gtccttgtcc ctcatgtggg    600
cgaaatacca gtggcttacc gcaaggttct tcttcgtaag ctcgagtcta gaggaagcgg    660
a                                                                   661
```

<210> SEQ ID NO 12
<211> LENGTH: 714
<212> TYPE: DNA
<213> ORGANISM: Aequorea victoria

<400> SEQUENCE: 12

| | | | | | |
|---|---|---|---|---|---|
| atgagcaagg | gcgaggagct | gttcaccggg | gtggtgccca | tcctggtcga | gctggacggc | 60 |
| gacgtaaacg | gccacaagtt | cagcgtgtcc | ggcgagggcg | agggcgatgc | cacctacggc | 120 |
| aagctgaccc | tgaagttcat | ctgcaccacc | ggcaagctgc | ccgtgccctg | gcccaccctc | 180 |
| gtgaccaccc | tgacctacgg | cgtgcagtgc | ttcagccgct | accccgacca | catgaagcag | 240 |
| cacgacttct | tcaagtccgc | catgcccgaa | ggctacgtcc | aggagcgcac | catcttcttc | 300 |
| aaggacgacg | gcaactacaa | gacccgcgcc | gaggtgaagt | tcgagggcga | caccctggtg | 360 |
| aaccgcatcg | agctgaaggg | catcgacttc | aaggaggacg | gcaacatcct | ggggcacaag | 420 |
| ctggagtaca | actacaacag | ccacaacgtc | tatatcatgg | ccgacaagca | gaagaacggc | 480 |
| atcaaggtga | acttcaagat | ccgccacaac | atcgaggacg | gcagcgtgca | gctcgccgac | 540 |
| cactaccagc | agaacacccc | catcggcgac | ggccccgtgc | tgctgcccga | caaccactac | 600 |
| ctgagcaccc | agtccgccct | gagcaaagac | cccaacgaga | agcgcgatca | catggtcctg | 660 |
| ctggagttcg | tgaccgccgc | cgggatcact | cacggcatgg | acgagctgta | caag | 714 |

<210> SEQ ID NO 13
<211> LENGTH: 1434
<212> TYPE: DNA
<213> ORGANISM: Artificial
<220> FEATURE:
<223> OTHER INFORMATION: Nsp1-GFP fusion construct

<400> SEQUENCE: 13

| | | | | | |
|---|---|---|---|---|---|
| attaaaggtt | tataccttcc | caggtaacaa | accaaccaac | tttcgatctc | ttgtagatct | 60 |
| gttctctaaa | cgaactttaa | aatctgtgtg | gctgtcactc | ggctgcatgc | ttagtgcact | 120 |
| cacgcagtat | aattaataac | taattactgt | cgttgacagg | acacgagtaa | ctcgtctatc | 180 |
| ttctgcaggc | tgcttacggt | ttcgtccgtg | ttgcagccga | tcatcagcac | atctaggttt | 240 |
| cgtccgggtg | tgaccgaaag | gtaagatgga | gagccttgtc | cctggtttca | acgagaaaac | 300 |
| acacgtccaa | ctcagtttgc | ctgttttaca | ggttcgcgac | gtgctcgtac | gtggctttgg | 360 |
| agactccgtg | gaggaggtct | tatcagaggc | acgtcaacat | cttaaagatg | gcacttgtgg | 420 |
| cttagtagaa | gttgaaaaag | gcgttttgcc | tcaacttgaa | cagccctatg | tgttcatcaa | 480 |
| acgttcggat | gctcgaactg | cacctcatgg | tcatgttatg | gttgagctgg | tagcagaact | 540 |
| cgaaggcatt | cagtacggtc | gtagtggtga | cacttggt | gtccttgtcc | ctcatgtggg | 600 |
| cgaaatacca | gtggcttacc | gcaaggttct | tcttcgtaag | ctcgagtcta | ggaagcgg | 660 |
| agctactaac | ttcagcctgc | tgaagcaggc | tggagacgtg | gaggagaacc | ctggacctat | 720 |
| gagcaagggc | gaggagctgt | tcaccggggt | ggtgcccatc | ctggtcgagc | tggacggcga | 780 |
| cgtaaacggc | cacaagttca | gcgtgtccgg | cgagggcgag | ggcgatgcca | cctacggcaa | 840 |
| gctgaccctg | aagttcatct | gcaccaccgg | caagctgccc | gtgccctggc | ccaccctcgt | 900 |
| gaccaccctg | acctacggcg | tgcagtgctt | cagccgctac | cccgaccaca | tgaagcagca | 960 |
| cgacttcttc | aagtccgcca | tgcccgaagg | ctacgtccag | gagcgcacca | tcttcttcaa | 1020 |
| ggacgacggc | aactacaaga | cccgcgccga | ggtgaagttc | gagggcgaca | ccctggtgaa | 1080 |
| ccgcatcgag | ctgaagggca | tcgacttcaa | ggaggacggc | aacatcctgg | ggcacaagct | 1140 |

```
ggagtacaac tacaacagcc acaacgtcta tcatcatggcc gacaagcaga agaacggcat    1200
caaggtgaac ttcaagatcc gccacaacat cgaggacggc agcgtgcagc tcgccgacca    1260
ctaccagcag aacacccca tcggcgacgg ccccgtgctg ctgcccgaca ccactaccct    1320
gagcacccag tccgccctga gcaaagaccc caacgagaag cgcgatcaca tggtcctgct    1380
ggagttcgtg accgccgccg ggatcactca cggcatggac gagctgtaca agta          1434
```

```
<210> SEQ ID NO 14
<211> LENGTH: 26
<212> TYPE: PRT
<213> ORGANISM: Artificial
<220> FEATURE:
<223> OTHER INFORMATION: ACE2 Inhibitor - 1

<400> SEQUENCE: 14

Gly Asp Tyr Ser His Cys Ser Pro Leu Arg Tyr Tyr Pro Trp Trp Lys
1               5                   10                  15

Cys Thr Tyr Pro Asp Pro Glu Gly Gly Gly
            20                  25
```

```
<210> SEQ ID NO 15
<211> LENGTH: 26
<212> TYPE: PRT
<213> ORGANISM: Artificial
<220> FEATURE:
<223> OTHER INFORMATION: ACE2 Inhibitor - 2

<400> SEQUENCE: 15

Gly Asp Asp Asp Cys Gly Trp Ile Gly Phe Ala Asn Phe His Leu
1               5                   10                  15

Cys Leu His Gly Asp Pro Glu Gly Gly Gly
            20                  25
```

```
<210> SEQ ID NO 16
<211> LENGTH: 12
<212> TYPE: PRT
<213> ORGANISM: Artificial
<220> FEATURE:
<223> OTHER INFORMATION: Linker peptide

<400> SEQUENCE: 16

Gly Ser Ala Gly Ser Ala Ala Gly Ser Gly Glu Phe
1               5                   10
```

```
<210> SEQ ID NO 17
<211> LENGTH: 42
<212> TYPE: RNA
<213> ORGANISM: Artificial
<220> FEATURE:
<223> OTHER INFORMATION: SiRNA targeting GFP

<400> SEQUENCE: 17
augaacuuca ggucagcuu gcguugaccc ugaaguucau uc                          42
```

```
<210> SEQ ID NO 18
<211> LENGTH: 49
<212> TYPE: RNA
<213> ORGANISM: Artificial
<220> FEATURE:
<223> OTHER INFORMATION: SiRNA targeting nsp1 Sars-CoV2 gene

<400> SEQUENCE: 18
ggcauucagu acggucguau auuggagaua cgaccguacu gaaugccuu                  49
```

<210> SEQ ID NO 19
<211> LENGTH: 20
<212> TYPE: DNA
<213> ORGANISM: Artificial
<220> FEATURE:
<223> OTHER INFORMATION: Nsp1 Northern Blot probe

<400> SEQUENCE: 19
aggcattcag tacggtcgta                                              20

<210> SEQ ID NO 20
<211> LENGTH: 20
<212> TYPE: DNA
<213> ORGANISM: Artificial
<220> FEATURE:
<223> OTHER INFORMATION: qNsp1-5' probe

<400> SEQUENCE: 20
cgtacgtggc tttggagact                                              20

<210> SEQ ID NO 21
<211> LENGTH: 20
<212> TYPE: DNA
<213> ORGANISM: Artificial
<220> FEATURE:
<223> OTHER INFORMATION: qNsp1-3' probe

<400> SEQUENCE: 21
accatgaggt gcagttcgag                                              20

<210> SEQ ID NO 22
<211> LENGTH: 20
<212> TYPE: DNA
<213> ORGANISM: Artificial
<220> FEATURE:
<223> OTHER INFORMATION: qGen-5' probe

<400> SEQUENCE: 22
tgctcgacgt tgtcactgaa                                              20

<210> SEQ ID NO 23
<211> LENGTH: 20
<212> TYPE: DNA
<213> ORGANISM: Artificial
<220> FEATURE:
<223> OTHER INFORMATION: qGen-3' probe

<400> SEQUENCE: 23
gatgtttcgc ttggtggtcg                                              20

<210> SEQ ID NO 24
<211> LENGTH: 282
<212> TYPE: PRT
<213> ORGANISM: Saccharomyces cerevisiae

<400> SEQUENCE: 24

Met Ser Asp Arg Glu Gln Ser Ser Gly Asn Thr Ala Phe Glu Asn Pro
1               5                   10                  15

Lys Ala Leu Asp Ser Ser Glu Gly Glu Phe Ile Ser Glu Asn Asn Asp
            20                  25                  30

Gln Ser Arg His Ser Gln Glu Ser Ile Cys Lys Ile Tyr Thr Ala Gly
        35                  40                  45

Lys Asn Asn Glu Tyr Ile Tyr Ile Gly Arg Gln Lys Phe Leu Arg Asp
    50                  55                  60

```
Asp Leu Phe Glu Ala Phe Gly Thr Leu Asn Pro Gly Leu Ala Pro
 65                  70                  75                  80

Ala Pro Val His Lys Phe Ala Asn Pro Ala Pro Leu Gly Leu Ser Gly
                 85                  90                  95

Phe Ala Leu Thr Thr Phe Val Leu Ser Met Phe Asn Ala Arg Ala Gln
            100                 105                 110

Gly Ile Thr Ile Pro Asn Val Val Gly Cys Ala Met Phe Tyr Gly
            115                 120                 125

Gly Leu Val Gln Leu Ile Ala Gly Ile Trp Glu Ile Ala Leu Glu Asn
130                 135                 140

Thr Phe Gly Gly Thr Ala Leu Cys Ser Phe Gly Gly Phe Trp Leu Ser
145                 150                 155                 160

Phe Gly Ala Ile Tyr Ile Pro Trp Phe Gly Ile Leu Asp Ala Tyr Lys
                165                 170                 175

Asp Lys Glu Ser Asp Leu Gly Asn Ala Leu Gly Phe Tyr Leu Leu Gly
            180                 185                 190

Trp Ala Leu Phe Thr Phe Gly Leu Ser Val Cys Thr Met Lys Ser Thr
            195                 200                 205

Ile Met Phe Phe Ala Leu Phe Phe Leu Leu Ala Val Thr Phe Leu Leu
            210                 215                 220

Leu Ser Ile Ala Asn Phe Thr Gly Glu Val Gly Val Thr Arg Ala Gly
225                 230                 235                 240

Gly Val Leu Gly Val Ile Val Ala Phe Ile Ala Trp Tyr Asn Ala Tyr
                245                 250                 255

Ala Gly Ile Ala Thr Arg Gln Asn Ser Tyr Ile Met Val His Pro Phe
            260                 265                 270

Ala Leu Pro Ser Asn Asp Lys Val Phe Phe
            275                 280

<210> SEQ ID NO 25
<211> LENGTH: 263
<212> TYPE: PRT
<213> ORGANISM: Saccharomyces cerevisiae

<400> SEQUENCE: 25

Met Arg Asn Phe Phe Thr Leu Phe Phe Ala Ala Ile Phe Ser Leu Gly
1               5                   10                  15

Ala Leu Ile Leu Ala Ile Val Ala Cys Ala Gly Ser Thr Lys Asn Tyr
            20                  25                  30

Ser Pro Ile Asn Lys Ile Tyr Cys Ala Glu Leu Asp Leu Ser Gln Met
        35                  40                  45

Lys Val Ser Thr Val Leu Pro Ser Leu Ser Ser Ala Thr Leu Ser Ser
    50                  55                  60

Leu Gly Leu Pro Ser Tyr Ile Asn Ile Gly Leu Trp Ser Tyr Cys Thr
65                  70                  75                  80

Val Asp Ser Ser His Asn Ile Gln Ser Cys Ser Ser Pro His Gly Ile
                85                  90                  95

Gln Asn Phe Asn Leu Ser Ser Leu Val Tyr Asp Asn Ile Asn Asn Asn
            100                 105                 110

Glu Ala Leu Glu Leu Met Asp Ser Val Ala Ser Val Leu Pro Glu
            115                 120                 125

Lys Leu Lys Ser Lys Met Thr Tyr Tyr Asn Asn Leu Val Lys Cys Met
            130                 135                 140

Phe Ile Thr Ile Leu Ile Gly Ile Val Leu Thr Phe Val Asn Leu Val
```

```
                145                 150                 155                 160

Phe Asn Val Leu Arg Trp Ile Ile His Ile Arg Pro Leu Thr Trp Phe
                        165                 170                 175

Gly Ala Phe Phe Ser Phe Phe Ala Phe Ala Ala Leu Leu Val Ser Ile
                        180                 185                 190

Gly Ser Cys Leu Gly Thr Tyr Ser Tyr Ile Lys Tyr Ile Leu Lys His
                        195                 200                 205

Asn Tyr Ser Asp Tyr Gly Ile Ser Met Ser Ile Gly Arg Asn Tyr Gln
                210                 215                 220

Gly Leu Met Trp Gly Ala Val Gly Ala Leu Leu Asn Phe Ile Leu
        225                 230                 235                 240

Trp Cys Ser Val Arg Ser Arg Pro Thr Val Ile Tyr Ala Asn Ala Pro
                        245                 250                 255

Ile Glu Glu Lys Pro Leu Ile
                        260

<210> SEQ ID NO 26
<211> LENGTH: 448
<212> TYPE: PRT
<213> ORGANISM: Saccharomyces cerevisiae

<400> SEQUENCE: 26

Met Leu Ser Leu Lys Thr Leu Leu Cys Thr Leu Leu Thr Val Ser Ser
        1               5                   10                  15

Val Leu Ala Thr Pro Val Pro Ala Arg Asp Pro Ser Ser Ile Gln Phe
                        20                  25                  30

Val His Glu Glu Asn Lys Lys Arg Tyr Tyr Asp Tyr Asp His Gly Ser
                        35                  40                  45

Leu Gly Glu Pro Ile Arg Gly Val Asn Ile Gly Gly Trp Leu Leu Leu
                50                  55                  60

Glu Pro Tyr Ile Thr Pro Ser Leu Phe Glu Ala Phe Arg Thr Asn Asp
        65                  70                  75                  80

Asp Asn Asp Glu Gly Ile Pro Val Asp Glu Tyr His Phe Cys Gln Tyr
                        85                  90                  95

Leu Gly Lys Asp Leu Ala Lys Ser Arg Leu Gln Ser His Trp Ser Thr
                        100                 105                 110

Phe Tyr Gln Glu Gln Asp Phe Ala Asn Ile Ala Ser Gln Gly Phe Asn
                        115                 120                 125

Leu Val Arg Ile Pro Ile Gly Tyr Trp Ala Phe Gln Thr Leu Asp Asp
                130                 135                 140

Asp Pro Tyr Val Ser Gly Leu Gln Glu Ser Tyr Leu Asp Gln Ala Ile
        145                 150                 155                 160

Gly Trp Ala Arg Asn Asn Ser Leu Lys Val Trp Val Asp Leu His Gly
                        165                 170                 175

Ala Ala Gly Ser Gln Asn Gly Phe Asp Asn Ser Gly Leu Arg Asp Ser
                        180                 185                 190

Tyr Lys Phe Leu Glu Asp Ser Asn Leu Ala Val Thr Thr Asn Val Leu
                        195                 200                 205

Asn Tyr Ile Leu Lys Lys Tyr Ser Ala Glu Glu Tyr Leu Asp Thr Val
                210                 215                 220

Ile Gly Ile Glu Leu Ile Asn Glu Pro Leu Gly Pro Val Leu Asp Met
        225                 230                 235                 240

Asp Lys Met Lys Asn Asp Tyr Leu Ala Pro Ala Tyr Glu Tyr Leu Arg
                        245                 250                 255
```

```
Asn Asn Ile Lys Ser Asp Gln Val Ile Ile His Asp Ala Phe Gln
                260                 265                 270

Pro Tyr Asn Tyr Trp Asp Asp Phe Met Thr Glu Asn Asp Gly Tyr Trp
            275                 280                 285

Gly Val Thr Ile Asp His His His Tyr Gln Val Phe Ala Ser Asp Gln
        290                 295                 300

Leu Glu Arg Ser Ile Asp Glu His Ile Lys Val Ala Cys Glu Trp Gly
305                 310                 315                 320

Thr Gly Val Leu Asn Glu Ser His Trp Thr Val Cys Gly Glu Phe Ala
                325                 330                 335

Ala Ala Leu Thr Asp Cys Thr Lys Trp Leu Asn Ser Val Gly Phe Gly
            340                 345                 350

Ala Arg Tyr Asp Gly Ser Trp Val Asn Gly Asp Gln Thr Ser Ser Tyr
        355                 360                 365

Ile Gly Ser Cys Ala Asn Asn Asp Asp Ile Ala Tyr Trp Ser Asp Glu
    370                 375                 380

Arg Lys Glu Asn Thr Arg Arg Tyr Val Glu Ala Gln Leu Asp Ala Phe
385                 390                 395                 400

Glu Met Arg Gly Gly Trp Ile Ile Trp Cys Tyr Lys Thr Glu Ser Ser
                405                 410                 415

Leu Glu Trp Asp Ala Gln Arg Leu Met Phe Asn Gly Leu Phe Pro Gln
            420                 425                 430

Pro Leu Thr Asp Arg Lys Tyr Pro Asn Gln Cys Gly Thr Ile Ser Asn
        435                 440                 445

<210> SEQ ID NO 27
<211> LENGTH: 313
<212> TYPE: PRT
<213> ORGANISM: Saccharomyces cerevisiae

<400> SEQUENCE: 27

Met Arg Phe Ser Thr Thr Leu Ala Thr Ala Ala Thr Ala Leu Phe Phe
1               5                   10                  15

Thr Ala Ser Gln Val Ser Ala Ile Gly Glu Leu Ala Phe Asn Leu Gly
                20                  25                  30

Val Lys Asn Asn Asp Gly Thr Cys Lys Ser Thr Ser Asp Tyr Glu Thr
            35                  40                  45

Glu Leu Gln Ala Leu Lys Ser Tyr Thr Ser Thr Val Lys Val Tyr Ala
        50                  55                  60

Ala Ser Asp Cys Asn Thr Leu Gln Asn Leu Gly Pro Ala Ala Glu Ala
65                  70                  75                  80

Glu Gly Phe Thr Ile Phe Val Gly Val Trp Pro Thr Asp Asp Ser His
                85                  90                  95

Tyr Ala Ala Glu Lys Ala Ala Leu Gln Thr Tyr Leu Pro Lys Ile Lys
            100                 105                 110

Glu Ser Thr Val Ala Gly Phe Leu Val Gly Ser Glu Ala Leu Tyr Arg
        115                 120                 125

Asn Asp Leu Thr Ala Ser Gln Leu Ser Asp Lys Ile Asn Asp Val Arg
    130                 135                 140

Ser Val Val Ala Asp Ile Ser Asp Ser Asp Gly Lys Ser Tyr Ser Gly
145                 150                 155                 160

Lys Gln Val Gly Thr Val Asp Ser Trp Asn Val Leu Val Ala Gly Tyr
                165                 170                 175

Asn Ser Ala Val Ile Glu Ala Ser Asp Phe Val Met Ala Asn Ala Phe
            180                 185                 190
```

Ser Tyr Trp Gln Gly Gln Thr Met Gln Asn Ala Ser Tyr Ser Phe Phe
            195                 200                 205

Asp Asp Ile Met Gln Ala Leu Gln Val Ile Gln Ser Thr Lys Gly Ser
210                 215                 220

Thr Asp Ile Thr Phe Trp Val Gly Glu Thr Gly Trp Pro Thr Asp Gly
225                 230                 235                 240

Thr Asn Phe Glu Ser Ser Tyr Pro Ser Val Asp Asn Ala Lys Gln Phe
            245                 250                 255

Trp Lys Glu Gly Ile Cys Ser Met Arg Ala Trp Gly Val Asn Val Ile
            260                 265                 270

Val Phe Glu Ala Phe Asp Glu Asp Trp Lys Pro Asn Thr Ser Gly Thr
            275                 280                 285

Ser Asp Val Glu Lys His Trp Gly Val Phe Thr Ser Ser Asp Asn Leu
            290                 295                 300

Lys Tyr Ser Leu Asp Cys Asp Phe Ser
305                 310

<210> SEQ ID NO 28
<211> LENGTH: 559
<212> TYPE: PRT
<213> ORGANISM: Saccharomyces cerevisiae

<400> SEQUENCE: 28

Met Leu Phe Lys Ser Leu Ser Lys Leu Ala Thr Ala Ala Phe Phe
1               5                   10                  15

Ala Gly Val Ala Thr Ala Asp Asp Val Pro Ala Ile Glu Val Val Gly
                20                  25                  30

Asn Lys Phe Phe Tyr Ser Asn Asn Gly Ser Gln Phe Tyr Ile Arg Gly
            35                  40                  45

Val Ala Tyr Gln Ala Asp Thr Ala Asn Glu Thr Ser Gly Ser Thr Val
    50                  55                  60

Asn Asp Pro Leu Ala Asn Tyr Glu Ser Cys Ser Arg Asp Ile Pro Tyr
65                  70                  75                  80

Leu Lys Lys Leu Asn Thr Asn Val Ile Arg Val Tyr Ala Ile Asn Thr
                85                  90                  95

Thr Leu Asp His Ser Glu Cys Met Lys Ala Leu Asn Asp Ala Asp Ile
            100                 105                 110

Tyr Val Ile Ala Asp Leu Ala Ala Pro Ala Thr Ser Ile Asn Arg Asp
        115                 120                 125

Asp Pro Thr Trp Thr Val Asp Leu Phe Asn Ser Tyr Lys Thr Val Val
130                 135                 140

Asp Thr Phe Ala Asn Tyr Thr Asn Val Leu Gly Phe Phe Ala Gly Asn
145                 150                 155                 160

Glu Val Thr Asn Asn Tyr Thr Asn Thr Asp Ala Ser Ala Phe Val Lys
                165                 170                 175

Ala Ala Ile Arg Asp Val Arg Gln Tyr Ile Ser Asp Lys Asn Tyr Arg
            180                 185                 190

Lys Ile Pro Val Gly Tyr Ser Ser Asn Asp Asp Glu Asp Thr Arg Val
        195                 200                 205

Lys Met Thr Asp Tyr Phe Ala Cys Gly Asp Asp Val Lys Ala Asp
210                 215                 220

Phe Tyr Gly Ile Asn Met Tyr Glu Trp Cys Gly Lys Ser Asp Phe Lys
225                 230                 235                 240

Thr Ser Gly Tyr Ala Asp Arg Thr Ala Glu Phe Lys Asn Leu Ser Ile

```
            245                 250                 255
Pro Val Phe Phe Ser Glu Tyr Gly Cys Asn Glu Val Thr Pro Arg Leu
            260                 265                 270

Phe Thr Glu Val Glu Ala Leu Tyr Gly Ser Asn Met Thr Asp Val Trp
        275                 280                 285

Ser Gly Gly Ile Val Tyr Met Tyr Phe Glu Glu Thr Asn Lys Tyr Gly
    290                 295                 300

Leu Val Ser Ile Asp Gly Asn Asp Val Lys Thr Leu Asp Asp Phe Asn
305                 310                 315                 320

Asn Tyr Ser Ser Glu Ile Asn Lys Ile Ser Pro Thr Ser Ala Asn Thr
                325                 330                 335

Lys Ser Tyr Ser Ala Thr Thr Ser Asp Val Ala Cys Pro Ala Thr Gly
            340                 345                 350

Lys Tyr Trp Ser Ala Ala Thr Glu Leu Pro Pro Thr Pro Asn Gly Gly
        355                 360                 365

Leu Cys Ser Cys Met Asn Ala Ala Asn Ser Cys Val Val Ser Asp Asp
    370                 375                 380

Val Asp Ser Asp Asp Tyr Glu Thr Leu Phe Asn Trp Ile Cys Asn Glu
385                 390                 395                 400

Val Asp Cys Ser Gly Ile Ser Ala Asn Gly Thr Ala Gly Lys Tyr Gly
                405                 410                 415

Ala Tyr Ser Phe Cys Thr Pro Lys Glu Gln Leu Ser Phe Val Met Asn
            420                 425                 430

Leu Tyr Tyr Glu Lys Ser Gly Gly Ser Lys Ser Asp Cys Ser Phe Ser
        435                 440                 445

Gly Ser Ala Thr Leu Gln Thr Ala Thr Gln Ala Ser Cys Ser Ser
    450                 455                 460

Ala Leu Lys Glu Ile Gly Ser Met Gly Thr Asn Ser Ala Ser Gly Ser
465                 470                 475                 480

Val Asp Leu Gly Ser Gly Thr Glu Ser Ser Thr Ala Ser Ser Asn Ala
                485                 490                 495

Ser Gly Ser Ser Ser Lys Ser Asn Ser Gly Ser Ser Gly Ser Ser Ser
            500                 505                 510

Ser Ser Ser Ser Ser Ser Ala Ser Ser Ser Ser Ser Lys Lys Asn
        515                 520                 525

Ala Ala Thr Asn Val Lys Ala Asn Leu Ala Gln Val Val Phe Thr Ser
    530                 535                 540

Ile Ile Ser Leu Ser Ile Ala Ala Gly Val Gly Phe Ala Leu Val
545                 550                 555

<210> SEQ ID NO 29
<211> LENGTH: 375
<212> TYPE: PRT
<213> ORGANISM: Saccharomyces cerevisiae

<400> SEQUENCE: 29

Met Ile Phe Asn Pro Val Ile Ser Asn His Lys Leu Ser His Tyr Ile
1               5                   10                  15

His Val Phe Cys Thr Phe Thr Thr Phe Cys Ile Leu Gly Thr Glu Thr
            20                  25                  30

Arg Gln Ala Ile Thr Ala Leu Ser Thr Tyr Thr Pro Ala Phe Val Thr
        35                  40                  45

Ala Pro Thr Val Leu Trp Ser Asn Cys Ser Ser Cys Met Leu Met Gly
    50                  55                  60
```

```
Ile Met Gln Ser Leu Asn Ala Tyr Thr Trp Met Lys Asp His Gln Val
 65                  70                  75                  80

Leu Phe Leu Gly Val Thr Thr Gly Tyr Cys Gly Ala Leu Ser Ser Phe
                 85                  90                  95

Ser Ser Met Leu Leu Glu Met Phe Glu His Ser Thr Asn Leu Thr Asn
            100                 105                 110

Gly Asn Ile Ala Asn His Thr Lys Leu Pro Asn Arg Ala Tyr Gly Ile
        115                 120                 125

Met Glu Phe Leu Ser Val Leu Leu Val His Leu Met Val Ser Met Gly
    130                 135                 140

Ser Leu Ile Phe Gly Arg Gln Leu Gly Lys Glu Val Ile Val Ala Tyr
145                 150                 155                 160

Gly Ser Ser Ser Phe Ser Lys Pro Tyr Thr Pro Pro Ser Asp Thr Val
                165                 170                 175

Lys Glu Asn Ala Gly Asp Val Asp Thr Gln Glu Met Glu Lys Asn Ile
            180                 185                 190

Leu Glu Phe Lys Phe Lys Thr Pro Ala Pro Phe Lys Lys Phe Phe
        195                 200                 205

Asp Ile Val Asp Lys Leu Ala Tyr Ala Leu Ala Phe Pro Leu Ile Ile
    210                 215                 220

Leu Phe Val Val Leu Cys Ala Tyr Tyr Glu Asn Tyr Ser Arg Gly Lys
225                 230                 235                 240

Trp Thr Leu Pro Cys Leu Phe Gly Ile Phe Ala Gly Phe Leu Arg Tyr
                245                 250                 255

Trp Leu Ala Glu Met Phe Asn Lys Thr Asn Lys Lys Phe Pro Leu Gly
            260                 265                 270

Thr Phe Leu Ala Asn Val Phe Ala Thr Leu Leu Ile Gly Ile Phe Thr
        275                 280                 285

Met Val Gln Arg Gly Lys Lys His Phe Ser Thr Asp Val Pro Ile Val
    290                 295                 300

Asn Ser Leu Asn Ser Cys His Ile Val Ser Ala Leu Ile Ser Gly Phe
305                 310                 315                 320

Cys Gly Thr Leu Ser Thr Ile Ser Thr Phe Ile Asn Glu Gly Tyr Lys
                325                 330                 335

Leu Ser Phe Ile Asn Met Leu Ile Tyr Tyr Thr Val Ser Ile Ala Ile
            340                 345                 350

Ser Tyr Cys Leu Leu Val Ile Thr Leu Gly Ser Tyr Ala Trp Thr Arg
        355                 360                 365

Gly Leu Thr Asn Pro Ile Cys
    370                 375

<210> SEQ ID NO 30
<211> LENGTH: 636
<212> TYPE: PRT
<213> ORGANISM: Saccharomyces cerevisiae

<400> SEQUENCE: 30

Met Thr Asn Ala Leu Leu Ser Ile Ala Val Leu Leu Phe Ser Met Leu
  1               5                  10                  15

Ser Leu Ala Gln Ala Glu Thr His Thr Phe Asn Trp Thr Thr Gly Trp
                 20                  25                  30

Asp Tyr Arg Asn Val Asp Gly Leu Lys Ser Arg Pro Val Ile Thr Cys
             35                  40                  45

Asn Gly Gln Phe Pro Trp Pro Asp Ile Thr Val Asn Lys Gly Asp Arg
         50                  55                  60
```

```
Val Gln Ile Tyr Leu Thr Asn Gly Met Asn Asn Thr Asn Thr Ser Met
 65                  70                  75                  80

His Phe His Gly Leu Phe Gln Asn Gly Thr Ala Ser Met Asp Gly Val
                 85                  90                  95

Pro Phe Leu Thr Gln Cys Pro Ile Ala Pro Gly Ser Thr Met Leu Tyr
            100                 105                 110

Asn Phe Thr Val Asp Tyr Asn Val Gly Thr Tyr Trp Tyr His Ser His
            115                 120                 125

Thr Asp Gly Gln Tyr Glu Asp Gly Met Lys Gly Leu Phe Ile Ile Lys
            130                 135                 140

Asp Asp Ser Phe Pro Tyr Asp Tyr Asp Glu Leu Ser Leu Ser Leu
145                 150                 155                 160

Ser Glu Trp Tyr His Asp Leu Val Thr Asp Leu Thr Lys Ser Phe Met
                165                 170                 175

Ser Val Tyr Asn Pro Thr Gly Ala Glu Pro Ile Pro Gln Asn Leu Ile
            180                 185                 190

Val Asn Asn Thr Met Asn Leu Thr Trp Glu Val Gln Pro Asp Thr Thr
            195                 200                 205

Tyr Leu Leu Arg Ile Val Asn Val Gly Gly Phe Val Ser Gln Tyr Phe
210                 215                 220

Trp Ile Glu Asp His Glu Met Thr Val Val Glu Ile Asp Gly Ile Thr
225                 230                 235                 240

Thr Glu Lys Asn Val Thr Asp Met Leu Tyr Ile Thr Val Ala Gln Arg
                245                 250                 255

Tyr Thr Val Leu Val His Thr Lys Asn Asp Thr Asp Lys Asn Phe Ala
            260                 265                 270

Ile Met Gln Lys Phe Asp Asp Thr Met Leu Asp Val Ile Pro Ser Asp
            275                 280                 285

Leu Gln Leu Asn Ala Thr Ser Tyr Met Val Tyr Asn Lys Thr Ala Ala
            290                 295                 300

Leu Pro Thr Gln Asn Tyr Val Asp Ser Ile Asp Asn Phe Leu Asp Asp
305                 310                 315                 320

Phe Tyr Leu Gln Pro Tyr Glu Lys Glu Ala Ile Tyr Gly Glu Pro Asp
            325                 330                 335

His Val Ile Thr Val Asp Val Met Asp Asn Leu Lys Asn Gly Val
            340                 345                 350

Asn Tyr Ala Phe Phe Asn Asn Ile Thr Tyr Thr Ala Pro Lys Val Pro
            355                 360                 365

Thr Leu Met Thr Val Leu Ser Ser Gly Asp Gln Ala Asn Asn Ser Glu
            370                 375                 380

Ile Tyr Gly Ser Asn Thr His Thr Phe Ile Leu Glu Lys Asp Glu Ile
385                 390                 395                 400

Val Glu Ile Val Leu Asn Asn Gln Asp Thr Gly Thr His Pro Phe His
                405                 410                 415

Leu His Gly His Ala Phe Gln Thr Ile Gln Arg Asp Arg Thr Tyr Asp
            420                 425                 430

Asp Ala Leu Gly Glu Val Pro His Ser Phe Asp Pro Asp Asn His Pro
            435                 440                 445

Ala Phe Pro Glu Tyr Pro Met Arg Arg Asp Thr Leu Tyr Val Arg Pro
            450                 455                 460

Gln Ser Asn Phe Val Ile Arg Phe Lys Ala Asp Asn Pro Gly Val Trp
465                 470                 475                 480
```

```
Phe Phe His Cys His Ile Glu Trp His Leu Leu Gln Gly Leu Gly Leu
            485                 490                 495

Val Leu Val Glu Asp Pro Phe Gly Ile Gln Asp Ala His Ser Gln Gln
        500                 505                 510

Leu Ser Glu Asn His Leu Glu Val Cys Gln Ser Cys Ser Val Ala Thr
    515                 520                 525

Glu Gly Asn Ala Ala Ala Asn Thr Leu Asp Leu Thr Asp Leu Thr Gly
530                 535                 540

Glu Asn Val Gln His Ala Phe Ile Pro Thr Gly Phe Thr Lys Lys Gly
545                 550                 555                 560

Ile Ile Ala Met Thr Phe Ser Cys Phe Ala Gly Ile Leu Gly Ile Ile
                565                 570                 575

Thr Ile Ala Ile Tyr Gly Met Met Asp Met Glu Asp Ala Thr Glu Lys
            580                 585                 590

Val Ile Arg Asp Leu His Val Asp Pro Glu Val Leu Leu Asn Glu Val
        595                 600                 605

Asp Glu Asn Glu Glu Arg Gln Val Asn Glu Asp Arg His Ser Thr Glu
    610                 615                 620

Lys His Gln Phe Leu Thr Lys Ala Lys Arg Phe Phe
625                 630                 635

<210> SEQ ID NO 31
<211> LENGTH: 507
<212> TYPE: PRT
<213> ORGANISM: Saccharomyces cerevisiae

<400> SEQUENCE: 31

Met Lys Val Leu Asp Leu Leu Thr Val Leu Ser Ala Ser Ser Leu Leu
1               5                   10                  15

Ser Thr Phe Ala Ala Ala Glu Ser Thr Ala Thr Ala Asp Ser Thr Thr
            20                  25                  30

Ala Ala Ser Ser Thr Ala Ser Cys Asn Pro Leu Lys Thr Thr Gly Cys
        35                  40                  45

Thr Pro Asp Thr Ala Leu Ala Thr Ser Phe Ser Glu Asp Phe Ser Ser
    50                  55                  60

Ser Ser Lys Trp Phe Thr Asp Leu Lys His Ala Gly Glu Ile Lys Tyr
65                  70                  75                  80

Gly Ser Asp Gly Leu Ser Met Thr Leu Ala Lys Arg Tyr Asp Asn Pro
                85                  90                  95

Ser Leu Lys Ser Asn Phe Tyr Ile Met Tyr Gly Lys Leu Glu Val Ile
            100                 105                 110

Leu Lys Ala Ala Asn Gly Thr Gly Ile Val Ser Ser Phe Tyr Leu Gln
        115                 120                 125

Ser Asp Asp Leu Asp Glu Ile Asp Ile Glu Trp Val Gly Gly Asp Asn
    130                 135                 140

Thr Gln Phe Gln Ser Asn Phe Phe Ser Lys Gly Asp Thr Thr Thr Tyr
145                 150                 155                 160

Asp Arg Gly Glu Phe His Gly Val Asp Thr Pro Thr Asp Lys Phe His
                165                 170                 175

Asn Tyr Thr Leu Asp Trp Ala Met Asp Lys Thr Thr Tyr Leu Asp
            180                 185                 190

Gly Glu Ser Val Arg Val Leu Ser Asn Thr Ser Ser Glu Gly Tyr Pro
        195                 200                 205

Gln Ser Pro Met Tyr Leu Met Met Gly Ile Trp Ala Gly Gly Asp Pro
    210                 215                 220
```

Asp Asn Ala Ala Gly Thr Ile Glu Trp Ala Gly Gly Glu Thr Asn Tyr
225                 230                 235                 240

Asn Asp Ala Pro Phe Thr Met Tyr Ile Glu Lys Val Ile Val Thr Asp
            245                 250                 255

Tyr Ser Thr Gly Lys Lys Tyr Thr Tyr Gly Asp Gln Ser Gly Ser Trp
        260                 265                 270

Glu Ser Ile Glu Ala Asp Gly Gly Ser Ile Tyr Gly Arg Tyr Asp Gln
    275                 280                 285

Ala Gln Glu Asp Phe Ala Val Leu Ala Asn Gly Gly Ser Ile Ser Ser
        290                 295                 300

Ser Ser Thr Ser Ser Ser Thr Val Ser Ser Ala Ser Ser Thr Val
305                 310                 315                 320

Ser Ser Ser Val Ser Ser Thr Val Ser Ser Ala Ser Ser Thr Val
                325                 330                 335

Ser Ser Ser Val Ser Ser Thr Val Ser Ser Ser Ser Val Ser Ser
                340                 345                 350

Ser Ser Ser Thr Ser Pro Ser Ser Thr Ala Thr Ser Ser Lys Thr
            355                 360                 365

Leu Ala Ser Ser Val Thr Thr Ser Ser Ile Ser Ser Phe Glu
370                 375                 380

Lys Gln Ser Ser Ser Ser Lys Lys Thr Val Ala Ser Ser Thr
385                 390                 395                 400

Ser Glu Ser Ile Ile Ser Ser Thr Lys Thr Pro Ala Thr Val Ser Ser
            405                 410                 415

Thr Thr Arg Ser Thr Val Ala Pro Thr Thr Gln Gln Ser Ser Val Ser
        420                 425                 430

Ser Asp Ser Pro Val Gln Asp Lys Gly Gly Val Ala Thr Ser Ser Asn
        435                 440                 445

Asp Val Thr Ser Ser Thr Thr Gln Ile Ser Ser Lys Tyr Thr Ser Thr
        450                 455                 460

Ile Gln Ser Ser Ser Ser Glu Ala Ser Ser Thr Asn Ser Val Gln Ile
465                 470                 475                 480

Ser Asn Gly Ala Asp Leu Ala Gln Ser Leu Pro Arg Glu Gly Lys Leu
                485                 490                 495

Phe Ser Val Leu Val Ala Leu Leu Ala Leu Leu
            500                 505

<210> SEQ ID NO 32
<211> LENGTH: 53
<212> TYPE: PRT
<213> ORGANISM: Saccharomyces cerevisiae

<400> SEQUENCE: 32

Met Val Gln Tyr Ala Pro Phe Leu Leu Gly Lys Phe Ser Asp Pro Leu
1               5                   10                  15

Leu Ala Ile Met Val Gly Cys Leu Ser Tyr Tyr Val Tyr Glu Arg Lys
            20                  25                  30

Met Gly Arg Pro Gln Gly His His Leu His Glu Leu Ile Lys Lys Arg
        35                  40                  45

Trp Asp Asp Arg Lys
    50

<210> SEQ ID NO 33
<211> LENGTH: 302
<212> TYPE: PRT

<213> ORGANISM: Saccharomyces cerevisiae

<400> SEQUENCE: 33

Met Val Lys Val Trp Asn Ile Val Leu Arg Leu Val Leu Leu Phe
1               5                   10                  15

Leu Ala Gly Asn Thr Leu Leu Ile Leu Met Ile Ile Ser Gly Ala
            20                  25                  30

Thr Asp His Tyr Pro Val Asn Arg Phe Tyr Trp Val Gln Gly Asn Thr
            35                  40                  45

Thr Gly Ile Pro Asn Ala Gly Asp Glu Thr Arg Trp Thr Phe Trp Gly
    50                  55                  60

Ala Cys Leu Gln Asp Lys Asp Gly Ser Asp Thr Cys Thr Ser Asn Leu
65                  70                  75                  80

Ala Pro Ala Tyr Pro Ile Ser Pro Val Asp Asn Phe Asn Thr His Ile
                85                  90                  95

Asn Val Pro His Gln Phe Ile Ser Lys Arg Asp Ala Phe Tyr Tyr Leu
            100                 105                 110

Thr Arg Phe Ser Phe Cys Phe Trp Ile Ala Leu Ala Phe Val Gly
            115                 120                 125

Val Ser Phe Ile Leu Tyr Val Leu Thr Trp Cys Ser Lys Met Leu Ser
130                 135                 140

Glu Met Val Leu Ile Leu Met Ser Phe Gly Phe Val Phe Asn Thr Ala
145                 150                 155                 160

Ala Val Val Leu Gln Thr Ala Ala Ser Ala Met Ala Lys Asn Ala Phe
                165                 170                 175

His Asp Asp His Arg Ser Ala Gln Leu Gly Ala Ser Met Met Gly Met
            180                 185                 190

Ala Trp Ala Ser Val Phe Leu Cys Ile Val Glu Phe Ile Leu Leu Val
        195                 200                 205

Phe Trp Ser Val Arg Ala Arg Leu Ala Ser Thr Tyr Ser Ile Asp Asn
210                 215                 220

Ser Arg Tyr Arg Thr Ser Ser Arg Trp Asn Pro Phe His Arg Glu Lys
225                 230                 235                 240

Glu Gln Ala Thr Asp Pro Ile Leu Thr Ala Thr Gly Pro Glu Asp Met
                245                 250                 255

Gln Gln Ser Ala Ser Ile Val Gly Pro Ser Ser Asn Ala Asn Pro Val
            260                 265                 270

Thr Ala Thr Ala Ala Thr Glu Asn Gln Pro Lys Gly Ile Asn Phe Phe
        275                 280                 285

Thr Ile Arg Lys Ser His Glu Arg Pro Asp Asp Val Ser Val
290                 295                 300

<210> SEQ ID NO 34
<211> LENGTH: 805
<212> TYPE: PRT
<213> ORGANISM: Homo sapiens

<400> SEQUENCE: 34

Met Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn

```
            50                  55                  60
Ala Gly Asp Lys Trp Ser Ala Phe Leu Lys Glu Gln Ser Thr Leu Ala
 65                  70                  75                  80

Gln Met Tyr Pro Leu Gln Glu Ile Gln Asn Leu Thr Val Lys Leu Gln
                     85                  90                  95

Leu Gln Ala Leu Gln Gln Asn Gly Ser Ser Val Leu Ser Glu Asp Lys
                100                 105                 110

Ser Lys Arg Leu Asn Thr Ile Leu Asn Thr Met Ser Thr Ile Tyr Ser
                115                 120                 125

Thr Gly Lys Val Cys Asn Pro Asp Asn Pro Gln Glu Cys Leu Leu Leu
                130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
                195                 200                 205

Val Asn Gly Val Asp Gly Tyr Asp Tyr Ser Arg Gly Gln Leu Ile Glu
                210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
                275                 280                 285

Pro Asn Ile Asp Val Thr Asp Ala Met Val Asp Gln Ala Trp Asp Ala
                290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
                435                 440                 445

Thr Leu Pro Phe Thr Tyr Met Leu Glu Lys Trp Arg Trp Met Val Phe
                450                 455                 460

Lys Gly Glu Ile Pro Lys Asp Gln Trp Met Lys Lys Trp Trp Glu Met
465                 470                 475                 480
```

Lys Arg Glu Ile Val Gly Val Glu Pro Val His Asp Glu Thr
                485             490             495

Tyr Cys Asp Pro Ala Ser Leu Phe His Val Ser Asn Asp Tyr Ser Phe
                500             505             510

Ile Arg Tyr Tyr Thr Arg Thr Leu Tyr Gln Phe Gln Phe Gln Glu Ala
                515             520             525

Leu Cys Gln Ala Ala Lys His Glu Gly Pro Leu His Lys Cys Asp Ile
                530             535             540

Ser Asn Ser Thr Glu Ala Gly Gln Lys Leu Phe Asn Met Leu Arg Leu
545             550             555             560

Gly Lys Ser Glu Pro Trp Thr Leu Ala Leu Glu Asn Val Val Gly Ala
                565             570             575

Lys Asn Met Asn Val Arg Pro Leu Leu Asn Tyr Phe Glu Pro Leu Phe
                580             585             590

Thr Trp Leu Lys Asp Gln Asn Lys Asn Ser Phe Val Gly Trp Ser Thr
                595             600             605

Asp Trp Ser Pro Tyr Ala Asp Gln Ser Ile Lys Val Arg Ile Ser Leu
                610             615             620

Lys Ser Ala Leu Gly Asp Lys Ala Tyr Glu Trp Asn Asp Asn Glu Met
625             630             635             640

Tyr Leu Phe Arg Ser Ser Val Ala Tyr Ala Met Arg Gln Tyr Phe Leu
                645             650             655

Lys Val Lys Asn Gln Met Ile Leu Phe Gly Glu Glu Asp Val Arg Val
                660             665             670

Ala Asn Leu Lys Pro Arg Ile Ser Phe Asn Phe Val Thr Ala Pro
                675             680             685

Lys Asn Val Ser Asp Ile Ile Pro Arg Thr Glu Val Glu Lys Ala Ile
                690             695             700

Arg Met Ser Arg Ser Arg Ile Asn Asp Ala Phe Arg Leu Asn Asp Asn
705             710             715             720

Ser Leu Glu Phe Leu Gly Ile Gln Pro Thr Leu Gly Pro Pro Asn Gln
                725             730             735

Pro Pro Val Ser Ile Trp Leu Ile Val Phe Gly Val Val Met Gly Val
                740             745             750

Ile Val Val Gly Ile Val Ile Leu Ile Phe Thr Gly Ile Arg Asp Arg
                755             760             765

Lys Lys Lys Asn Lys Ala Arg Ser Gly Glu Asn Pro Tyr Ala Ser Ile
                770             775             780

Asp Ile Ser Lys Gly Glu Asn Asn Pro Gly Phe Gln Asn Thr Asp Asp
785             790             795             800

Val Gln Thr Ser Phe
                805

<210> SEQ ID NO 35
<211> LENGTH: 923
<212> TYPE: PRT
<213> ORGANISM: Homo sapiens

<400> SEQUENCE: 35

Met Glu Arg Gly Leu Pro Leu Leu Cys Ala Val Leu Ala Leu Val Leu
1               5               10              15

Ala Pro Ala Gly Ala Phe Arg Asn Asp Lys Cys Gly Asp Thr Ile Lys
                20              25              30

Ile Glu Ser Pro Gly Tyr Leu Thr Ser Pro Gly Tyr Pro His Ser Tyr

```
                35                  40                  45
His Pro Ser Glu Lys Cys Glu Trp Leu Ile Gln Ala Pro Asp Pro Tyr
 50                  55                  60

Gln Arg Ile Met Ile Asn Phe Asn Pro His Phe Asp Leu Glu Asp Arg
 65                  70                  75                  80

Asp Cys Lys Tyr Asp Tyr Val Glu Val Phe Asp Gly Glu Asn Glu Asn
                 85                  90                  95

Gly His Phe Arg Gly Lys Phe Cys Gly Lys Ile Ala Pro Pro Pro Val
                100                 105                 110

Val Ser Ser Gly Pro Phe Leu Phe Ile Lys Phe Val Ser Asp Tyr Glu
            115                 120                 125

Thr His Gly Ala Gly Phe Ser Ile Arg Tyr Glu Ile Phe Lys Arg Gly
130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Val Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
            195                 200                 205

Asp Arg Leu Glu Ile Trp Asp Gly Phe Pro Asp Val Gly Pro His Ile
210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Leu Gly Met Glu Ser Gly Glu Ile His Ser
            275                 280                 285

Asp Gln Ile Thr Ala Ser Ser Gln Tyr Ser Thr Asn Trp Ser Ala Glu
290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Val Ser Ser Asn Gly Glu Asp
            355                 360                 365

Trp Ile Thr Ile Lys Glu Gly Asn Lys Pro Val Leu Phe Gln Gly Asn
370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415

Met Arg Phe Glu Val Tyr Gly Cys Lys Ile Thr Asp Tyr Pro Cys Ser
            420                 425                 430

Gly Met Leu Gly Met Val Ser Gly Leu Ile Ser Asp Ser Gln Ile Thr
            435                 440                 445

Ser Ser Asn Gln Gly Asp Arg Asn Trp Met Pro Glu Asn Ile Arg Leu
450                 455                 460
```

```
Val Thr Ser Arg Ser Gly Trp Ala Leu Pro Pro Ala Pro His Ser Tyr
465                 470                 475                 480

Ile Asn Glu Trp Leu Gln Ile Asp Leu Gly Glu Lys Ile Val Arg
                485                 490                 495

Gly Ile Ile Ile Gln Gly Gly Lys His Arg Glu Asn Lys Val Phe Met
                500                 505                 510

Arg Lys Phe Lys Ile Gly Tyr Ser Asn Asn Gly Ser Asp Trp Lys Met
            515                 520                 525

Ile Met Asp Asp Ser Lys Arg Lys Ala Lys Ser Phe Glu Gly Asn Asn
530                 535                 540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Leu Val Asp Glu Cys Asp Asp Gln Ala
                595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Ala Ile Gly His Gln Gly Asp His Trp Lys Glu Gly Arg Val
                755                 760                 765

Leu Leu His Lys Ser Leu Lys Leu Tyr Gln Val Ile Phe Glu Gly Glu
            770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
        850                 855                 860

Ser Ala Leu Gly Val Leu Leu Gly Ala Val Cys Gly Val Val Leu Tyr
865                 870                 875                 880
```

```
Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Asp
            900                 905                 910

Lys Leu Asn Thr Gln Ser Thr Tyr Ser Glu Ala
        915                 920

<210> SEQ ID NO 36
<211> LENGTH: 232
<212> TYPE: PRT
<213> ORGANISM: Homo sapiens

<400> SEQUENCE: 36

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230

<210> SEQ ID NO 37
<211> LENGTH: 492
<212> TYPE: PRT
<213> ORGANISM: Homo sapiens

<400> SEQUENCE: 37

Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45
```

-continued

```
Val Pro Gln Tyr Ala Pro Arg Val Leu Thr Gln Ala Ser Asn Pro Val
 50                  55                  60

Val Cys Thr Gln Pro Lys Ser Pro Ser Gly Thr Val Cys Thr Ser Lys
 65                  70                  75                  80

Thr Lys Lys Ala Leu Cys Ile Thr Leu Thr Leu Gly Thr Phe Leu Val
                 85                  90                  95

Gly Ala Ala Leu Ala Ala Gly Leu Leu Trp Lys Phe Met Gly Ser Lys
                100                 105                 110

Cys Ser Asn Ser Gly Ile Glu Cys Asp Ser Ser Gly Thr Cys Ile Asn
                115                 120                 125

Pro Ser Asn Trp Cys Asp Gly Val Ser His Cys Pro Gly Gly Glu Asp
130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
                180                 185                 190

Asn Phe Tyr Ser Ser Gln Gly Ile Val Asp Asp Ser Gly Ser Thr Ser
                195                 200                 205

Phe Met Lys Leu Asn Thr Ser Ala Gly Asn Val Asp Ile Tyr Lys Lys
                210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
                260                 265                 270

Leu His Val Gln Asn Val His Val Cys Gly Gly Ser Ile Ile Thr Pro
                275                 280                 285

Glu Trp Ile Val Thr Ala Ala His Cys Val Glu Lys Pro Leu Asn Asn
                290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
                340                 345                 350

Lys Pro Leu Thr Phe Asn Asp Leu Val Lys Pro Val Cys Leu Pro Asn
                355                 360                 365

Pro Gly Met Met Leu Gln Pro Glu Gln Leu Cys Trp Ile Ser Gly Trp
370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
                420                 425                 430

Asn Val Asp Ser Cys Gln Gly Asp Ser Gly Gly Pro Leu Val Thr Ser
                435                 440                 445
```

-continued

```
Lys Asn Asn Ile Trp Trp Leu Ile Gly Asp Thr Ser Trp Gly Ser Gly
    450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490
```